US008629282B2

(12) United States Patent
Cherney et al.

(10) Patent No.: US 8,629,282 B2
(45) Date of Patent: Jan. 14, 2014

(54) HETEROCYCLIC COMPOUNDS AS S1P1 AGONISTS FOR THE TREATMENT OF AUTOIMMUNE AND VASCULAR DISEASES

(75) Inventors: Robert J. Cherney, Newtown, PA (US); Zhongyu Wang, Vernon, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/883,358

(22) PCT Filed: Nov. 2, 2011

(86) PCT No.: PCT/US2011/058891
§ 371 (c)(1),
(2), (4) Date: May 3, 2013

(87) PCT Pub. No.: WO2012/061459
PCT Pub. Date: May 10, 2012

(65) Prior Publication Data
US 2013/0237566 A1    Sep. 12, 2013

Related U.S. Application Data

(60) Provisional application No. 61/409,682, filed on Nov. 3, 2010.

(51) Int. Cl.
C07D 271/06    (2006.01)
(52) U.S. Cl.
USPC ........................................... 548/131
(58) Field of Classification Search
None
See application file for complete search history.

(56) References Cited

U.S. PATENT DOCUMENTS

| 6,069,143 | A | 5/2000 | Ali et al. |
| 7,678,820 | B2 | 3/2010 | Harada et al. |
| 7,687,491 | B2 | 3/2010 | Nishi et al. |
| 8,354,398 | B2 | 1/2013 | Watterson et al. |
| 8,389,509 | B2 | 3/2013 | Dyckman et al. |
| 8,399,451 | B2 | 3/2013 | Gilmore et al. |
| 8,404,672 | B2 | 3/2013 | Pitts et al. |
| 2008/0200535 | A1 | 8/2008 | Ohmori et al. |
| 2013/0158001 | A1 | 6/2013 | Das et al. |

FOREIGN PATENT DOCUMENTS

| WO | WO 03/061567 | 7/2003 |
| WO | WO 03/062248 | 7/2003 |
| WO | WO 03/062252 | 7/2003 |
| WO | WO 03/073986 | 9/2003 |
| WO | WO 03/105771 | 12/2003 |
| WO | WO 2005/000833 | 1/2005 |
| WO | WO 2005/058848 | 6/2005 |
| WO | WO 2005/082089 | 9/2005 |
| WO | WO 2006/047195 | 5/2006 |
| WO | WO 2006/100633 | 9/2006 |
| WO | WO 2006/131336 | 12/2006 |
| WO | WO 2007/024922 | 3/2007 |
| WO | WO 2007/088450 | 8/2007 |
| WO | WO 2007/109330 | 9/2007 |
| WO | WO 2008/029370 | 3/2008 |

(Continued)

OTHER PUBLICATIONS

Hale, J.J., et al., "A Rational Utilization of High-Throughput Screening Affords Selective, Orally Bioavailable 1-Benzyl-3-carboxyazetidine Sphingosine-1-phosphate-1 Receptor Agonists," J. Med. Chem., 47, pp. 6662-6665 (2004).

(Continued)

*Primary Examiner* — Dennis Heyer
*Assistant Examiner* — Daniel M Podgorski
(74) *Attorney, Agent, or Firm* — Gary D. Greenblatt

(57) ABSTRACT

Disclosed are compounds of Formula (I) or stereoisomers, salts, or prodrugs thereof, wherein: W is $CH_2$ or O; Q is Formula (II), Formula (III) or Formula (IV); and $R^1$, $R^2$, $R^3$, $R^4$, n, and G are defined herein. Also disclosed are methods of using such compounds as selective agonists for G protein-coupled receptor $S1P_1$, and pharmaceutical compositions comprising such compounds. These compounds are useful in treating, preventing, or slowing the progression of diseases or disorders in a variety of therapeutic areas, such as autoimmune diseases and vascular disease.

7 Claims, No Drawings

(56) References Cited

FOREIGN PATENT DOCUMENTS

| WO | WO 2008/074820 | 6/2008 | | |
|----|----------------|--------|---|---|
| WO | WO 2008/114157 | 9/2008 | | |
| WO | WO 2009/043889 | 4/2009 | | |
| WO | WO 2009/057079 | 5/2009 | | |
| WO | WO 2009/080728 | 7/2009 | | |
| WO | WO 2010/069949 | 6/2010 | | |
| WO | WO 2010069949 A1 * | 6/2010 | ........... | C07D 413/04 |
| WO | WO 2010/072352 | 7/2010 | | |
| WO | WO 2010/081692 | 7/2010 | | |
| WO | WO 2011/059784 | 5/2011 | | |
| WO | WO 2011/133734 | 10/2011 | | |
| WO | WO 2012/040532 | 3/2012 | | |

OTHER PUBLICATIONS

International Preliminary Report on Patentability for PCT/US2011/058891, dated Dec. 30, 2011.

* cited by examiner

HETEROCYCLIC COMPOUNDS AS S1P1 AGONISTS FOR THE TREATMENT OF AUTOIMMUNE AND VASCULAR DISEASES

FIELD OF THE INVENTION

The present invention generally relates to substituted bicyclic compounds useful as $S1P_1$ agonists. Provided herein are substituted bicyclic compounds, compositions comprising such compounds, and methods of their use. The invention further pertains to pharmaceutical compositions comprising at least one compound according to the invention that are useful for the treatment of conditions related to $S1P_1$ agonism, such as autoimmune diseases and vascular disease.

BACKGROUND OF THE INVENTION

Sphingosine-1-phosphate (S1P) has been demonstrated to induce many cellular effects, including those that result in platelet aggregation, cell proliferation, cell morphology, tumor cell invasion, endothelial cell and leukocyte chemotaxis, endothelial cell in vitro angiogenesis, and lymphocyte trafficking. S1P receptors are therefore good targets for a wide variety of therapeutic applications such as tumor growth inhibition, vascular disease, and autoimmune diseases. S1P signals cells in part via a set of G protein-coupled receptors named $S1P_1$ or S1P1, $S1P_2$ or S1P2, $S1P_3$ or S1P3, $S1P_4$ or S1P4, and $S1P_5$ or SIPS (formerly called EDG-1, EDG-5, EDG-3, EDG-6, and EDG-8, respectively).

S1P is important in the entire human body as it is also a major regulator of the vascular and immune systems. In the vascular system, S1P regulates angiogenesis, vascular stability, and permeability. In the immune system, S1P is recognized as a major regulator of trafficking of T- and B-cells. S1P interaction with its receptor $S1P_1$ is needed for the egress of immune cells from the lymphoid organs (such as thymus and lymph nodes) into the lymphatic vessels. Therefore, modulation of S1P receptors was shown to be critical for immunomodulation, and S1P receptor modulators are novel immunosuppressive agents.

The $S1P_1$ receptor is expressed in a number of tissues. It is the predominant family member expressed on lymphocytes and plays an important role in lymphocyte trafficking. Downregulation of the $S1P_1$ receptor disrupts lymphocyte migration and homing to various tissues. This results in sequestration of the lymphocytes in lymph organs thereby decreasing the number of circulating lymphocytes that are capable of migration to the affected tissues. Thus, development of an $S1P_1$ receptor agent that suppresses lymphocyte migration to the target sites associated with autoimmune and aberrant inflammatory processes could be efficacious in a number of autoimmune and inflammatory disease states.

Among the five S1P receptors, $S1P_1$ has a widespread distribution and is highly abundant on endothelial cells where it works in concert with $S1P_3$ to regulate cell migration, differentiation, and barrier function. Inhibition of lymphocyte recirculation by non-selective S1P receptor modulation produces clinical immunosuppression preventing transplant rejection, but such modulation also results in transient bradycardia. Studies have shown that $S1P_1$ activity is significantly correlated with depletion of circulating lymphocytes. In contrast, $S1P_3$ receptor agonism is not required for efficacy. Instead, $S1P_3$ activity plays a significant role in the observed acute toxicity of nonselective S1P receptor agonists, resulting in the undesirable cardiovascular effects, such as bradycardia and hypertension. (See, e.g., Hale et al., *Bioorg. Med. Chem. Lett.*, 14:3501 (2004); Sanna et al., *J. Biol. Chem.*, 279:13839 (2004); Anliker et al., *J. Biol. Chem.*, 279:20555 (2004); Mandala et al., *J. Pharmacol. Exp. Ther.*, 309:758 (2004).)

An example of an $S1P_1$ agonist is FTY720. This immunosuppressive compound FTY720 (JPI 1080026-A) has been shown to reduce circulating lymphocytes in animals and humans, and to have disease modulating activity in animal models of organ rejection and immune disorders. The use of FTY720 in humans has been effective in reducing the rate of organ rejection in human renal transplantation and increasing the remission rates in relapsing remitting multiple sclerosis (see Brinkman et al., *J. Biol. Chem.*, 277:21453 (2002); Mandala et al., *Science*, 296:346 (2002); Fujino et al., *J. Pharmacol. Exp. Ther.*, 305:45658 (2003); Brinkman et al., *Am. J. Transplant.*, 4:1019 (2004); Webb et al., *J. Neuroimmunol.*, 153:108 (2004); Morris et al., *Eur. J. Immunol.*, 35:3570 (2005); Chiba, *Pharmacology & Therapeutics*, 108:308 (2005); Kahan et al., *Transplantation*, 76:1079 (2003); and Kappos et al., *N. Engl. J. Med.*, 335:1124 (2006)). Subsequent to its discovery, it has been established that FTY720 is a prodrug, which is phosphorylated in vivo by sphingosine kinases to a more biologically active agent that has agonist activity at the $S1P_1$, $S1P_3$, $S1P_4$, and $S1P_5$ receptors. It is this activity on the S1P family of receptors that is largely responsible for the pharmacological effects of FTY720 in animals and humans.

Clinical studies have demonstrated that treatment with FTY720 results in bradycardia in the first 24 hours of treatment (Kappos et al., *N. Engl. J. Med.*, 335:1124 (2006)). The observed bradycardia is commonly thought to be due to agonism at the $S1P_3$ receptor. This conclusion is based on a number of cell based and animal experiments. These include the use of $S1P_3$ knockout animals which, unlike wild type mice, do not demonstrate bradycardia following FTY720 administration and the use of $S1P_1$ selective compounds. (Hale et al., *Bioorg. Med. Chem. Lett.*, 14:3501 (2004); Sanna et al., *J. Biol. Chem.*, 279:13839 (2004); and Koyrakh et al., *Am. J. Transplant.*, 5:529 (2005)).

The following applications have described compounds as $S1P_1$ agonists: WO 03/061567 (U.S. Patent Publication No. 2005/0070506), WO 03/062248 (U.S. Pat. No. 7,351,725), WO 03/062252 (U.S. Pat. No. 7,479,504), WO 03/073986 (U.S. Pat. No. 7,309,721), WO 03/105771, WO 05/058848, WO 05/000833, WO 05/082089 (U.S. Patent Publication No. 2007/0203100), WO 06/047195, WO 06/100633, WO 06/115188, WO 06/131336, WO 2007/024922, WO 07/109, 330, WO 07/116,866, WO 08/023,783 (U.S. Patent Publication No. 2008/0200535), WO 08/029,370, WO 08/114,157, WO 08/074,820, WO 09/043,889, WO 09/057,079, and U.S. Pat. No. 6,069,143. Also see Hale et al., *J. Med. Chem.*, 47:6662 (2004).

There still remains a need for compounds useful as S1P1 agonists and yet having selectivity over S1P3.

Applicants have found potent compounds that have activity as S1P1 agonists. Further, applicants have found compounds that have activity as S1P1 agonists and are selective over S1P3. These compounds are provided to be useful as pharmaceuticals with desirable stability, bioavailability, therapeutic index, and toxicity values that are important to their drugability.

BRIEF STATEMENT OF THE INVENTION

The present invention provides substituted bicyclic compounds, which are useful as modulators of S1P1 activity, including stereoisomers, salts, solvates, and prodrugs thereof.

The present invention also provides processes and intermediates for making the compounds of the present invention or stereoisomers, salts, or prodrugs thereof.

The present invention also provides pharmaceutical compositions comprising a compound of Formula (I), or stereoisomers, pharmaceutically acceptable salts, or prodrugs thereof; and a pharmaceutically acceptable carrier.

The present invention also provides a method of treating a disease or disorder associated with the activity of G protein-coupled receptor S1P1, the method comprising administering to a mammalian patient a compound of Formula (I) or stereoisomers, pharmaceutically acceptable salts, or prodrugs thereof.

The present invention also provides the compounds of the present invention or stereoisomers, pharmaceutically acceptable salts, or prodrugs thereof, for use in therapy.

The present invention also provides the use of the compounds of the present invention or stereoisomers, pharmaceutically acceptable salts, or prodrugs thereof, for the manufacture of a medicament for the treatment or prophylaxis of $S1P_1$ receptor-related conditions, such as autoimmune and vascular diseases.

The compounds of Formula (I) and compositions comprising the compounds are $S1P_1$ agonists, which are selective for $S1P_1$ activity over $S1P_3$ activity. The compounds of Formula (I) and compositions comprising said compounds may be used in treating, preventing or curing various $S1P_1$ receptor-related conditions while reducing or minimizing the side effects due to $S1P_3$ activity. Pharmaceutical compositions comprising these compounds are useful in treating, preventing, or slowing the progression of diseases or disorders in a variety of therapeutic areas, such as autoimmune and vascular diseases.

DETAILED DESCRIPTION OF THE INVENTION

In a first aspect, the present invention provides compounds of Formula (I):

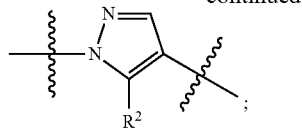

or stereoisomers, salts, or prodrugs thereof, wherein:

W is $CH_2$ or O;

Q is

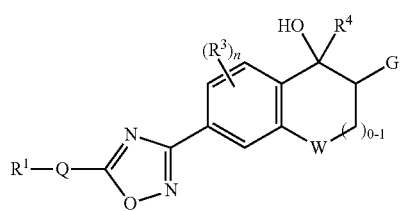

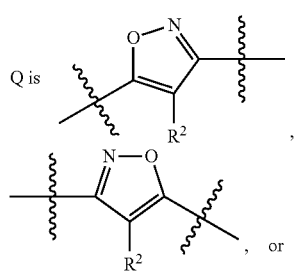

$R^1$ is:
(i) $C_{3-6}$alkyl;
(ii) $C_{3-7}$cycloalkyl substituted with zero to 3 substituents independently selected from halo, —CN, $C_{1-4}$alkyl, $C_{1-4}$alkoxy, $C_{1-3}$fluoroalkyl, $C_{1-3}$-chloroalkyl, and/or $C_{1-2}$fluoroalkoxy;
(iii) phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy; or
(iv) pyridinyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy;

$R^2$ is $C_{1-6}$alkyl, $C_{1-3}$fluoroalkyl, $C_{3-7}$cycloalkyl, or phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy;

n is zero, 1, or 2;

each $R^3$ is independently $C_{1-3}$alkyl, F, Cl, $C_{1-3}$fluoroalkyl, $C_{1-3}$chloroalkyl, —CN, $C_{1-3}$alkoxy, and/or $C_{1-3}$fluoroalkoxy;

$R^4$ is H or —$CH_3$;

G is:
(i) —$NR^aR^a$;
(ii) —$NH(CR^dR^d)_{1-3}C(O)OR^a$, —$NH(CR^dR^d)_{1-4}OH$, —$NHR^e$, or $NR^eR^e$;
(iii) —$NH(CR^dR^d)_{1-3}CR^bR^cC(O)OR^a$, wherein $R^b$ and $R^c$ together with the carbon atom to which they are attached form a $C_{3-6}$spirocycloalkyl ring;
(iv) —$NR^a[(CR^aR^a)_{0-3}(C_{3-6}cycloalkyl)]$, wherein said $C_{3-6}$cycloalkyl is substituted with zero to 2 substituents independently selected from —$(CR^dR^d)_{1-3}C(O)OR^a$ and/or —$(CR^dR^d)_{1-4}OH$;
(v) 5- to 6-membered heterocyclyl having at least one nitrogen heteroatom, wherein said heterocyclyl is substituted with zero to 2 substituents independently selected from —$(CR^dR^d)_{0-3}C(O)OR^a$ and/or —$(CR^dR^d)_{0-4}H$; or
(vi) —$NR^aC(O)OR^a$;

each $R^a$ is independently H, $C_{1-4}$alkyl, and/or $C_{1-3}$hydroxyalkyl;

each $R^d$ is independently H, —OH, F, and/or —$CH_3$; and each $R^e$ is independently —$(CR^aR^a)_{1-3}C(O)OR^a$.

One embodiment provides compounds of Formula (I) or stereoisomers, salts, or prodrugs thereof, wherein Q is

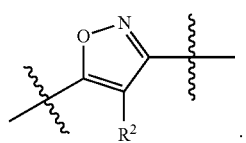

Compounds of this embodiment have the structure represented by Formula (Ia):

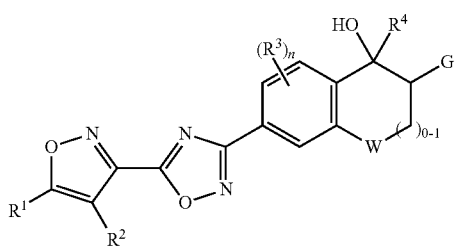

wherein $R^1$, $R^2$, $R^3$, $R^4$, W, n, and G are defined in the first aspect of the invention. Compounds of this embodiment in which $R^4$ is H have the structure represented by Formula (IIa):

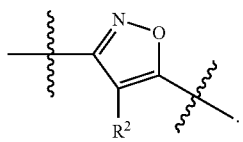

One embodiment provides compounds of Formula (I) or stereoisomers, salts, or prodrugs thereof, wherein Q is

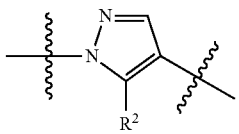

Compounds of this embodiment have the structure represented by Formula (Ib):

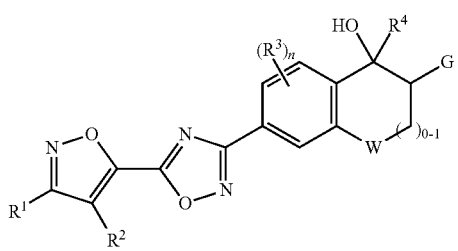

wherein $R^1$, $R^2$, $R^3$, $R^4$, W, n, and G are defined in the first aspect of the invention. Compounds of this embodiment in which $R^4$ is H have the structure represented by Formula (IIb):

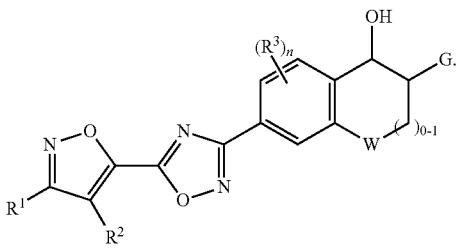

One embodiment provides compounds of Formula (I) or stereoisomers, salts, or prodrugs thereof, wherein Q is Compounds of this embodiment have the structure represented by Formula (Ic):

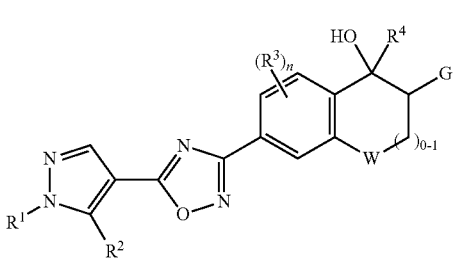

wherein $R^1$, $R^2$, $R^3$, $R^4$, W, n, and G are defined in the first aspect of the invention. Compounds of this embodiment in which $R^4$ is H have the structure represented by Formula (IIc):

One embodiment provides compounds of Formula (I) or stereoisomers, salts, or prodrugs thereof wherein $R^1$ is $C_{3-6}$alkyl, and Q, $R^2$, $R^3$, $R^4$, W, n, and G are defined in the first aspect of the invention. For example, included in this embodiment are compounds in which Q is

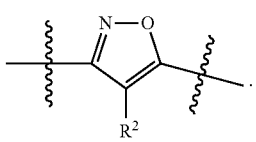

Also included in this embodiment are compounds in which R² is —CF₃ and n is zero or 1.

One embodiment provides compounds of Formula (I) or stereoisomers, salts, or prodrugs thereof wherein R¹ is $C_{3-7}$cycloalkyl substituted with zero to 3 substituents independently selected from halo, —CN, $C_{1-4}$alkyl, $C_{1-4}$alkoxy, $C_{1-3}$fluoroalkyl, $C_{1-3}$chloroalkyl, and/or $C_{1-2}$fluoroalkoxy; and Q, R², R³, R⁴, W, n, and G are defined in the first aspect of the invention. For example, included in this embodiment are compounds in which Q is

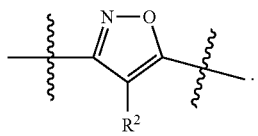

Also included in this embodiment are compounds in which R² is —CF₃ and n is zero or 1.

One embodiment provides compounds of Formula (I) or stereoisomers, salts, or prodrugs thereof wherein R¹ is phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy; and Q, R², R³, R⁴, W, n, and G are defined in the first aspect of the invention. For example, included in this embodiment are compounds in which Q is

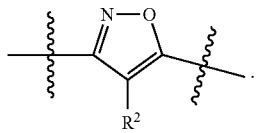

Also included in this embodiment are compounds in which R² is —CF₃ and n is zero or 1.

One embodiment provides compounds of Formula (I) or stereoisomers, salts, or prodrugs thereof wherein R¹ is pyridinyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy; and Q, R², R³, R⁴, W, n, and G are defined in the first aspect of the invention. For example, included in this embodiment are compounds in which Q is

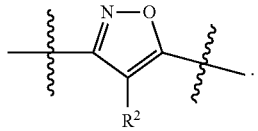

Also included in this embodiment are compounds in which R² is —CF₃ and n is zero or 1.

One embodiment provides compounds of Formula (I) or stereoisomers, salts, or prodrugs thereof wherein R¹ is phenyl, n is zero, R⁴ is H, and Q, R², R³, R⁴, W, and G are defined in the first aspect of the invention. Compounds of this embodiment have the structure represented by Formula (III):

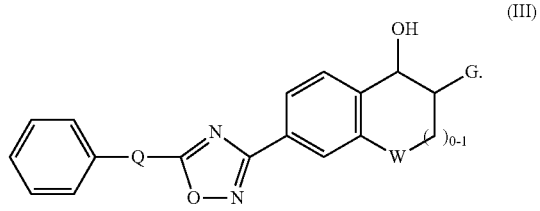

Included in this embodiment are compounds having the structures represented by Formula (IIIa), (IIIb), and (IIIc):

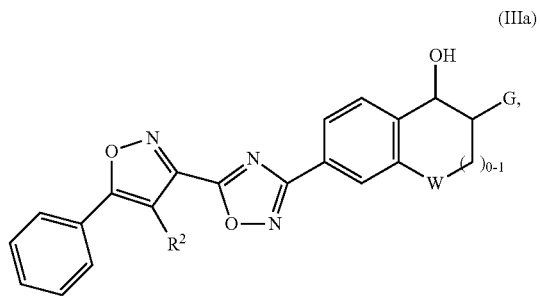

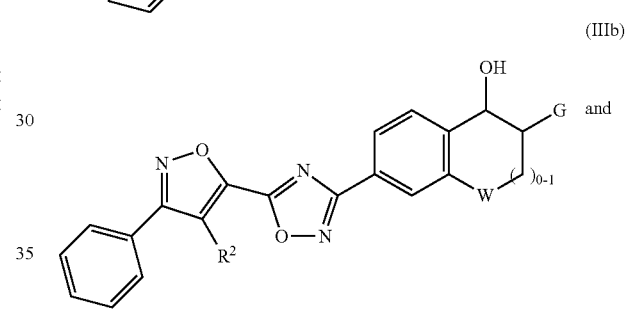

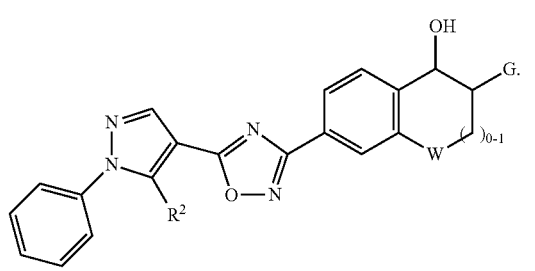

Also included in this embodiment are compounds of Formula (III), (IIIa), (IIIb), and (IIIc) in which R² is —CF₃.

One embodiment provides compounds of Formula (I) or stereoisomers, salts, or prodrugs thereof, wherein W is CH₂. Compounds of this embodiment have the structure represented by Formula (IV):

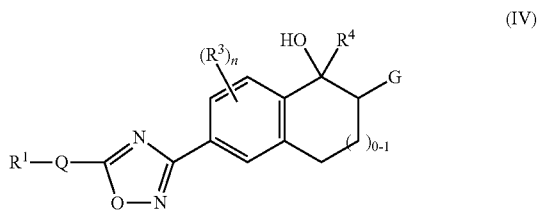

wherein $R^1$, $R^2$, $R^3$, $R^4$, Q, n, and G are defined in the first aspect of the invention. Included in this embodiment are compounds having the structures represented by Formula (IVa) and (IVb):

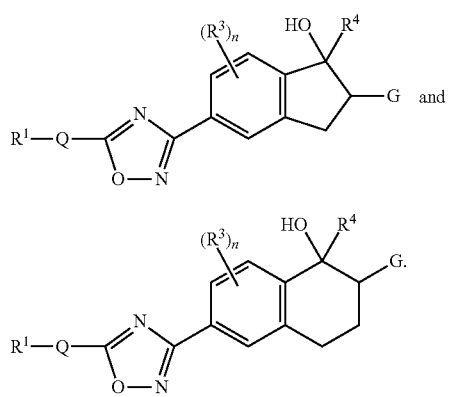

Also included in this embodiment are compounds in which $R^4$ is H. Other compounds of this embodiment include compounds having the structure represented by Formula (IVc):

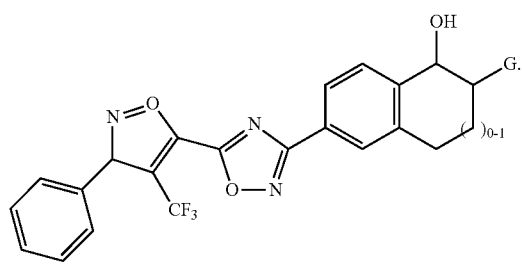

One embodiment provides compounds of Formula (I) or stereoisomers, salts, or prodrugs thereof, wherein W is O. Compounds of this embodiment have the structure represented by Formula (V):

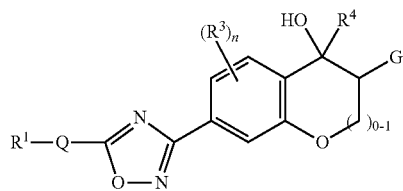

wherein $R^1$, $R^2$, $R^3$, $R^4$, Q, n, and G are defined in the first aspect of the invention. Included in this embodiment are compounds having the structures represented by Formula (Va) and (Vb):

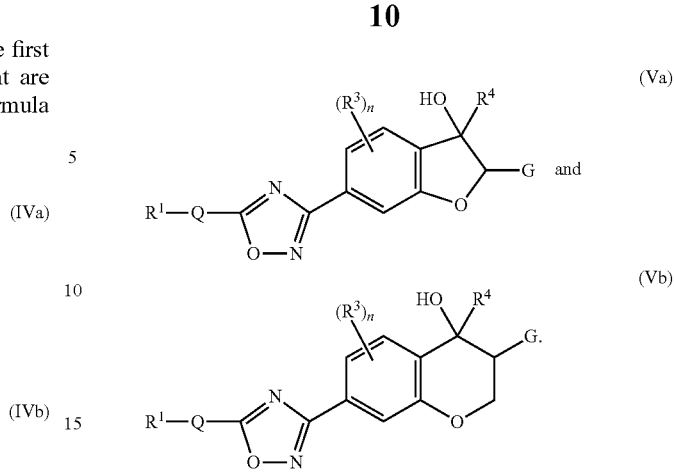

Also included in this embodiment are compounds in which $R^4$ is H. Other compounds of this embodiment include compounds having the structure represented by Formula (Vc):

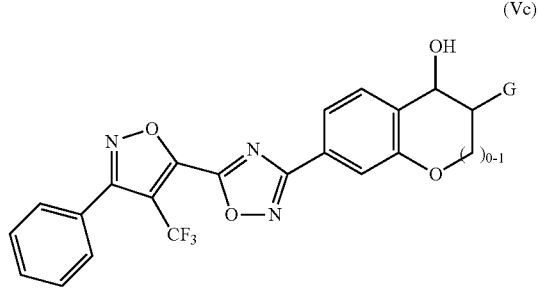

and the compounds having the structure represented by Formula (Vd)

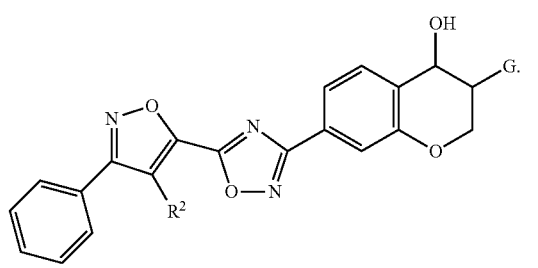

One embodiment provides compounds of Formula (I) or stereoisomers, salts, or prodrugs thereof wherein G is —$NR^aR^a$; and Q, $R^1$, $R^2$, $R^3$, $R^4$, $R^a$, W, W and n are defined in the first aspect of the invention. For example, included in this embodiment are compounds in which Q is

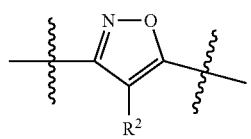

and $R^1$ is phenyl Also included in this embodiment are compounds in which $R^2$ is —$CF_3$ and n is zero or 1.

One embodiment provides compounds of Formula (I) or stereoisomers, salts, or prodrugs thereof wherein G is —NH(CR$^d$R$^d$)$_{1-3}$C(O)OR$^a$, —NH(CR$^d$R$^d$)$_{1-4}$H, —NHR$^e$, or NR$^e$R$^e$; and Q, R$^1$, R$^2$, R$^3$, R$^4$, R$^a$, R$^d$, R$^e$, W, and n are defined in the first aspect of the invention. For example, included in this embodiment are compounds in which Q is

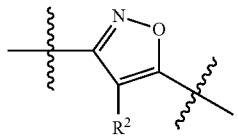

and R$^1$ is phenyl Also included in this embodiment are compounds in which R$^2$ is —CF$_3$ and n is zero or 1.

One embodiment provides compounds of Formula (I) or stereoisomers, salts, or prodrugs thereof wherein G is —NH(CR$^d$R$^d$)$_{1-3}$CR$^b$R$^c$C(O)OR$^a$, wherein R$^b$ and R$^c$ together with the carbon atom to which they are attached form a C$_{3-6}$spirocycloalkyl ring; and Q, R$^1$, R$^2$, R$^3$, R$^4$, R$^a$, R$^d$, R$^e$, W, and n are defined in the first aspect of the invention. For example, included in this embodiment are compounds in which Q is

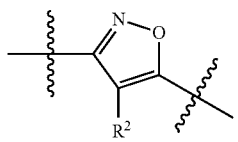

and R$^1$ is phenyl Also included in this embodiment are compounds in which R$^2$ is —CF$_3$ and n is zero or 1.

One embodiment provides compounds of Formula (I) or stereoisomers, salts, or prodrugs thereof wherein G is —NR$^a$[(CR$^a$R$^a$)$_{0-3}$(C$_{3-6}$cycloalkyl)], wherein said C$_{3-6}$cycloalkyl is substituted with zero to 2 substituents independently selected from (CR$^d$R$^d$)$_{1-3}$C(O)OR$^a$ and/or —(CR$^d$R$^d$)$_{1-4}$OH; and Q, R$^1$, R$^2$, R$^3$, R$^4$, R$^a$, R$^d$, R$^e$, W, and n are defined in the first aspect of the invention. For example, included in this embodiment are compounds in which Q is

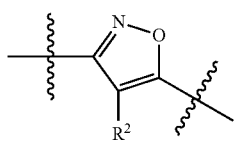

and R$^1$ is phenyl Also included in this embodiment are compounds in which R$^2$ is —CF$_3$ and n is zero or 1.

One embodiment provides compounds of Formula (I) or stereoisomers, salts, or prodrugs thereof wherein G is a 5- to 6-membered heterocyclyl having at least one nitrogen heteroatom, wherein said heterocyclyl is substituted with zero to 2 substituents independently selected from —(CR$^d$R$^d$)$_{0-3}$C(O)OR$^a$ and/or —(CR$^d$R$^d$)$_{0-4}$H; and Q, R$^1$, R$^2$, R$^3$, R$^4$, R$^a$, R$^d$, W, and n are defined in the first aspect of the invention. For example, included in this embodiment are compounds in which Q is

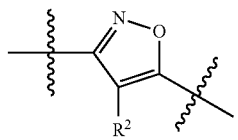

and R$^1$ is phenyl. Also included in this embodiment are compounds in which R$^2$ is —CF$_3$ and n is zero or 1.

One embodiment provides compounds of Formula (I) or stereoisomers, salts, or prodrugs thereof wherein G is —NR$^a$C(O)OR$^a$; and Q, R$^1$, R$^2$, R$^3$, R$^4$, R$^a$, R$^d$, W, and n are defined in the first aspect of the invention. For example, included in this embodiment are compounds in which Q is

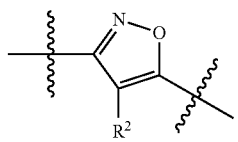

and R$^1$ is phenyl. Also included in this embodiment are compounds in which R$^2$ is —CF$_3$ and n is zero or 1.

One embodiment provides compounds of Formula (III):

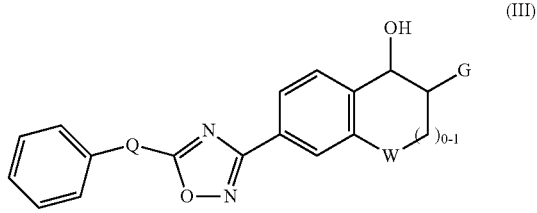

(III)

or stereoisomers, salts, or prodrugs thereof, wherein:
W is CH$_2$ or O;
Q is

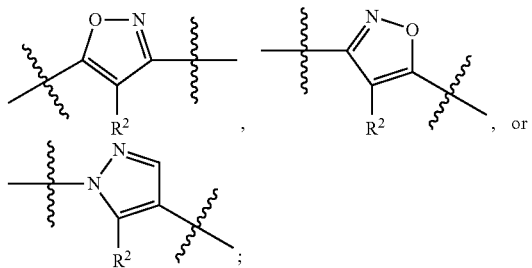

R$^2$ is —CF$_3$; and
G is:
(i) —NR$^a$R$^a$;
(ii) —NH(CR$^d$R$^d$)$_{1-3}$C(O)OR$^a$, —NHR$^e$, or NR$^e$R$^e$;
(iii) —NH(CH$_2$)$_{1-3}$CR$^b$R$^c$C(O)OR$^a$, wherein R$^b$ and R$^c$ together with the carbon atom to which they are attached form a C$_{3-6}$spirocycloalkyl ring;
(iv) —NR$^a$[(CR$^a$R$^a$)$_{0-2}$(C$_{4-6}$cycloalkyl)], wherein said C$_{4-6}$cycloalkyl is substituted with zero to 2 substituents independently selected from —(CR$^d$R$^d$)$_{1-3}$C(O)OR$^a$ and/or —(CR$^d$R$^d$)$_{1-4}$OH;

(v) piperidinyl, piperazinyl, or morpholinyl, each substituted with zero to 2 substituents independently selected from —(CR$^d$R$^d$)$_{0-3}$C(O)OR$^a$ and/or —(CR$^d$R$^d$)$_{0-4}$OH; or (vi) —NR$^a$C(O)OR$^a$;

each R$^a$ is independently H and/or C$_{1-4}$alkyl;

each R$^d$ is independently H, —OH, F, and/or —CH$_3$; and each R$^e$ is independently —(CH$_2$)$_{1-3}$C(O)OR$^a$.

One embodiment provides compounds of Formula (IIIa):

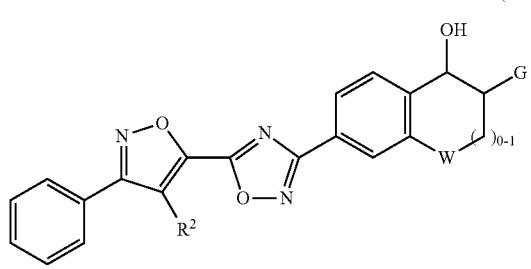

(IIIa)

or stereoisomers, salts, or prodrugs thereof, wherein:

W is CH$_2$ or O;

R$^2$ is —CF$_3$;

G is:
(i) —NR$^a$R$^a$;
(ii) —NH(CR$^d$R$^d$)$_{1-3}$C(O)OR$^a$, —NHR$^e$, or NR$^e$R$^e$;
(iii) —NH(CH$_2$)$_{1-3}$CR$^b$R$^c$C(O)OR$^a$, wherein R$^b$ and R$^c$ together with the carbon atom to which they are attached form a C$_{3-6}$spirocycloalkyl ring;
(iv) —NR$^a$(C$_{4-6}$cycloalkyl), wherein said C$_{4-6}$cycloalkyl is substituted with zero to 1 substituent selected from —(CH$_2$)$_{1-3}$C(O)OR$^a$;
(v) piperidinyl substituted with zero to 1 substituent selected from —(CH$_2$)$_{0-3}$C(O)OR$^a$; or
(vi) —NR$^a$C(O)OR$^a$;

each R$^a$ is independently H and/or C$_{1-4}$alkyl;

each R$^d$ is independently H and/or —CH$_3$; and each R$^e$ is independently —(CH$_2$)$_{1-3}$C(O)OR$^a$.

One embodiment provides compounds of Formula (IVc):

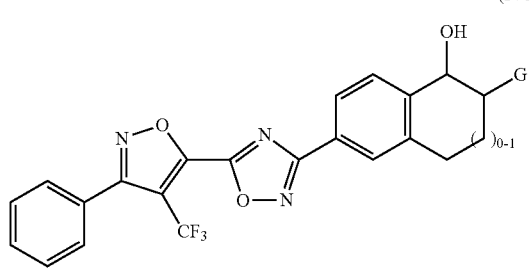

(IVc)

or stereoisomers, salts, or prodrugs thereof, wherein: G is —NH$_2$ or —NH(CH$_2$)$_{1-2}$C(O)OH.

One embodiment provides compounds of Formula (Vd):

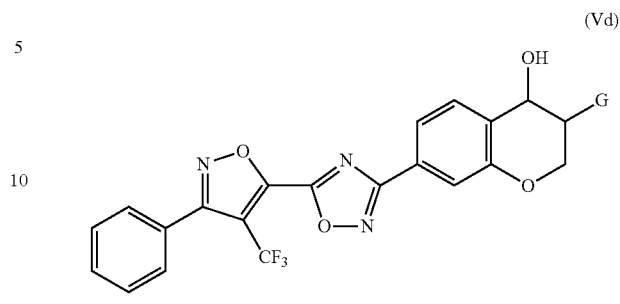

(Vd)

or stereoisomers, salts, or prodrugs thereof, wherein:

G is:
(i) —NHR$^a$ or —N(CH$_3$)$_2$;
(ii) —NH(CH$_2$)$_{1-3}$C(O)OR$^a$, —NHCH$_2$CH(CH$_3$)C(O)OR$^a$, —NHCH$_2$C(CH$_3$)$_2$C(O)OR$^a$, —NHCH(CH$_3$)(CH$_2$)$_{1-2}$C(O)OR$^a$, or —N(CH$_2$CH$_2$CH$_2$C(O)OH)$_2$;
(iii) —NHCH$_2$CR$^b$R$^c$C(O)OR$^5$, wherein R$^b$ and R$^c$ together with the carbon atom to which they are attached form a C$_{3-6}$spirocycloalkyl ring;
(iv) —NH(C$_{4-6}$cycloalkyl), wherein said C$_{4-6}$cycloalkyl is substituted with zero to 1 substituent selected from —C(O)OR$^a$;
(v) piperidinyl substituted with zero to 1 substituent selected from —CH$_2$C(O)OR$^a$; or
(vi) —NHC(O)O(C$_{1-4}$alkyl); and R$^a$ is H or C$_{1-4}$alkyl.

One embodiment provides a compound of Formula (I) or stereoisomers, salts, or prodrugs thereof, wherein said compound is selected from: racemic-2-amino-5-(5-(3-phenyl-4-(trifluoromethyl)isoxazol-5-yl)-1,2,4-oxadiazol-3-yl)-2,3-dihydro-1H-inden-1-ol, TFA salt (2); and racemic-3-(1-hydroxy-5-(5-(3-phenyl-4-(trifluoromethyl)isoxazol-5-yl)-1,2,4-oxadiazol-3-yl)-2,3-dihydro-1H-inden-2-ylamino) propanoic acid, TFA salt (55).

One embodiment provides a compound of Formula (I) or stereoisomers, salts, or prodrugs thereof, wherein said compound is selected from: racemic-2-amino-6-(5-(3-phenyl-4-(trifluoromethyl)isoxazol-5-yl)-1,2,4-oxadiazol-3-yl)-1,2,3,4-tetrahydronaphthalen-1-ol, TFA salt (3); racemic-3-(1-hydroxy-6-(5-(3-phenyl-4-(trifluoromethyl)isoxazol-5-yl)-1,2,4-oxadiazol-3-yl)-1,2,3,4-tetrahydronaphthalen-2-ylamino)propanoic acid, TFA salt (56); racemic-2-(1-hydroxy-6-(5-(3-phenyl-4-(trifluoromethyl)isoxazol-5-yl)-1,2,4-oxadiazol-3-yl)-1,2,3,4-tetrahydronaphthalen-2-ylamino)acetic acid, TFA salt (71); and racemic-4-(1-hydroxy-6-(5-(3-phenyl-4-(trifluoromethyl)isoxazol-5-yl)-1,2,4-oxadiazol-3-yl)-1,2,3,4-tetrahydronaphthalen-2-ylamino)butanoic acid, TFA salt (72).

One embodiment provides a compound of Formula (I) or stereoisomers, salts, or prodrugs thereof, wherein said compound is selected from: racemic (3R*,4S*)-3-amino-7-(5-(3-phenyl-4-(trifluoromethyl)isoxazol-5-yl)-1,2,4-oxadiazol-3-yl)chroman-4-ol, TFA (1); racemic (3R*,4R*)-3-amino-7-(5-(3-phenyl-4-(trifluoromethyl)isoxazol-5-yl)-1,2,4-oxadiazol-3-yl)chroman-4-ol, TFA (4); racemic 3-((3R*,4R*)-4-hydroxy-7-(5-(3-phenyl-4-(trifluoromethyl)isoxazol-5-yl)-1,2,4-oxadiazol-3-yl)chroman-3-ylamino) propanoic acid, TFA salt (5); racemic (3R*,4S*)-tert-butyl-4-hydroxy-7-(5-(3-phenyl-4-(trifluoromethyl)isoxazol-5-yl)-1,2,4-oxadiazol-3-yl)chroman-3-ylcarbamate (6 and 7); (3S,4R)-3-amino-7-(5-(3-phenyl-4-(trifluoromethyl)isoxazol-5-yl)-1,2,4-oxadiazol-3-yl)chroman-4-ol, TFA salt (8); (3R,4S)-3-amino-7-(5-(3-phenyl-4-(trifluoromethyl)isoxazol-5-yl)-1,2,4-oxadiazol-3-yl)chroman-4-ol, TFA salt (9); racemic (3R*,4S*)-3-(isopropylamino)-7-(5-(3-phenyl-4-(trifluoromethyl)isoxazol-5-yl)-1,2,4-oxadiazol-3-yl)chroman-4-ol (10); racemic cis-3-(cyclohexylamino)-7-(5-(3-phenyl-4-(trifluoromethyl)isoxazol-5-yl)-1,2,4-oxadiazol-3-yl)chroman-4-ol, TFA salt (11); racemic 3-((3R*,4S*)-4-hydroxy-7-(5-(3-phenyl-4-(trifluoromethyl)isoxazol-5-yl)-1,2,4-oxadiazol-3-yl)chroman-3-ylamino)butanoic acid, TFA salt (12); racemic-ethyl 3-((3R*,4S*)-4-hydroxy-7-(5-(3-phenyl-4-(trifluoromethyl)isoxazol-5-yl)-1,2,4-oxadiazol-3-yl)chroman-3-ylamino)cyclohexanecarboxylate, TFA salt (13); racemic-ethyl 4-((3R*,4S*)-4-hydroxy-7-(5-(3-phenyl-4-(trifluoromethyl)isoxazol-5-yl)-1,2,4-oxadiazol-3-yl)chroman-3-ylamino)cyclohexanecarboxylate, TFA salt (14); racemic-3-((3R*,4S*)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt (15); racemic-4-((3R*,4S*)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt (16); racemic-(3R*,4S*)-3-(dimethylamino)-7-(5-(3-phenyl-4-(trifluoromethyl)isoxazol-5-yl)-1,2,4-oxadiazol-3-yl)chroman-4-ol (17); racemic-(3R*,4S*)-3-(cyclobutylamino)-7-(5-(3-phenyl-4-(trifluoromethyl)isoxazol-5-yl)-1,2,4-oxadiazol-3-yl)chroman-4-ol, TFA salt (18); racemic-(3R*,4S*)-3-(cyclopentylamino)-7-(5-(3-phenyl-4-(trifluoromethyl)isoxazol-5-yl)-1,2,4-oxadiazol-3-yl)chroman-4-ol, TFA salt (19); racemic-ethyl 3-((3R*,4S*)-4-hydroxy-7-(5-(3-phenyl-4-(trifluoromethyl)isoxazol-5-yl)-1,2,4-oxadiazol-3-yl)chroman-3-ylamino)-2-methylpropanoate, TFA salt (20); racemic-3-((3R*,4S*)-4-hydroxy-7-(5-(3-phenyl-4-(trifluoromethyl)isoxazol-5-yl)-1,2,4-oxadiazol-3-yl)chroman-3-ylamino)cyclopentanecarboxylic acid, TFA salt (21); racemic-3-((3R*,4S*)-4-hydroxy-7-(5-(3-phenyl-4-(trifluoromethyl)isoxazol-5-yl)-1,2,4-oxadiazol-3-yl)chroman-3-ylamino)-2-methylpropanoic acid, TFA salt (22); racemic-3-((3R*,4S*)-4-hydroxy-7-(5-(3-phenyl-4-(trifluoromethyl)isoxazol-5-yl)-1,2,4-oxadiazol-3-yl)chroman-3-ylamino)-2,2-dimethylpropanoic acid, TFA salt (23); (1S,3R)-3-((3S,4R)-4-hydroxy-7-(5-(3-phenyl-4-(trifluoromethyl)isoxazol-5-yl)-1,2,4-oxadiazol-3-yl)chroman-3-ylamino)cyclobutanecarboxylic acid, TFA salt (24); (1R,3S)-3-((3S,4R)-4-hydroxy-7-(5-(3-phenyl-4-(trifluoromethyl)isoxazol-5-yl)-1,2,4-oxadiazol-3-yl)chroman-3-ylamino)cyclobutanecarboxylic acid, TFA salt (25); 3-((3S,4R)-4-hydroxy-7-(5-(3-phenyl-4-(trifluoromethyl)isoxazol-5-yl)-1,2,4-oxadiazol-3-yl)chroman-3-ylamino) butanoic acid, TFA salt (26); 3-((3S,4R)-4-hydroxy-7-(5-(3-phenyl-4-(trifluoromethyl)isoxazol-5-yl)-1,2,4-oxadiazol-3-yl)chroman-3-ylamino)butanoic acid, TFA salt (27); 3-((3R,4S)-4-hydroxy-7-(5-(3-phenyl-4-(trifluoromethyl)isoxazol-5-yl)-1,2,4-oxadiazol-3-yl)chroman-3-ylamino)butanoic acid, TFA salt (28); 3-((3R,4S)-4-hydroxy-7-(5-(3-phenyl-4-(trifluoromethyl)isoxazol-5-yl)-1,2,4-oxadiazol-3-yl)chroman-3-ylamino)butanoic acid, TFA salt (29); 1-(((3R,4S)-4-hydroxy-7-(5-(3-phenyl-4-(trifluoromethyl)isoxazol-5-yl)-1,2,4-oxadiazol-3-yl)chroman-3-ylamino)methyl)cyclopropanecarboxylic acid, TFA salt (30); 1-(((3S,4R)-4-hydroxy-7-(5-(3-phenyl-4-(trifluoromethyl)isoxazol-5-yl)-1,2,4-oxadiazol-3-yl)chroman-3-ylamino)methyl)cyclopropanecarboxylic acid, TFA salt (31); (1S,3S)-3-((3R,4S)-4-hydroxy-7-(5-(3-phenyl-4-(trifluoromethyl)isoxazol-5-yl)-1,2,4-oxadiazol-3-yl)chroman-3-ylamino)cyclobutanecarboxylic acid, TFA salt (32); (1S,3s)-3-((3R,4S)-4-hydroxy-7-(5-(3-phenyl-4-(trifluoromethyl)isoxazol-5-yl)-1,2,4-oxadiazol-3-yl)chroman-3-ylamino)cyclobutanecarboxylic acid, TFA salt (33); 3-((3S,4R)-4-hydroxy-7-(5-(3-phenyl-4-(trifluoromethyl)isoxazol-5-yl)-1,2,4-oxadiazol-3-yl)chroman-3-ylamino)-2,2-dimethylpropanoic acid, TFA salt (34); 3-((3R,4S)-4-hydroxy-7-(5-(3-phenyl-4-(trifluoromethyl)isoxazol-5-yl)-1,2,4-oxadiazol-3-yl)chroman-3-ylamino)-2,2-dimethylpropanoic acid, TFA salt (35); 1-(((3S,4R)-4-hydroxy-7-(5-(3-phenyl-4-(trifluoromethyl)isoxazol-5-yl)-1,2,4-oxadiazol-3-yl)chroman-3-ylamino)methyl)cyclopentanecarboxylic acid, TFA salt (36); 1-(((3S,4R)-4-hydroxy-7-(5-(3-phenyl-4-(trifluoromethyl)isoxazol-5-yl)-1,2,4-oxadiazol-3-yl)chroman-3-ylamino)methyl)cyclohexanecarboxylic acid, TFA salt (37); 1-(((3R,4S)-4-hydroxy-7-(5-(3-phenyl-4-(trifluoromethyl)isoxazol-5-yl)-1,2,4-oxadiazol-3-yl)chroman-3-ylamino)methyl)cyclopentanecarboxylic acid, TFA salt (38); 1-(((3R,4S)-4-hydroxy-7-(5-(3-phenyl-4-(trifluoromethyl)isoxazol-5-yl)-1,2,4-oxadiazol-3-yl)chroman-3-ylamino)methyl)cyclohexanecarboxylic acid, TFA salt (39); 1-(((3S,4R)-4-hydroxy-7-(5-(3-phenyl-4-(trifluoromethyl)isoxazol-5-yl)-1,2,4-oxadiazol-3-yl)chroman-3-ylamino)methyl)cyclobutanecarboxylic acid, TFA salt (40); 1-(((3R,4S)-4-hydroxy-7-(5-(3-phenyl-4-(trifluoromethyl)isoxazol-5-yl)-1,2,4-oxadiazol-3-yl)chroman-3-ylamino)methyl)cyclobutanecarboxylic acid, TFA salt (41); 4,4'-((3R,4S)-4-hydroxy-7-(5-(3-phenyl-4-(trifluoromethyl)isoxazol-5-yl)-1,2,4-oxadiazol-3-yl)chroman-3-ylazanediyl)dibutanoic acid, TFA salt (42); 4-((3R,4S)-4-hydroxy-7-(5-(3-phenyl-4-(trifluoromethyl)isoxazol-5-yl)-1,2,4-oxadiazol-3-yl)chroman-3-ylamino)pentanoic acid, TFA salt (43); 4-((3R,4S)-4-hydroxy-7-(5-(3-phenyl-4-(trifluoromethyl)isoxazol-5-yl)-1,2,4-oxadiazol-3-yl)chroman-3-ylamino)pentanoic acid, TFA salt (44); 3-((3R,4S)-4-hydroxy-7-(5-(3-phenyl-4-(trifluoromethyl)isoxazol-5-yl)-1,2,4-oxadiazol-3-yl)chroman-3-ylamino)-2-methylpropanoic acid, TFA salt (45); 3-((3R,4S)-4-hydroxy-7-(5-(3-phenyl-4-(trifluoromethyl)isoxazol-5-yl)-1,2,4-oxadiazol-3-yl)chroman-3-ylamino)-2-methylpropanoic acid, TFA salt (46); racemic (3R*,4S*)-7-(5-(3-phenyl-4-(trifluoromethyl)isoxazol-5-yl)-1,2,4-oxadiazol-3-yl)-3-(piperidin-1-yl)chroman-4-ol, TFA salt (47); racemic-2-(1-((3R*,4S*)-4-hydroxy-7-(5-(3-phenyl-4-(trifluoromethyl)isoxazol-5-yl)-1,2,4-oxadiazol-3-yl)chroman-3-yl)piperidin-3-yl)acetic acid, TFA salt (48); 2-(-1-((3R,4S)-4-hydroxy-7-(5-(3-phenyl-4-(trifluoromethyl)isoxazol-5-yl)-1,2,4-oxadiazol-3-yl)chroman-3-yl)piperidin-3-yl)acetic acid, TFA salt (49); 2-(-1-((3R,4S)-4-hydroxy-7-(5-(3-phenyl-4-(trifluoromethyl)isoxazol-5-yl)-1,2,4-oxadiazol-3-yl)chroman-3-yl)piperidin-3-yl)acetic acid (50); 2-(-1-((3S,4R)-4-hydroxy-7-(5-(3-phenyl-4-(trifluoromethyl)isoxazol-5-yl)-1,2,4-oxadiazol-3-yl)chroman-3-yl)piperidin-3-yl)acetic acid, TFA salt (51); 2-(-1-((3S,4R)-4-hydroxy-7-(5-(3-phenyl-4-(trifluoromethyl)isoxazol-5-yl)-1,2,4-oxadiazol-3-yl)chroman-3-yl)piperidin-3-yl)acetic acid, TFA salt (52); 3-((3R,4S)-4-Hydroxy-7-(5-(3-phenyl-4-(trifluoromethyl)isoxazol-5-yl)-1,2,4-oxadiazol-3-yl)chroman-3-ylamino)propanoic acid, TFA salt (53); 3-((3S,4R)-4-hydroxy-7-(5-(3-phenyl-4-(trifluoromethyl)isoxazol-5-yl)-1,2,4-oxadiazol-3-yl)chroman-3-ylamino)propanoic acid, TFA salt (54); (1S,3S)-3-((3R,4S)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt (57); (1R,3S)-3-((3S,4R)-4-hydroxy-7-(5-(3-phenyl-4-(trifluoromethyl)isoxazol-5-yl)-1,2,4-oxadiazol-3-yl)chroman-3-ylamino)cyclohexanecarboxylic, TFA salt (58); (1R,3R)-3-((3S,4R)-4-hydroxy-7-(5-(3-phenyl-4-

(trifluoromethyl)isoxazol-5-yl)-1,2,4-oxadiazol-3-yl)
chroman-3-ylamino)cyclohexanecarboxylic acid, TFA salt
(59); (1R,3R)-3-((3S,4R)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid (60); (1S,4S)-4-((3R,4S)-4-hydroxy-7-(5-(3-phenyl-4-(trifluoromethyl)isoxazol-5-yl)-1,2,4-oxadiazol-3-yl)chroman-3-ylamino)
cyclohexanecarboxylic acid, TFA salt (61); (1R,4R)-4-((3R,4S)-4-hydroxy-7-(5-(3-phenyl-4-(trifluoromethyl)isoxazol-5-yl)-1,2,4-oxadiazol-3-yl)chroman-3-ylamino)
cyclohexanecarboxylic acid, TFA salt (62); (1R,3S)-3-((3S,4R)-4-hydroxy-7-(5-(3-phenyl-4-(trifluoromethyl)isoxazol-5-yl)-1,2,4-oxadiazol-3-yl)chroman-3-ylamino)
cyclohexanecarboxylic acid, TFA salt (63); (1S,3R)-3-((3R,4S)-4-hydroxy-7-(5-(3-phenyl-4-(trifluoromethyl)isoxazol-5-yl)-1,2,4-oxadiazol-3-yl)chroman-3-ylamino)
cyclohexanecarboxylic acid, TFA salt (64); (1R,3R)-3-((3R,4S)-4-hydroxy-7-(5-(3-phenyl-4-(trifluoromethyl)isoxazol-5-yl)-1,2,4-oxadiazol-3-yl)chroman-3-ylamino)
cyclohexanecarboxylic acid, TFA salt (65); (1R,3S)-3-((3R,4S)-4-hydroxy-7-(5-(3-phenyl-4-(trifluoromethyl)isoxazol-5-yl)-1,2,4-oxadiazol-3-yl)chroman-3-ylamino)
cyclohexanecarboxylic acid, TFA salt (66); 2-((3S,4R)-4-hydroxy-7-(5-(3-phenyl-4-(trifluoromethyl)isoxazol-5-yl)-1,2,4-oxadiazol-3-yl)chroman-3-ylamino)acetic acid, TFA salt (67); 2-((3R,4S)-4-hydroxy-7-(5-(3-phenyl-4-(trifluoromethyl)isoxazol-5-yl)-1,2,4-oxadiazol-3-yl)chroman-3-ylamino)acetic acid, TFA salt (68); 4-((3R,4S)-4-hydroxy-7-(5-(3-phenyl-4-(trifluoromethyl)isoxazol-5-yl)-1,2,4-oxadiazol-3-yl)chroman-3-ylamino)butanoic acid, TFA salt (69); and 4-((3S,4R)-4-hydroxy-7-(5-(3-phenyl-4-(trifluoromethyl)isoxazol-5-yl)-1,2,4-oxadiazol-3-yl)chroman-3-ylamino)butanoic acid, TFA salt (70).

The compounds of Formula (I) have GTPγS S1P$_1$ EC$_{50}$ values of 5 μM or less as measured by the S1P$_1$ Receptor GTPγS Binding Assay described herein below. Preferably, the compounds of Formula (I) have GTPγS S1P$_1$ EC$_{50}$ values in the range of 0.1 nM to 5 μM, and more preferably, in the range of from 0.1 nM to 1 μM. Other preferred compounds of Formula (I) have GTPγS S1P$_1$ EC$_{50}$ values in the range of from 0.1 nM to 100 nM.

The compounds of Formula (I) are selective for S1P$_1$ activity over S1P$_3$ activity as measured by the selectivity ratio of the GTPγS S1P$_3$ EC$_{50}$ value to the GTPγS S1P$_1$ EC$_{50}$ value. The S1P$_1$ Receptor GTPγS Binding Assay and the S1P$_3$ Binding Assay are described herein below. The compounds of Formula (I) have selectivity ratios (GTPγS S1P$_3$/S1P$_1$) of at least 3.5 or greater, preferably at least 50 or greater, and more preferably at least 100 or greater. For example, suitable compounds of Formula (I) can have selectivity ratios in the range of from 50 to 50,000. Other suitable compounds of Formula (I) can have selectivity ratios in the range of from 100 to 50,000.

In one embodiment, the compounds of Formula (I) are provided having GTPγS S1P$_1$ EC$_{50}$ values in the range of from 0.1 nM to 100 nM and selectivity ratios (GTPγS S1P$_3$/S1P$_1$) of at least 50, and more preferably, at least 100.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$alkyl" denotes straight and branched chain alkyl groups with one to six carbon atoms.

As used herein, "alkylene" refers to a bivalent alkyl radical having the general formula —$(CH_2)_n$—, where n is 1 to 10. Non-limiting examples include methylene, dimethylene, trimethylene, tetramethylene, pentamethylene, and hexamethylene. For example, "$C_{1-6}$alkylene" denotes straight and branched chain alkylene groups with one to six carbon atoms. Further, for example, "$C_{0-4}$alkylene" denotes a bond and straight and branched chain alkylene groups with one to four carbon atoms.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—$CH_2Cl$), trifluoromethyl (—$CF_3$), and 2,2,2-trifluoroethyl (—$CH_2CF_3$). When numbers appear in a subscript after the symbol "C", the subscript defines with more specificity the number of carbon atoms that a particular haloalkyl group may contain. For example, "$C_{1-4}$haloalkyl" denotes straight and branched chain haloalkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "chloroalkyl" as used herein is intended to include both branched and straight-chain saturated aliphatic hydrocarbon groups substituted with one or more chlorine atoms. For example, "$C_{1-4}$ chloroalkyl" is intended to include $C_1$, $C_2$, $C_3$, and $C_4$ alkyl groups substituted with one or more chlorine atoms. Representative examples of chloroalkyl groups include, but are not limited to, —$CCl_3$ and —$CH_2CCl_3$.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$hydroxyalkyl.

The term "cyano" refers to the group —CN.

The term "cyanoalkyl" includes both branched and straight-chain saturated alkyl groups substituted with one or more cyano groups. For example, "cyanoalkyl" includes —$CH_2CN$, —$CH_2CH_2CN$, —$C(CH_3)_2CN$, and $C_{1-4}$cyanoalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$).

For example, "$C_{1-4}$alkoxy" is intended to include $C_1$, $C_2$, $C_3$, and $C_4$ alkoxy groups.

"Fluoroalkoxy" and "—O(fluoroalkyl)" represent a fluoroalkyl group as defined above attached through an oxygen linkage (—O—). For example, "$C_{1-4}$fluoroalkoxy" is intended to include $C_1$, $C_2$, $C_3$, and $C_4$ fluoroalkoxy groups.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, and indanyl.

The term "benzyl", as used herein, refers to a methyl group in which one of the hydrogen atoms is replaced by a phenyl group.

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl. Exemplary bicyclic heterocyclo groups include quinuclidinyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Edition, p. 1418, Mack Publishing Company, Easton, Pa. (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes esters and carbonates formed by reacting one or more hydroxyls of compounds of Formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist to S1P1, or effective to treat or prevent vascular disease or autoimmune diseases.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.5 to 2000 mg, preferably from about 0.5 to 500 mg, more preferably from about 0.5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 1500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

UTILITY

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease. Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds that act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to S1P1 refers to an agent which exerts pharmacological effects such as decreased motility of T cells, decreased trafficking of T cells, or decreased egress of T cells from lymphoid tissues. (Rosen et al., *Trends in Immunology,* 28:102 (2007)).

By virtue of their S1P1 activity as agonists, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, psoriatic arthritis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, neuropathic pain, and chronic bacterial infection.

One embodiment provides a method for treating autoimmune and/or inflammatory diseases, comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of autoimmune and/or inflammatory diseases. In another embodiment, provided is the use of the compounds of Formula (I) or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs. The method of the present embodiment includes administration of a therapeutically effect amount of a compound of Formula (I) or a pharmaceutically effective salt thereof.

In another embodiment, a method for treating vascular disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of vascular disease. In another embodiment, provided is the use of the compounds of Formula (I) or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis and ischemia reperfusion injury.

The methods of treating $S1P_1$-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to act as an agonist at the $S1P_1$ receptor. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo[1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), belatacept, or their ligands including CD154 (GP39, or CD40L); antibodies to, fusion proteins, or soluble receptors of human cytokines or growth factors, for example, TNF such as, infliximab (REMICADE®), etanercept (Embrel), adalimumab (HUMIRA®), LT, Il-1 such as anakinra (KINERET®) (an IL-1 receptor antagonist), IL-2, IL-4, IL-5, Il-6, such as CNTO 328 (a chimeric anti-IL-6 antibody), Il-7, Il-8, Il-12, Il-15, Il-16, Il-17, Il-21, Il-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal anti-inflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenololate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicillamine, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds.

METHODS OF PREPARATION

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, 3rd Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

As shown in Scheme 1, compounds of Formula I may be produced, starting with the commercially available ketones 1.1, 1.2, and 1.3. For example, the ketones 1.1-1.3 may be brominated via N-bromosuccinimide/p-toluenesulfonic acid with heating, or in a two step procedure, featuring lithium bis(trimethylsilyl)amide followed by N-bromosuccinimide. The resulting bromo compounds 1.4-1.6 may be converted to the azido compounds 1.7-1.9 via the action of sodium azide. These azido compounds 1.7-1.9 may be treated with various reducing agents (for example, sodium borohydride) to give the alcohols 1.10-1.12. The alcohols 1.10-1.12 may be reacted with hydroxylamine or its salts to give the N'-hydroxybenzimidamides 1.13-1.15. These N'-hydroxybenzimidamides 1.13-1.15 may be treated with various acyl derivatives 1.16 (for example, the acid fluoride) to afford the oxadiazole compounds 1.17-1.19. These compounds 1.17-1.19 may be converted to compounds of Formula I, for example 1.20-1.22, via simple reduction (for example with SnCl$_2$).

Scheme 1

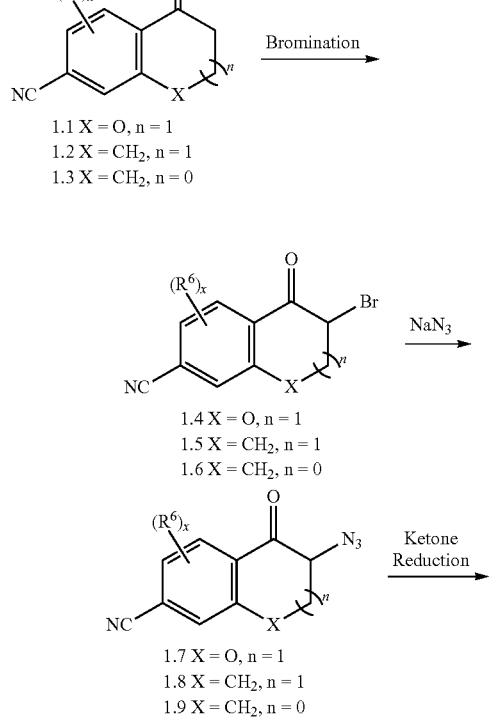

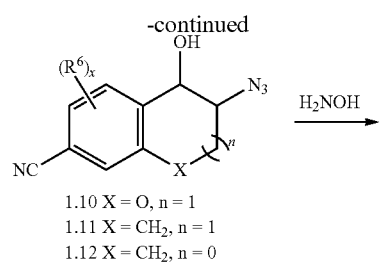

1.10 X = O, n = 1
1.11 X = CH$_2$, n = 1
1.12 X = CH$_2$, n = 0

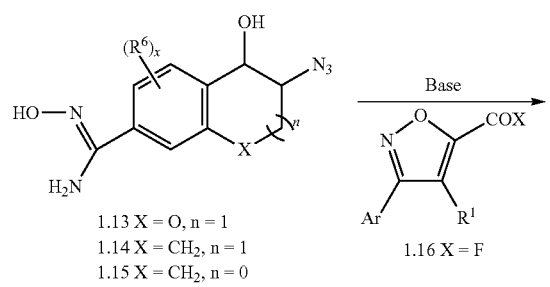

1.13 X = O, n = 1
1.14 X = CH$_2$, n = 1
1.15 X = CH$_2$, n = 0

1.16 X = F

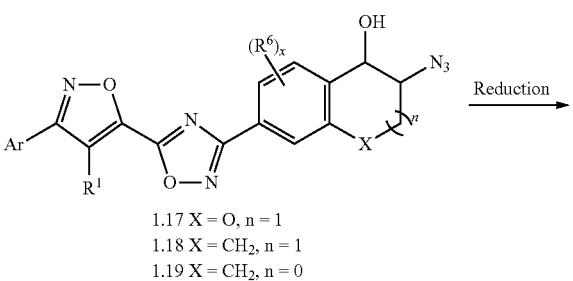

1.17 X = O, n = 1
1.18 X = CH$_2$, n = 1
1.19 X = CH$_2$, n = 0

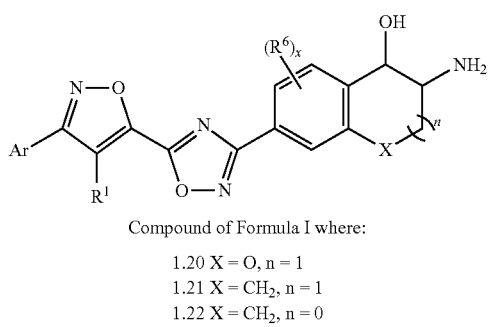

Compound of Formula I where:
1.20 X = O, n = 1
1.21 X = CH$_2$, n = 1
1.22 X = CH$_2$, n = 0

As shown in Scheme 2, compounds of Formula (I) may also be prepared via transformations starting with compounds 1.20-1.22. These compounds 1.20-1.22 may be treated with an aldehyde or ketone in a reductive amination reaction to give compounds of Formula I, compounds 2.1-2.3. Another reductive amination may be performed on compounds 2.1-2.3 to give additional compounds of Formula I, compounds 2.4-2.6. Compounds 1.20-1.22 may also be treated with a dialdehyde (for example 2.7) in a reductive amination reaction to give compounds of Formula I, compounds 2.8-2.10. Furthermore, compounds 1.20-1.22 may be used in a Michael reaction (for example, with methyl acrylate) to give compounds 2.11-2.13, which are compounds of Formula I. Compounds 2.11-2.13 may be converted to the carboxylates 2.14-1.16 (also compounds of Formula I) via simple hydrolysis (for example, either LiOH or HCl treatment).

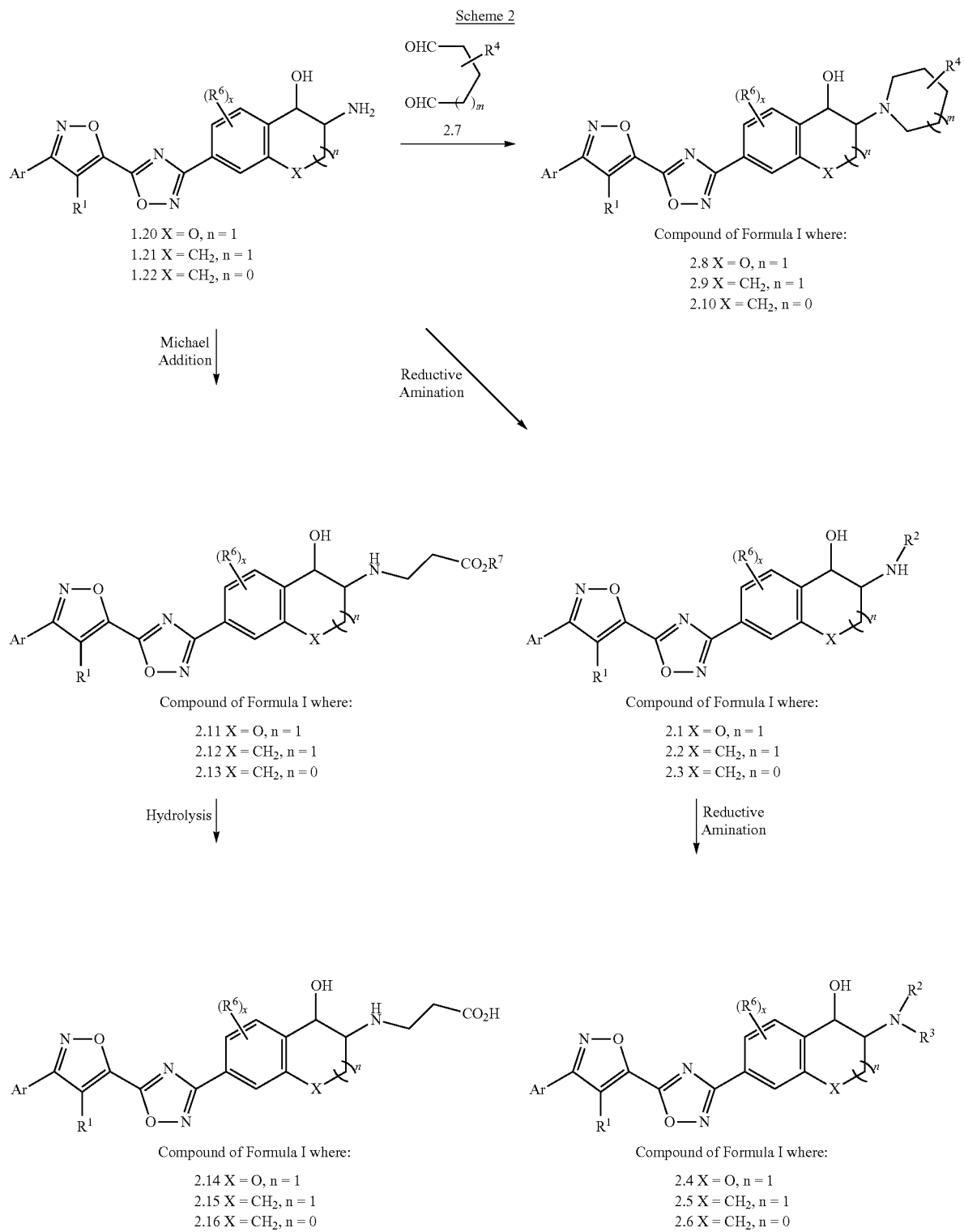

As shown in Scheme 3, compounds of Formula (I) may also be prepared from the previously described compounds 1.17-1.19. Hence, compounds 1.17-1.19 may be protected (for example, as the TBS ether via treatment with tert-butyldimethylsilyl trifluoromethanesulfonate and 2,6-lutidine) at the alcohol position to give compounds 3.1-3.3 ($R^5$=TBS). These compounds 3.1-3.3 may be converted to the amines (for example, a reduction with $SnCl_2$) and then alkylated (for example with tert-butyl 2-bromoacetate and $K_2CO_3$) to give compounds 3.4-3.6. Next, compounds 3.4-3.6 may be deprotected (for example with an acid like HCl) to give compounds 3.7-3.9, which are compounds of Formula I.

Scheme 3

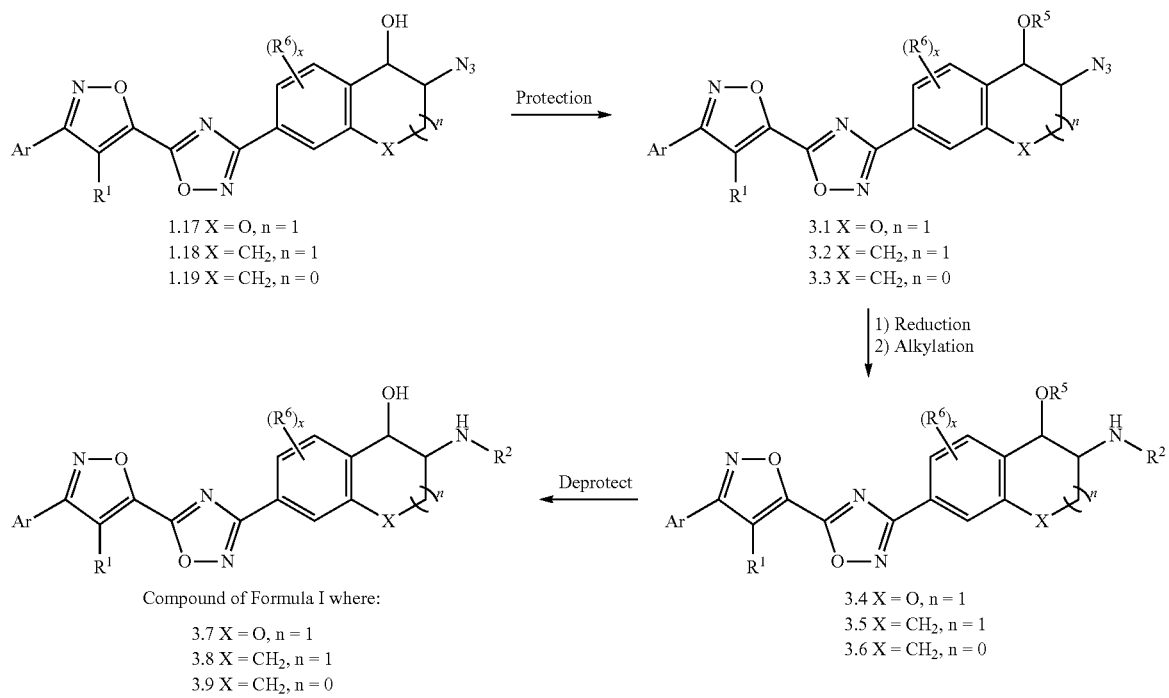

Compound of Formula I where:
3.7 X = O, n = 1
3.8 X = CH$_2$, n = 1
3.9 X = CH$_2$, n = 0

ABBREVIATIONS

AcOH acetic acid
BOC t-butyl carbamate
BOP benzotriazol-1-yloxytris(trimethylamino)phosphonium hexafluorophosphate
BOP-Cl bis-(2-oxo-3-oxazolidinyl)phosphinic chloride
DBU 1,8-diazabicyclo[5.4.0]undec-7-ene
DCE dichloroethane
DCM dichloromethane
DIEA diisopropylethylamine
DMF dimethylformamide
DMSO dimethyl sulfoxide
EDC 1-(3-dimethylaminopropyl)-3-ethylcarbodiimide hydrochloride
EtOAc ethyl acetate
h or hr hour(s)
HCl hydrochloric acid
HOBt hydroxybenzotriazole
HPLC high pressure liquid chromatography
HMPA hexamethylphosphorus triamide
hr hour(s)
IPA isopropyl alcohol
i-PrOH isopropyl alcohol
LC/MS liquid chromatography/mass spectroscopy
m-CPBA 3-chloroperbenzoic acid
MeCN acetonitrile
MeOH methanol
min minute(s)
MPLC medium pressure liquid chromatography
MS mass spectroscopy
NaOH sodium hydroxide
NMR nuclear magnetic resonance
Pd$_2$(dba)$_3$ tris-(dibenzylideneacetone)dipalladium
rt room temperature
SEM trimethylsilyloxyethoxymethyl
TBAF tetrabutylammonium fluoride
TEA triethylamine
TEMPO 2,2,6,6-tetramethylpiperidine 1-oxyl
TFA trifluoroacetic acid
THF tetrahydrofuran
TMS-Cl chlorotrimethylsilane

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein, but rather is defined by the claims appended hereto.

Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially using Roman numerals (e.g., Intermediate I, Intermediate II, etc.) and are abbreviated as Int-1, Int-2, etc. In some instances the preparation of common intermediates may require multiple steps to be prepared. Each step is identified by the common intermediate and the step, e.g., Int-1-A, Int-1-B, and so forth. Compounds of the Examples are identified by the example and step in which they were prepared (e.g., "1-A" or "Preparation 1A" denotes the Example 1, step A) or by the example only where the compound is the title compound of the example (for example, "1"

denotes the title compound of Example 1). In some instances alternate preparations of intermediates or Examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, decreased number of linear steps, etc. The intent of describing alternative preparations is to further enable the preparation of the Examples of this invention.

Those experiments which specify that they were performed in a microwave were conducted in a SmithSynthesizer manufactured by Personal Chemistry or a DISCOVER® microwave manufactured by CEM corporation. The microwave ovens generate a temperature which can be selected to be between 60-250° C. The microwaves automatically monitor the pressure which is between 0-300 PSI. Reaction hold times and temperature set points are reported.

Silica gel purification was performed on an Isco Companion medium pressure liquid chromatography instrument using prepacked silica gel cartridges REDI-SEP® from Isco (12 g, 24 g, 40 g, 80 g, 120 g, 220, 330 g appropriate to the scale of the purification) using solvent gradients described for each Example but in most cases, 0-100% EtOAc in hexanes (or 25-100%) over 25 minutes.

Retention time data reported for each example uses one of the three following General Analytical HPLC methods. All products were run using Method A unless otherwise indicated:

Method A: Column: Waters Sunfire C18, 3.5-μm particles (3.0×150 mm); 10-100% B gradient over 12 min, then a 3-minute hold at 100% B. Mobile Phase A=0.05% TFA in $CH_3CN$:Water (10:90), Mobile Phase B=0.1% TFA in $CH_3CN$:Water (90:10); Flow Rate=0.5 ml/min; uv detection 220 nM.

Method B: Column: Xbridge Phenyl C18, 3.5-μm particles (3.0×150 mm); 10-100% B gradient over 12 min, then a 3-minute hold at 100% B. Mobile Phase A=0.05% TFA in $CH_3CN$:Water (10:90), Mobile Phase B=0.1% TFA in $CH_3CN$:Water (90:10); Flow Rate=0.5 ml/min; uv detection 220 nM.

Method C: Identical to Method A with uv detection 254 nM.

Method D: Identical to Method B with uv detection 254 nM.

Method E: Column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 35° C.; Gradient: 0-100% B over 4 minutes, then a 1 min hold at 100% B; flow rate=4 mL/min; uv detection 220 nM.

Preparative HPLC methods use one of the following methods unless otherwise noted in the specific example. Method 1: Column: PHENOMENEX® Luna C18, 5-μm particles (21.2×250 mm) or otherwise stated, Guard Column: none; Mobile Phase A: 90% water with 10% MeOH and 0.1% TFA; Mobile Phase B: 90% MeOH with 10% water and 0.1% TFA; Gradient: 0-100% B over 30 minutes; Flow rate: 15 mL/min, uv detection 220 nM. Method 2: Column: PHENOMENEX® Luna C18, 5-μm particles (21.2×250 mm; Guard Column: none; Mobile Phase A: 5:95 acetonitrile:water with 0.1% TFA; Mobile Phase B: 95:5 acetonitrile:water with 0.1% TFA; Gradient: 0-100% B over 30 minutes; Flow: 20 mL/min, uv detection 220 nM.

Intermediate 1

3-Phenyl-4-(trifluoromethyl)isoxazole-5-carboxylic acid

(Int-1)

Int-1-A: 4,4,4-Trifluorobut-2-yn-1-ol

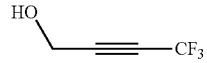

(Int-1-A)

To a solution of diisopropylamine (24.7 mL, 176 mmol) in ether (100 mL) at −78° C. was added a 10M solution of butyllithium in ether (17.6 mL, 176 mmol) over 5 min. After 10 min. at −78° C., 2-bromo-3,3,3-trifluoroprop-1-ene (14.0 g, 80 mmol) was added to the pale yellow solution. After an additional 10 min., paraformaldehyde (2.40 g, 80 mmol) was added, the dry-ice bath was removed, and the reaction mixture was stirred at room temperature overnight. As the reaction mixture approached room temperature, it became dark in color. The reaction was quenched with a 1N aqueous solution of hydrochloric acid (100 mL), diluted with ether (500 mL), washed with a 1N aqueous solution of hydrochloric acid (2×100 mL), washed with brine 100 mL, and dried over anhydrous sodium sulfate. Concentration under reduced pressure afforded a dark liquid which was distilled under low vacuum (~50 Torr, ~50° C.) to give 4,4,4-trifluorobut-2-yn-1-ol (7.1 g, 57.2 mmol, 72% yield) as a pale yellow liquid. $^1$H NMR (500 MHz, $CDCl_3$) δ ppm 2.31 (br. s., 1H) and 4.38-4.42 (m, 2H).

Alternate Preparation of Int-1-A:

To an ether (pre-dried over magnesium sulfate) solution of phenanthroline (2.16 mg, 0.012 mmol) (indicator) at −78° C. under nitrogen was added a 2M solution of n-butyl lithium in pentane. An orange color immediately appeared. Trifluoromethylacetylene gas was bubbled through the solution at −78° C. After ~4 min. of gas introduction, the orange color almost completely disappeared, the reaction mixture became cloudy and a pale light orange color persisted. Paraformaldehyde was added, and the dry ice/isopropanol bath was removed after 5 min. and replaced with a 0° C. ice-bath. Stirring was continued for 45 min. The ice bath was removed and stirring was continued for an additional 1.25 h. The reaction flask was immersed in a 0° C. ice bath, and a saturated aqueous solution of ammonium chloride (20.0 mL) was added. The layers were separated, and the organic layer was washed with water (2×), washed with brine, and dried over anhydrous sodium sulfate. Concentration under low-vacuum (~50 Torr) without heat afforded a dark brown liquid which was purified by vacuum distillation (~50 Torr, ~50° C.) to give 4,4,4-trifluorobut-2-yn-1-ol (7.1 g, 57.2 mmol, 72% yield) as a colorless liquid.

Int-1-B: N-Hydroxybenzimidoyl chloride

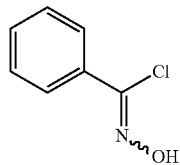

(Int-1-B)

This compound was prepared according to the method of Liu, K. C. et al., *J. Org. Chem.*, 45:3916-1918 (1980).

To a colorless, homogeneous solution of (E)-benzaldehyde oxime (24.4 g, 201 mmol) in N,N-dimethylformamide (60 mL) at room temperature was added N-chlorosuccinimide (26.9 g, 201 mmol) portion-wise over 30 min. During each addition, the reaction mixture became yellow and then gradually returned to near colorlessness. Additionally, an exotherm was noted with each portion added. (It was extremely important to make sure the reaction initiates after the addition of the first ~⅕ of the NCS; an ice-bath was readily available.) After the addition was complete, the homogeneous reaction mixture was stirred overnight at room temperature. The reaction mixture was diluted with 250 mL of water and extracted with ether (3×100 mL). The organic layers were combined, washed with water (2×100 mL), washed with a 10% aqueous solution of lithium chloride (2×100 mL), and washed with brine (100 mL). The aqueous layers were back extracted with ether (100 mL), and the combined organic layers (400 mL) were dried over anhydrous sodium sulfate. Concentration under reduced pressure afforded (Z)—N-hydroxybenzimidoyl chloride (30.84 g, 198 mmol, 98% yield) as a fluffy, pale yellow solid. The product had an HPLC ret. time=1.57 min.—Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS M+1=155.8. $^1$H NMR (500 MHz, DMSO-$d_6$) δ ppm 7.30-7.64 (m, 3H), 7.73-7.87 (m, 2H), and 12.42 (s, 1H).

Int-1-C: 3-Phenyl-4-(trifluoromethyl)isoxazol-5-yl)methanol

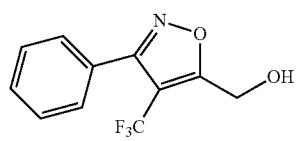

(Int-1-C)

To a pale yellow, homogeneous mixture of N-hydroxybenzimidoyl chloride (5.50 g, 35.4 mmol) and 4,4,4-trifluorobut-2-yn-1-ol (5.46 g, 39.6 mmol) in dichloroethane (85 mL) in a 250 mL round bottom flask at 70° C. was added triethylamine (9.85 mL, 70.7 mmol) in 22 mL of dichloroethane over 2.5 h via an addition funnel (the first ~50% over 2 h and the remaining 50% over 0.5 h). After the addition was complete, the reaction mixture was complete by HPLC (total time at 70° C. was 3 h). The reaction mixture was stirred at room temperature overnight.

The reaction mixture was diluted with dichloromethane (100 mL), washed with water (100 mL), and the organic layer was collected. The aqueous layer was extracted with dichloromethane (2×50 mL), and the combined organic layers were dried over anhydrous sodium sulfate. The solvent was removed under reduced pressure. Analysis indicated that the product mixture was composed of a 86:14 mixture of the desired regioisomer (Int-1-C), (3-phenyl-4-(trifluoromethyl)isoxazol-5-yl)methanol, and the undesired regioisomer, (3-phenyl-5-(trifluoromethyl)isoxazol-4-yl)methanol. The mixture was purified by silica gel chromatography using a mixture of ethyl acetate and hexane (1% to pack and load-5%-9%-12%) to afford (3-phenyl-4-(trifluoromethyl)isoxazol-5-yl)methanol (5.34 g, 21.96 mmol, 62.1% yield) as a pale yellow oil. The compound had an HPLC ret. time=1.91 min.—Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS M+1=244.2. $^1$H NMR (500 MHz, $CDCl_3$) δ ppm 2.21 (br. s., 1H), 4.97 (s, 2H), 7.47-7.56 (m, 3H), and 7.65 (d, J=6.60 Hz, 2H).

Int-1: 3-Phenyl-4-(trifluoromethyl)isoxazole-5-carboxylic acid

Preparation of Jones' Reagent

To an orange, homogeneous solution of chromium trioxide (12.4 g, 0.123 mol) in water (88.4 mL) at 0° C. was added sulfuric acid (10.8 mL) dropwise via addition funnel over 30 min. with stirring. The addition funnel was rinsed with water (1 mL) to give 1.23 M solution of Jones' Reagent (0.123 mol of reagent in 100 mL of solvent).

To a solution of (3-phenyl-4-(trifluoromethyl)isoxazol-5-yl)methanol (5.24 g, 21.6 mmol) in acetone (75 mL) at room temperature (immersed in a water bath) was added Jones' Reagent (43.8 mL, 53.9 mmol) via addition funnel slowly over 1.5 h. The dark reaction mixture was stirred at room temperature overnight. By HPLC, the reaction was 93% complete. An additional 0.5 equivalents (9 mL) of the Jones' Reagent was added. After 1 h, the reaction was 95% complete. After an additional 3 h, the reaction was 96% complete. An additional 0.5 equivalents (9 mL) of the Jones' Reagent was added. The reaction mixture was stirred for an additional 2.5 h. By HPLC, the reaction was 97% complete. Isopropyl alcohol (6 mL) was added, and the mixture was stirred for 90 min, resulting in a dark green precipitate. The mixture was diluted with ether (600 mL), washed with a 2% aqueous solution of sodium hydrogen sulfite (5×100 mL), and the organic layer was collected. The aqueous layer was back-extracted with ether (2×100 mL). By HPLC, there was no additional product in the aqueous layer. The combined organic layers were washed with water (100 mL), washed with a saturated aqueous solution of brine (100 mL), and dried over anhydrous sodium sulfate. The aqueous layer was back-extracted with ether (100 mL), and the organic layer was added to the previous organic layers. The solution was concentration under reduced pressure to give 3-phenyl-4-(trifluoromethyl)isoxazole-5-carboxylic acid as an off-white solid. The solid was diluted with dichloromethane (200 mL), washed with a 2% aqueous solution of sodium hydrogen sulfite, washed with brine, and dried over anhydrous sodium sulfate. Concentration under reduced pressure afforded 3-phenyl-4-(trifluoromethyl)isoxazole-5-carboxylic acid (3.84 g, 14.93 mmol, 69.3% yield) as a pale yellow solid. The product was 96% pure by HPLC with a ret. time=1.60 min.—Column: CHROMOLITH® SpeedROD 4.6×50 mm (4 min.); Solvent A=10%

MeOH, 90% H₂O, 0.1% TFA; Solvent B=90% MeOH, 10% H₂O, 0.1% TFA. LC/MS M+1=258.2.

The sodium hydrogen sulfite aqueous layer still contained a significant amount of product. The brine layer contained no additional product and was discarded. The aqueous layer was saturated with sodium chloride, the pH was adjusted to ~3.5, and the solution was extracted with ether (3×100 mL). The organic layer was dried over anhydrous sodium sulfate and concentrated to afford additional 3-phenyl-4-(trifluoromethyl)isoxazole-5-carboxylic acid (1.12 g, 4.36 mmol, 20.21% yield) as a white solid. The product was >99% pure by HPLC with a ret. time=1.60 min.—Column: CHROMOLITH® SpeedROD 4.6×50 mm (4 min.); Solvent A=10% MeOH, 90% H₂O, 0.1% TFA; Solvent B=90% MeOH, 10% H₂O, 0.1% TFA. LC/MS M+1=258.1. $^1$H NMR (500 MHz, DMSO-d$_6$) δ ppm 7.55-7.63 (m, 5H).

The products were combined to give 4.96 g (90% yield) of 3-phenyl-4-(trifluoromethyl)isoxazole-5-carboxylic acid.

Alternate Preparation of Int-1

A mixture of (3-phenyl-4-(trifluoromethyl)isoxazol-5-yl)methanol (2.1 g, 8.64 mmol), TEMPO (0.094 g, 0.604 mmol), and a sodium phosphate buffer (0.67M) (32.2 mL, 21.59 mmol) in acetonitrile (30 mL) was heated to 35° C. A fresh solution of sodium phosphate buffer (40 mL, pH ~6.5) consisting of a 1:1 solution of NaH₂PO₄ (20 mL, 0.67M) and Na₂HPO₄ (20 mL, 0.67M) was prepared and used. Solutions of sodium chlorite (3.91 g, 34.5 mmol) in water (4.5 mL) and bleach (4.3 mL, 6% wt.) were added simultaneously over 40 min. The reaction was monitored by HPLC, and after 2 h, ~30% of the starting material remained. After 6 h, 10% remained. Additional bleach (100 µL) was added, and the reaction mixture was left at room temperature overnight. Additional bleach (100 µL) was added. The resulting mixture was allowed to stir at 35° C. for additional 2 h. HPLC indicated complete conversion. The reaction was quenched by the slow addition of a solution of sodium sulfite (2.07 mL, 43.2 mmol) in water (90 mL) at 0° C., resulting in the disappearance of the brown reaction color. The solvent was removed under reduced pressure, and the remaining aqueous residue was extracted with ethyl acetate (3×40 mL). The organic layers were combined, washed with water (8 mL), washed with brine (8 mL), and dried over anhydrous sodium sulfate. Concentration under reduced pressure afforded 3-phenyl-4-(trifluoromethyl)isoxazole-5-carboxylic acid (2.2 g, 8.55 mmol, 99% yield) as a pale yellow solid.

Alternate Preparation of 3-Ohenyl-4-(trifluoromethyl)isoxazole-5-carboxylic acid Preparation Int-1-D: Ethyl 3-phenyl-4-(trifluoromethyl)isoxazole-5-carboxylate

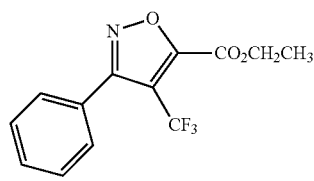

(Int-1-D)

To a pale yellow mixture of (Z)—N-hydroxybenzimidoyl chloride (1.04 g, 6.68 mmol) and ethyl 4,4,4-trifluorobut-2-ynoate (1.238 g, 7.45 mmol) in diethyl ether (20 mL) at room temperature was added triethylamine (1.86 mL, 13.4 mmol) over 15 min., resulting in a precipitant. After the addition was complete, the pale yellow slurry was stirred at room temperature over the weekend. The heterogeneous reaction mixture was filtered under reduced pressure to remove the triethylamine hydrochloride salt, and the filtrate was concentrated to give the product mixture as a dark yellow, viscous oil (2.03 g). By HPLC, the reaction mixture was composed of a mixture of the desired regioisomer, ethyl 3-phenyl-4-(trifluoromethyl)isoxazole-5-carboxylate, and the undesired regioisomer, ethyl 3-phenyl-5-(trifluoromethyl)isoxazole-4-carboxylate, in an approximately 15:85 ratio. The compound mixture was dissolved in hexane and sonicated for 5 min. The hexane was decanted off, and the dark red, oily residue was found to have only trace product by HPLC. The hexane was removed under reduced pressure, and the residue (1.89 g) was purified by preparative HPLC. The desired fractions containing ethyl 3-phenyl-4-(trifluoromethyl)isoxazole-5-carboxylate were concentrated, and the residue was diluted with dichloromethane, washed with a saturated aqueous solution of sodium bicarbonate, and dried over anhydrous sodium sulfate. Concentration under reduced pressure afforded ethyl 3-phenyl-4-(trifluoromethyl)isoxazole-5-carboxylate (0.087 g, 0.305 mmol, 4.6% yield) as a pale yellow solid. The compound had an HPLC ret. time=2.88 min.—Column: CHROMOLITH® SpeedROD 4.6×50 mm (4 min.); Solvent A=10% MeOH, 90% H₂O, 0.1% TFA; Solvent B=90% MeOH, 10% H₂O, 0.1% TFA. $^1$H NMR (400 MHz, CDCl₃) δ ppm 1.46 (t, J=7.15 Hz, 3H), 4.53 (q, J=7.03 Hz, 2H), 7.48-7.55 (m, 3H), and 7.58 (d, J=7.53 Hz, 2H).

An Alternate Preparation of Int-1-D: Ethyl 3-phenyl-4-(trifluoromethyl)isoxazole-5-carboxylic acid starting with ethyl 4,4,4-trifluorobut-2-enoate Preparation of Int-1-E: Ethyl 2,3-dibromo-4,4,4-trifluorobutanoate

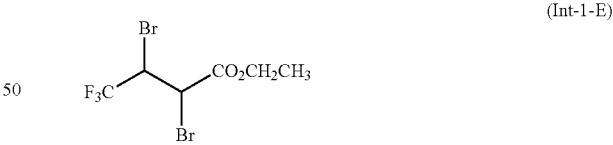

(Int-1-E)

Bromine (18.4 mL, 357 mmol) was added dropwise over 30 minutes to a solution of (E)-ethyl 4,4,4-trifluorobut-2-enoate (50 g, 297 mmol) in carbon tetrachloride (50 mL) at room temperature under nitrogen. The resulting dark red solution was refluxed for 4 hours. Additional bromine (2 ml) was added and heating was continued until the HPLC analysis showed that the starting material had been consumed. The reaction mixture was concentrated under reduced pressure to give light brown oil. HPLC (XBridge 5µ C18 4.6×50 mm, 4 mL/min, solvent A: 10% MeOH/water with 0.2% H₃PO₄, solvent B: 90% MeOH/water with 0.2% $H_3PO_4$, gradient with 0-100% B over 4 minutes): 2.96 and 3.19 minutes.

Int-1-F (Z/E): Ethyl 2-bromo-4,4,4-trifluorobut-2-enoate

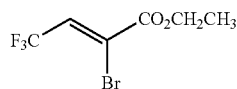

(Int-1-F)

To a solution of ethyl 2,3-dibromo-4,4,4-trifluorobutanoate (Int-1-E) in hexane (200 mL) cooled to 0° C. was added triethylamine (49.7 ml, 357 mmol) drop-wise over 35 minutes, during which time a white precipitate formed. The reaction mixture was stirred for an additional 2 hours until LC indicated complete conversion. The solid was filtered and rinsed with hexane (3×50 mL), and the filtrate was concentrated and passed through a short silica gel pad eluting with 10% ethyl acetate/hexane to give (Z/E)-ethyl 2-bromo-4,4,4-trifluorobut-2-enoate (65.5 g, 265 mmol, 89% yield for two steps) as a colorless oil. Alternatively, the crude product can be purified by distillation (85° C./~60 mmHg). $^1$H NMR (CDCl$_3$, 400 MHz) δ 7.41 (q, 1H, J=7.28 Hz), 4.35 (q, 2H, J=7.11 Hz), 1.38 (t, 3H, J=7.15 Hz); HPLC (XBridge 5µ C18 4.6×50 mm, 4 mL/min, solvent A: 10% MeOH/water with 0.2% $H_3PO_4$, solvent B: 90% MeOH/water with 0.2% $H_3PO_4$, gradient with 0-100% B over 4 minutes): 3.09 minutes.

Alternate preparation of Int-1-D: Ethyl 3-phenyl-4-(trifluoromethyl)isoxazole-5-carboxylate

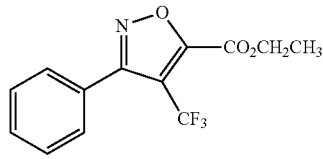

(Int-1-D)

(Z/E)-Ethyl 2-bromo-4,4,4-trifluorobut-2-enoate, Int-1-F, (39.7 g, 161 mmol) and N-hydroxybenzimidoyl chloride (30 g, 193 mmol) were dissolved in ethyl acetate (150 mL). Indium (III) chloride (8.89 g, 40.2 mmol) was added and the resulting mixture stirred for 60 minutes at room temperature under $N_2$. Potassium hydrogen carbonate (32.2 g, 321 mmol) was added to the reaction mixture which was allowed to stir overnight for 14 hours at room temperature. The solvent was removed in vacuo. The residue was re-suspended in 300 mL hexane, stirred for 10 minutes, and then filtered. The filter cake was washed with hexane (3×30 mL) and the combined filtrate was concentrated in vacuo to give crude product, which was further purified with flash chromatography to generate 33 g product (72%) as light yellowish oil as a mixture of the desired isomer Int-1-D and undesired isomer ethyl 3-phenyl-5-(trifluoromethyl)isoxazole-4-carboxylate in a ratio of ~30/1. MS m/e 286.06 (M+H$^+$); $^1$H NMR (CDCl$_3$, 400 MHz) δ 7.56 (m, 5H), 4.53 (q, 2H, J=7.3 Hz), 1.46 (t, 3H, J=7.2 Hz); HPLC (XBridge 5µ C18 4.6×50 mm, 4 mL/min, Solvent A: 10% MeOH/water with 0.2% $H_3PO_4$, Solvent B: 90% MeOH/water with 0.2% $H_3PO_4$, gradient with 0-100% B over 4 minutes): 3.57 minutes.

Preparation of Int-1 Li Salt: 3-Phenyl-4-(trifluoromethyl)isoxazole-5-carboxylic acid, Lithium Salt

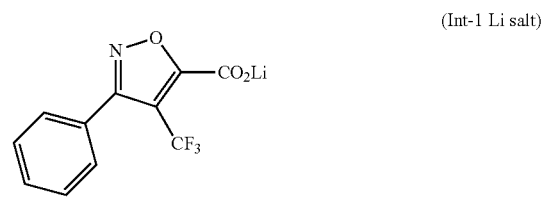

(Int-1 Li salt)

A mixture of ethyl 3-phenyl-4-(trifluoromethyl)isoxazole-5-carboxylate, Int-1-D, (0.085 g, 0.298 mmol) and lithium hydroxide hydrate (0.013 g, 0.298 mmol) in methanol (2.0 mL) and water (1.0 mL) was stirred at room temperature overnight. The reaction mixture was concentrated to dryness to give 3-phenyl-4-(trifluoromethyl)isoxazole-5-carboxylic acid, lithium salt (0.079 g, 0.299 mmol, 100% yield) as a pale yellow solid. The compound had an HPLC ret. time=1.72 min.—Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS M+1=258.0. $^1$H NMR (400 MHz, CDCl$_3$) δ ppm 7.49-7.57 (m, 3H) and 7.58-7.62 (m, 2H).

Int-1-G: 3-Phenyl-4-(trifluoromethyl)isoxazole-5-carbonyl fluoride

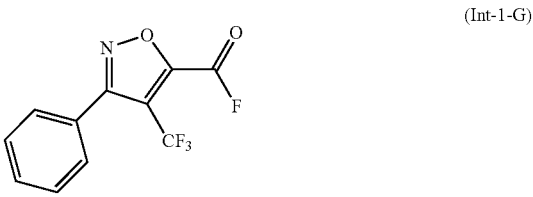 [SMILES: O=C(F)c1onc(-c2ccccc2)c1C(F)(F)F]

(Int-1-G)

To a mixture of 3-phenyl-4-(trifluoromethyl)isoxazole-5-carboxylic acid (3.00 g, 11.7 mmol) and pyridine (1.132 mL, 14.0 mmol) in dichloromethane (100 mL) at room temperature was added 2,4,6-trifluoro-1,3,5-triazine (cyanuric fluoride) (1.18 mL, 14.0 mmol). The reaction mixture was stirred at room temperature overnight, diluted with dichloromethane (300 mL), washed with an ice-cold solution of 0.5N aqueous hydrochloric acid (2×100 mL), and the organic layer was collected. The aqueous layer was back-extracted with dichloromethane (200 mL), and the combined organic layers were dried anhydrous sodium sulfate and concentrated to afford 3-phenyl-4-(trifluoromethyl)isoxazole-5-carbonyl fluoride (2.91 g, 11.2 mmol, 96% yield) as a yellow, viscous oil. The product was found to react readily with methanol and on analysis was characterized as the methyl ester, which had an HPLC ret. time=2.56 min.—Column: CHROMOLITH® SpeedROD 4.6×50 mm (4 min.); Solvent A=10% MeOH, 90% H₂O, 0.1% TFA; Solvent B=90% MeOH, 10% H₂O, 0.1% TFA. LC/MS M+1=272.3 (methyl ester).

Intermediate 2

Racemic (3R*,4S*)-3-azido-7-(5-(3-phenyl-4-(trifluoromethyl)isoxazol-5-yl)-1,2,4-oxadiazol-3-yl)chroman-4-ol

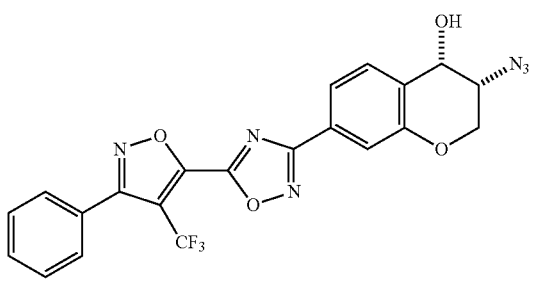
(Int-2)

Int-2-A: Racemic 3-bromo-4-oxochroman-7-carbonitrile

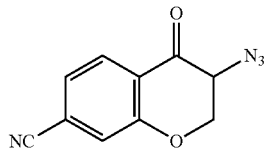
(Int-2-A)

4-Oxochroman-7-carbonitrile (11.0 g, 63.5 mmol) was dissolved in THF (250 mL) and cooled to −30° C. prior to the addition of LiHMDS (66.7 mL, 66.7 mmol) dropwise. The resulting solution was stirred for 20 min. Next, the temperature was lowered to −78° C. and the solution was stirred for 0.5 h. In another flask, NBS (11.3 g, 63.5 mmol) was dissolved in THF (250 mL) and cooled to −78° C. Then the anion solution was transferred into NBS/THF solution at −78° C. via cannula. The resulting solution was stirred at −78° C. for 40 min. The reaction was quenched with aqueous saturated NH₄Cl solution and extracted with EtOAc twice. The combined organic layers were washed with 1N HCl, brine, dried (MgSO₄), and filtered. The filtrate was concentrated and the resulting residue was purified by flash chromatography with 10% to 20% EtOAc/hexane on 120 g ISCO column to afford 3-bromo-4-oxochroman-7-carbonitrile (10.0 g, 39.7 mmol, 62.5% yield) as a pale yellow solid: LCMS=251.9 [M+H]⁺.

Int-2-B: Racemic 3-azido-4-oxochroman-7-carbonitrile

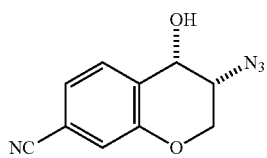
(Int-2-B)

3-Bromo-4-oxochroman-7-carbonitrile Int-2-A (140 mg, 0.55 mmol) was dissolved in DMF (3627 μL) and glacial acetic acid (91.0 μL) was added. The solution was cooled to −15° C. To this solution was added sodium azide (54.2 mg, 0.83 mmol) in water (725 μL) dropwise. After stirring for 2 h at −15° C., the reaction mixture was warmed to room temperature and stirred until all the starting material was consumed. The color of the solution turned dark red. The reaction mixture was diluted by the addition of 50 mL water and extracted by EtOAc twice. The combined organic layers were washed with saturated NaHCO₃ solution then brine, dried (MgSO₄), and filtered before it was concentrated to give racemic 3-azido-4-oxochroman-7-carbonitrile (110 mg, 0.51 mmol, 92.5% yield): LCMS=237.02 [M+Na]⁺.

Int-2-C: Racemic (3R*,4S*)-3-azido-4-hydroxychroman-7-carbonitrile (Int-2-C)

Racemic 3-azido-4-oxochroman-7-carbonitrile Int-2-B (2.30 g, 10.8 mmol) was dissolved in THF (103 mL) and water (5.42 mL) at 0° C. To this solution was added sodium borohydride (0.53 g, 14.1 mmol). The reaction mixture was stirred at 0° C. for 45 mins. Next, the reaction was quenched by addition of 1N HCl. The resulting solution was extracted with EtOAc and washed with water and brine. The organic layers were combined, dried (MgSO₄) and concentrated to give racemic (3R*,4S*)-3-azido-4-hydroxychroman-7-carbonitrile Int-2-C (2.21 g, 10.2 mmol, 94.3% yield): LCMS=217.06 [M+H]+.

Int-2-D: Racemic (3R*,4S*,E/Z)-3-azido-N',4-dihydroxychroman-7-carboximidamide

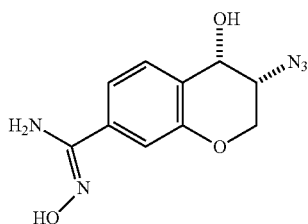

(Int-2-D)

Racemic (3R*,4S*)-3-azido-4-hydroxychroman-7-carbonitrile Int-2-C (5.08 g, 23.5 mmol) and hydroxylamine hydrochloride (3.27 g, 47.0 mmol) were mixed in 2-propanol (94.0 mL). To this suspension was added sodium bicarbonate (7.90 g, 94.0 mmol) and the resulting mixture was heated at reflux for 2 h. After the reaction mixture was cooled to room temperature, it was diluted with EtOAc (250 mL) and washed with water and brine. The combined aqueous layers were extracted again with EtOAc. The combined organic layers were dried (MgSO4) and concentrated to afford racemic (3R*,4S*,E/Z)-3-azido-N',4-dihydroxychroman-7-carboximidamide Int-2-D (5.71 g, 22.9 mmol, 97.5% yield): LCMS=250.08 [M+H]+.

Int-2: Racemic (3R*,4S*)-3-azido-7-(5-(3-phenyl-4-(trifluoromethyl)isoxazol-5-yl)-1,2,4-oxadiazol-3-yl)chroman-4-ol To a solution of 3-phenyl-4-(trifluoromethyl)isoxazole-5-carbonyl fluoride Int-1-G (273 mg, 1.05 mmol) in ACN (6.7 mL) was added racemic (3R*,4S*,E/Z)-3-azido-N',4-dihydroxychroman-7-carboximidamide (250 mg, 1.0 mmol) and Hunig's Base (210 µL, 1.2 mmol). The resulting solution was stirred overnight. Next, the solvent was evaporated. The resulting residue was purified by column chromatography (ISCO Combiflash Companion, 12 g silica gel, 10% ethyl acetate-hexane for 5 min then ramp to 50% ethyl acetate-hexane over 7 min then 50% ethyl acetate-hexane for 3 more min, product came out 8-10 min) to give racemic (3R*,4S*)-3-azido-7-(5-(3-phenyl-4-(trifluoromethyl)isoxazol-5-yl)-1,2,4-oxadiazol-3-yl)chroman-4-ol (280 mg, 0.59 mmol, 59.3% yield): LCMS=470.98 [M+H]+, 1H NMR (400 MHz, CDCl3) δ ppm 7.82 (1H, dd, J=8.03, 1.65 Hz), 7.66-7.72 (3H, m), 7.52-7.62 (4H, m), 4.96-5.02 (1H, m), 4.43-4.51 (1H, m), 4.32-4.38 (1H, m), 4.08-4.17 (1H, m).

Intermediate 3

Racemic (1S*,2R*)-2-azido-6-(5-(3-phenyl-4-(trifluoromethyl)isoxazol-5-yl)-1,2,4-oxadiazol-3-yl)-1,2,3,4-tetrahydronaphthalen-1-ol

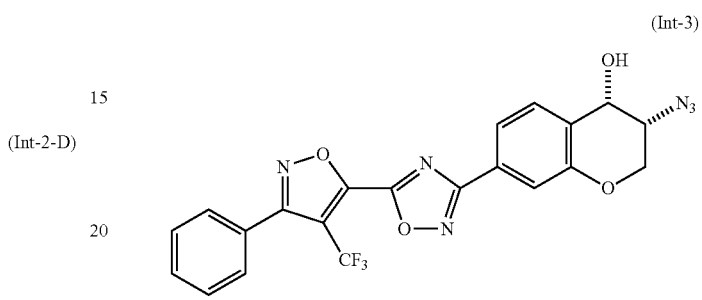

(Int-3)

Int-3-A: Racemic 6-bromo-5-oxo-5,6,7,8-tetrahydronaphthalene-2-carbonitrile

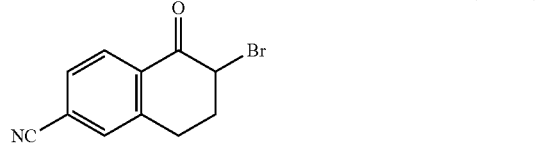

(Int-3-A)

5-Oxo-5,6,7,8-tetrahydronaphthalene-2-carbonitrile (1.0 g, 5.8 mmol), 1-bromopyrrolidine-2,5-dione (1.04 g, 5.8 mmol) and 4-methylbenzenesulfonic acid hydrate (0.111 g, 0.58 mmol) were ground in a porcelain mortar. The resulting powder was placed in a vial, and heated at 60° C. for 12 mins. The mixture became a muddy liquid at 60° C. After cooling to room temperature, the mixture was dissolved in CH2Cl2 (80 mL). The solution was washed with saturated NaHCO3, water, brine, and dried (MgSO4). Solvent was evaporated off to give racemic 6-bromo-5-oxo-5,6,7,8-tetrahydronaphthalene-2-carbonitrile (1.25 g, 5.0 mmol, 86% yield) as a yellow solid: LCMS=249.98 [M+H]+.

Int-3-B: Racemic 6-azido-5-oxo-5,6,7,8-tetrahydronaphthalene-2-carbonitrile

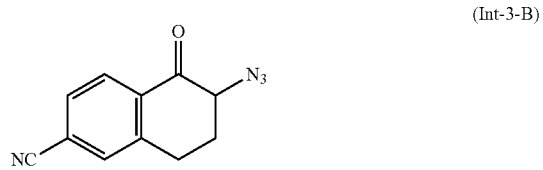 [SMILES: N#Cc1ccc2c(c1)CCC(N=[N+]=[N-])C2=O]

(Int-3-B)

To a solution of racemic 6-bromo-5-oxo-5,6,7,8-tetrahydronaphthalene-2-carbonitrile (100 mg, 0.4 mmol) in DMF (2611 mL) and acetic acid (65.3 mL) was added a solution of sodium azide (52.0 mg, 0.8 mmol) in water (522 mL) dropwise at 0° C. After 1 hour, the reaction was complete. The mixture was directly loaded to a 24 g ISCO column and purified by ISCO Combiflash Companion (0% ethyl acetate-hexane for 3 min then ramped to 20% ethyl acetate-hexane over 7 min then 20% ethyl acetate-hexane for 5 more minutes. The product came out 8-10 min) to afford racemic 6-azido-5-oxo-5,6,7,8-tetrahydronaphthalene-2-carbonitrile (35 mg, 0.16 mmol, 41.2%) as a white solid: LCMS=213.22 [M+H]$^+$.

Int-3-C: Racemic (5S*,6R*)-6-azido-5-hydroxy-5,6,7,8-tetrahydronaphthalene-2-carbonitrile

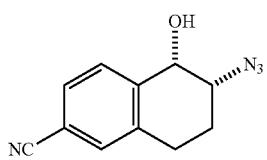

(Int-3-C)

Racemic 6-azido-5-oxo-5,6,7,8-tetrahydronaphthalene-2-carbonitrile (28 mg, 0.13 mmol) was dissolved in THF (1253 mL) and water (66.0 mL) at 0° C. To this solution was added sodium borohydride (6.49 mg, 0.17 mmol). The resulting solution was stirred at 0° C. for 45 min. After that, the reaction was quenched by several drops of 1N HCl. The mixture was loaded to an ISCO 13 g column directly and purified by ISCO Combiflash Companion (10% ethyl acetate-hexane for 3 min then ramp to 50% ethyl acetate-hexane over 7 min then 20% ethyl acetate-hexane for 5 more min, product came out 8-10 min) to afford racemic (5S*,6R*)-6-azido-5-hydroxy-5,6,7,8-tetrahydronaphthalene-2-carbonitrile (15.0 mg, 0.07 mmol, 53.1%) as a white solid. NMR showed that the product was a mixture of around 6:1 two diastereomers; LCMS=215.22 [M+H]$^+$.

Int-3-D: Racemic (5S*,6R*,E/Z)-6-azido-N',5-dihydroxy-5,6,7,8-tetrahydronaphthalene-2-carboximidamide (Int-3-D)

Racemic (5S*,6R*)-6-azido-5-hydroxy-5,6,7,8-tetrahydronaphthalene-2-carbonitrile (400 mg, 1.9 mmol) and hydroxylamine hydrochloride (260 mg, 3.7 mmol) were mixed in 2-propanol (7.5 mL). To this suspended solution was added sodium bicarbonate (627 mg, 7.5 mmol) and the solution was heated at reflux for 2 hr. Then the reaction mixture was cooled to room temperature and diluted by EtOAc (50 mL) and washed with water and brine. The combined aqueous layers were extracted again by EtOAc. The combined organic layers were dried (MgSO$_4$) and concentrated to afford pure racemic (5S*,6R*,E/Z)-6-azido-N',5-dihydroxy-5,6,7,8-tetrahydronaphthalene-2-carboximidamide (445 mg, 1.8 mmol, 96% yield).

Int-3: Racemic (1S*,2R*)-2-azido-6-(5-(3-phenyl-4-(trifluoromethyl)isoxazol-5-yl)-1,2,4-oxadiazol-3-yl)-1,2,3,4-tetrahydronaphthalen-1-ol Int-3 was prepared from Int. D according to general procedure for the preparation of Int. 2. LCMS=469.39 [M+H]$^+$, $^1$H NMR (400 MHz, DMSO-d$_6$) δ ppm 7.94 (1H, d, J=8.14 Hz), 7.85 (1H, s), 7.60-7.70 (6H, m), 6.01 (1H, d, J=6.16 Hz), 4.85 (1H, d, J=5.50 Hz), 3.86-4.02 (1H, m), 2.93-3.05 (1H, m), 2.81-2.92 (1H, m), 2.05-2.16 (1H, m), 1.94-2.04 (1H, m).

Intermediate 4

Racemic (1S*,2R*)-2-azido-5-(5-(3-phenyl-4-(trifluoromethyl)isoxazol-5-yl)-1,2,4-oxadiazol-3-yl)-2,3-dihydro-1H-inden-1-ol

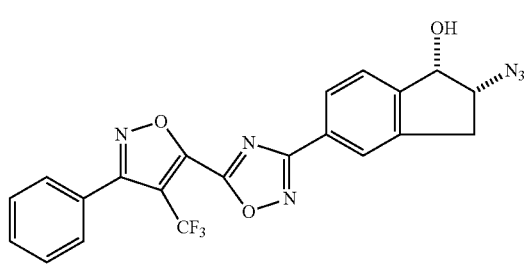

(Int-4)

Int-4-A: Racemic 2-bromo-1-oxo-2,3-dihydro-1H-indene-5-carbonitrile

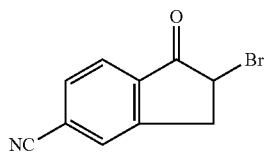

(Int-4-A)

Int-4-A was prepared according the general procedure employed to prepare Int-3-A. LCMS=235.96 [M+H]$^+$.

Int-4-B: Racemic 2-azido-1-oxo-2,3-dihydro-1H-indene-5-carbonitrile

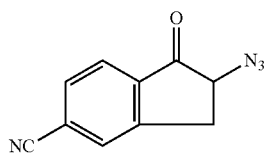

(Int-4-B)

Int-4-B was prepared according the general procedure employed to prepare Int-3-B. LCMS=199.05 [M+H]$^+$.

Int-4-C: Racemic (1S*,2R*)-2-azido-1-hydroxy-2,3-dihydro-1H-indene-5-carbonitrile

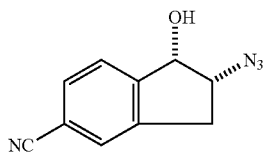

(Int-4-C)

Int-4-C was prepared according the general procedure employed to prepare Int-3-C. LCMS=201.07 [M+H]$^+$.

Int-4-D: Racemic (1S*,2R*,E/Z)-2-azido-N',1-dihydroxy-2,3-dihydro-1H-indene-5-carboximidamide

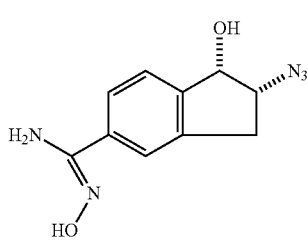

(Int-4-D)

Int-4-D was prepared according the general procedure employed to prepare Int-3-D. LCMS=234.09 [M+H]$^+$.

Int-4: Racemic (1S*,2R*)-2-azido-5-(5-(3-phenyl-4-(trifluoromethyl)isoxazol-5-yl)-1,2,4-oxadiazol-3-yl)-2,3-dihydro-1H-inden-1-ol Int-4 was prepared according the general procedure employed to prepare Int-2. LCMS=455.11 [M+H]$^+$; $^1$H NMR (400 MHz, CDCl$_3$) δ ppm 8.16 (1H, d, J=7.92 Hz), 8.11 (1H, s), 7.69 (2H, d, J=6.82 Hz), 7.52-7.65 (4H, m), 5.25 (1H, dd, J=8.80, 5.28 Hz), 4.41-4.57 (1H, m), 3.26 (2H, t, J=4.07 Hz), 2.47 (1H, d, J=9.02 Hz).

Intermediate 5

Racemic (1S*,2R*)-1-(tert-butyldimethylsilyloxy)-6-(5-(3-phenyl-4-(trifluoromethyl)isoxazol-5-yl)-1,2,4-oxadiazol-3-yl)-1,2,3,4-tetrahydronaphthalen-2-amine (Int-5)

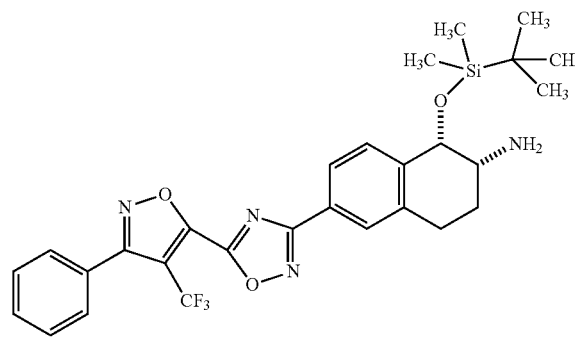

Int-5-A: Racemic 3-((5S*,6R*)-6-azido-5-(tert-butyldimethylsilyloxy)-5,6,7,8-tetrahydronaphthalen-2-yl)-5-(3-phenyl-4-(trifluoromethyl)isoxazol-5-yl)-1,2,4-oxadiazole (Int-5-A)

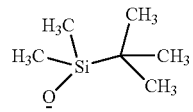

Racemic 2-azido-6-(5-(3-phenyl-4-(trifluoromethyl)isoxazol-5-yl)-1,2,4-oxadiazol-3-yl)-1,2,3,4-tetrahydronaphthalen-1-ol (130 mg, 0.28 mmol) was dissolved in CH$_2$Cl$_2$ (694 μL). To this solution was added 2,6-lutidine (129 μL, 1.1 mmol) and tert-butyldimethylsilyl trifluoromethanesulfonate (133 μL, 0.55 mmol). The reaction was stirred at room temperature for 1 h. After that, the solution was loaded onto a 12 g ISCO column and purified by ISCO Combiflash Companion (0% ethyl acetate-hexane for 3 min then ramp to 20% ethyl acetate-hexane over 5 min then 20% ethyl acetate-hexane for 8 more min, product came out 8-10 min) to afford racemic-3-(6-azido-5-(tert-butyldimethylsilyloxy)-5,6,7,8-tetrahydronaphthalen-2-yl)-5-(3-phenyl-4-(trifluoromethyl)isoxazol-5-yl)-1,2,4-oxadiazole (130 mg, 0.22 mmol, 80%) as a white solid: LCMS=605.34 [M+Na]$^+$.

Int-5: Racemic (1S*,2R*)-1-(tert-butyldimethylsilyloxy)-6-(5-(3-phenyl-4-(trifluoromethyl)isoxazol-5-yl)-1,2,4-oxadiazol-3-yl)-1,2,3,4-tetrahydronaphthalen-2-amine Racemic 3-(6-azido-5-(tert-butyldimethylsilyloxy)-5,6,7,8-tetrahydronaphthalen-2-yl)-5-(3-phenyl-4-(trifluoromethyl)isoxazol-5-yl)-1,2,4-oxadiazole (500 mg, 0.86 mmol) was dissolved in MeOH (2131 μL), ethyl acetate (2131 μL), and CH$_2$Cl$_2$ (2131 μL). To this solution was added tin(II) chloride dihydrate (1.94 mg, 8.6 mmol) and the reaction mixture was stirred overnight. The solvent was evaporated and the residue was redissolved in CH$_2$Cl$_2$ and washed with 1N NaOH and brine. The organic phase was dried over MgSO$_4$ and concentrated to afford racemic (1S*,2R*)-1-(tert-butyldimethylsilyloxy)-6-(5-(3-phenyl-4-(trifluoromethyl)isoxazol-5-yl)-1,2,4-oxadiazol-3-yl)-1,2,3,4-tetrahydronaphthalen-2-amine (46.2 mg, 0.83 mmol, 96.5%) as a pale yellow oil: LCMS=557.44 [M+H]$^+$.

Intermediate 6

Racemic (3R*,4S*)-4-(tert-butyldimethylsilyloxy)-7-(5-(3-phenyl-4-(trifluoromethyl)isoxazol-5-yl)-1,2,4-oxadiazol-3-yl)chroman-3-amine

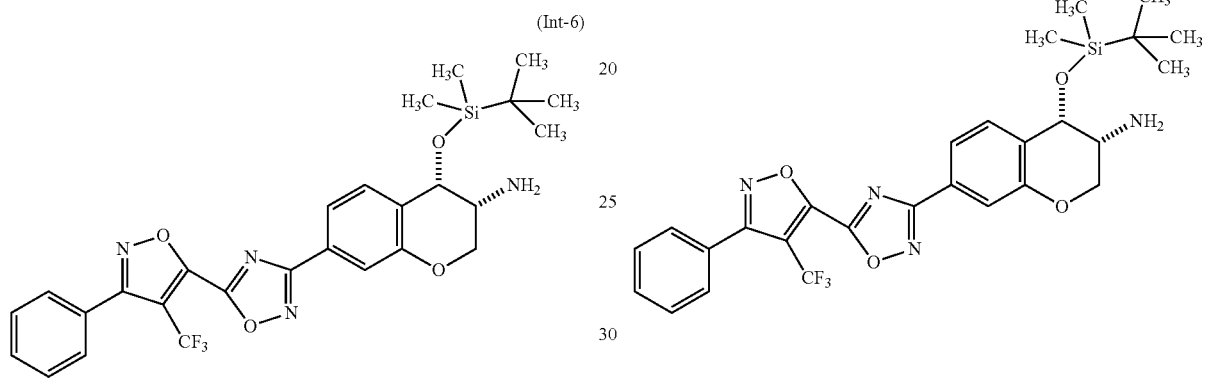

Int-6-A: 3-(3R*,4S*)-3-Azido-4-(tert-butyldimethylsilyloxy)chroman-7-yl)-5-(3-phenyl-4-(trifluoromethyl)isoxazol-5-yl)-1,2,4-oxadiazole Int-6-A was prepared according the general procedure employed to prepare Int-5-A. LCMS=585.18 [M+H]$^+$.

Int-6: Racemic (3R*,4S*)-4-(tert-butyldimethylsilyloxy)-7-(5-(3-phenyl-4-(trifluoromethyl)isoxazol-5-yl)-1,2,4-oxadiazol-3-yl)chroman-3-amine

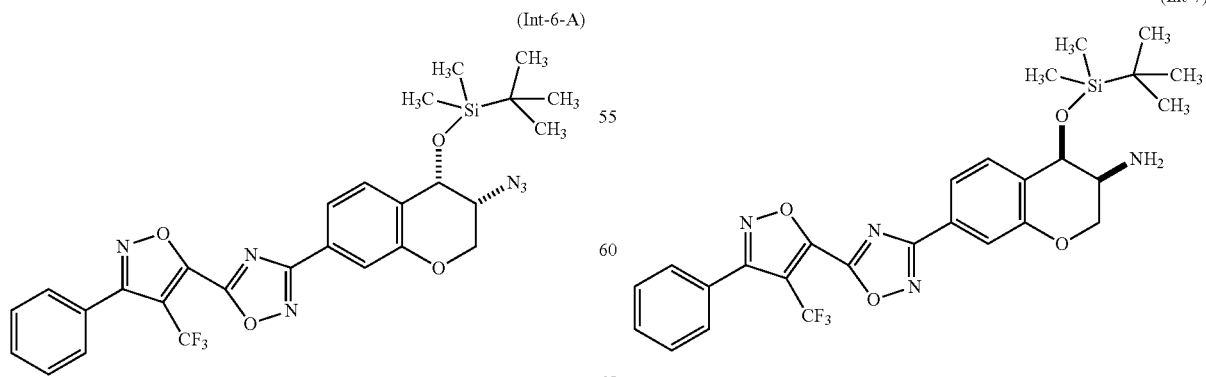

Int-6 was prepared according the general procedure employed to prepare Int-V. LCMS=559.19 [M+H]$^+$.

Intermediate 7

(3S,4R)-4-(tert-Butyldimethylsilyloxy)-7-(5-(3-phenyl-4-(trifluoromethyl)isoxazol-5-yl)-1,2,4-oxadiazol-3-yl)chroman-3-amine Int-6-A was prepared according the general procedure employed to prepare Int-6. LCMS=559.19 [M+H]⁺.

Intermediate 8

(4R,5S)-4-Methyl-3-(3-oxocyclohexanecarbonyl)-5-phenyloxazolidin-2-one

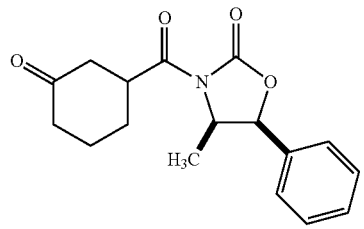
(Int-8)

Racemic 3-oxocyclohexanecarboxylic acid (1.0 g, 7.03 mmol) was dissolved in THF (27.1 mL). To this solution was added triethylamine (1.9 mL, 13.5 mmol) followed by pivaloyl chloride (0.8 mL, 6.5 mmol) at −20° C. The resulting mixture was stirred at −20° C. for 1 h. After that, LiCl (0.252 g, 5.9 mmol) and (4R,5S)-4-methyl-5-phenyloxazolidin-2-one (0.959 g, 5.4 mmol) were added to the solution at −20° C. The reaction mixture was warmed to room temperature and stirred overnight, before the reaction was quenched with 0.2 N HCl. The THF was removed and the resulting mixture was partitioned by 0.2 N HCl and EtOAc. The organic layer was collected and washed with brine, dried (MgSO₄) and concentrated. The resulting residue was purified by preparative HPLC (PHENOMENEX® Luna 5u C18 21.2×250 mm, isocratic elution with Method 1-MeOH/water containing 0.1% trifluoroacetic acid as defined above, 51% B over 30 min, 25 mL/min, 220 nM: the first peak (retention time=15.3 min) was (4R,5S)-4-methyl-3-((S)-3-oxocyclohexanecarbonyl)-5-phenyloxazolidin-2-one, Int-8A, (LCMS=302.0 [M+H]⁺), and the second peak (retention time=19.6 min) was (4R,5S)-4-methyl-3-((R)-3-oxocyclohexanecarbonyl)-5-phenyloxazolidin-2-one, Int-8B, LCMS=324.1 [M+Na]⁺ by comparison to the R-3-oxocyclohexanecarboxylic acid case (*Aust. J. Chem.*, 34:2231 (1981)).

Example 1

Racemic (3R*,4S*)-3-amino-7-(5-(3-phenyl-4-(trifluoromethyl)isoxazol-5-yl)-1,2,4-oxadiazol-3-yl)chroman-4-ol, TFA

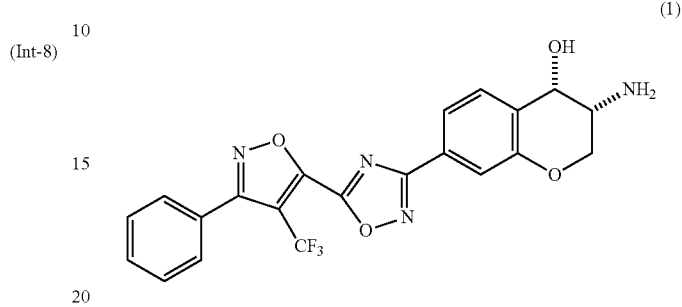
(1)

Racemic (3R*,4S*)-3-azido-7-(5-(3-phenyl-4-(trifluoromethyl)isoxazol-5-yl)-1,2,4-oxadiazol-3-yl)chroman-4-ol Int-2 (75 mg, 0.16 mmol) was dissolved in MeOH (638 μL) and CH₂Cl₂ (638 μL). To this solution was added tin(II) chloride dihydrate (180 mg, 0.8 mmol). After 10 h, the solution was filtered and concentrated. The resulting residue was then purified by preparative HPLC (PHENOMENEX® Luna 5u C18 21.2×100 mm, gradient elution with Method 1-MeOH/water containing 0.1% trifluoroacetic acid as defined above, 0% B to 100% B over 10 min, 20 mL/min, 220 nM) to give racemic (3R*,4S*)-3-amino-7-(5-(3-phenyl-4-(trifluoromethyl)isoxazol-5-yl)-1,2,4-oxadiazol-3-yl)chroman-4-ol, TFA salt Ex. 1 (10 mg, 0.02 mmol): LCMS=445.0 [M+H]⁺; ¹H NMR (400 MHz, CD₃OD) δ ppm 7.88 (3H, dd, J=8.03, 1.65 Hz), 7.71-7.75 (11H, m), 7.60-7.71 (11H, m), 5.12 (1H, d, J=4.62 Hz), 4.40-4.50 (6H, m), 3.86 (3H, ddd, J=6.44, 4.57, 3.30 Hz); HPLC Peak RT=8.6 min (Analytical Method A).

Examples 2-3

Examples 2-3 were prepared according to the general procedure described in Example 1.

TABLE 1

| Ex. | R | Name | Observed MS Ion (M + H)+ | RTᵃ [min] |
|---|---|---|---|---|
| 2 | 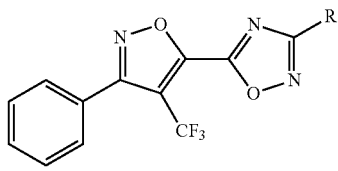 | Racemic-2-amino-5-(5-(3-phenyl-4-(trifluoromethyl)isoxazol-5-yl)-1,2,4-oxadiazol-3-yl)-2,3-dihydro-1H-inden-1-ol, TFA salt | 429.1 | 8.4 |

TABLE 1-continued

[Structure: 3-phenyl-4-(trifluoromethyl)isoxazol-5-yl linked to 1,2,4-oxadiazol-3-yl with R group]

| Ex. | R | Name | Observed MS Ion (M + H)+ | RT[a] [min] |
|---|---|---|---|---|
| 3 | [6-substituted-1-hydroxy-2-amino-tetrahydronaphthalenyl group with OH and NH₂] | Racemic-2-amino-6-(5-(3-phenyl-4-(trifluoromethyl)isoxazol-5-yl)-1,2,4-oxadiazol-3-yl)-1,2,3,4-tetrahydronaphthalen-1-ol, TFA salt | 443.0 | 8.4 |

[a] Analytical HPLC using Method A

Example 4

Racemic (3R*,4R*)-3-amino-7-(5-(3-phenyl-4-(trifluoromethyl)isoxazol-5-yl)-1,2,4-oxadiazol-3-yl)chroman-4-ol, TFA

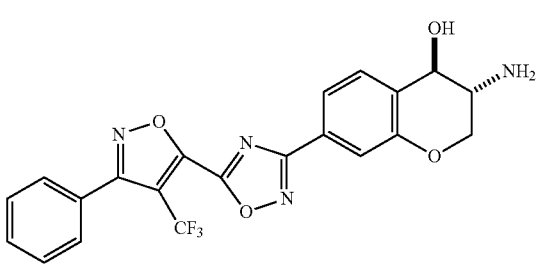

(4)

Racemic (3R*,4S*)-3-azido-7-(5-(3-phenyl-4-(trifluoromethyl)isoxazol-5-yl)-1,2,4-oxadiazol-3-yl)chroman-4-ol Int-2 (100 mg, 0.21 mmol), 4-nitrobenzoic acid (142 mg, 0.85 mmol), and PPh₃ (223 mg, 0.85 mmol) were mixed in THF (2.1 mL). This reaction was cooled to 0° C. and DEAD (135 µL, 0.85 mmol) was added dropwise. The reaction was stirred overnight. Next, the reaction mixture was diluted with MeCN and purified by preparative HPLC (Column: PHENOMENEX® Luna 5u C18 21.2×100 mm, gradient elution with Method 1-MeOH/water containing 0.1% trifluoroacetic acid as defined above, 0% B to 100% B over 10 min, 20 mL/min, 220 nM) to give racemic (3R*,4R*)-3-azido-7-(5-(3-phenyl-4-(trifluoromethyl)isoxazol-5-yl)-1,2,4-oxadiazol-3-yl)chroman-4-yl-4-nitrobenzoate [105 mg, ¹H NMR 400 MHz, methanol-d₄, δ ppm 8.37-8.42 (1H, m), 8.31-8.36 (1H, m), 7.79 (1H, d, J=1.54 Hz), 7.60-7.76 (4H, m), 6.22 (1H, d, J=3.96 Hz), 4.59 (1H, s), 4.38-4.42 (1H, m)]. This material was dissolved in THF (2 mL), MeOH (3 mL), and water (1 mL) prior to the addition of aqueous 1N LiOH (0.19 mL). After 2 h, the solution was concentrated and EtOAc was added. This was washed with brine and the organic layer was dried (MgSO₄), filtered, and concentrated. The resulting material was dissolved in MeOH (1.1 mL) and CH₂Cl₂ (1.1 mL) and tin(II) chloride dehydrate (240 mg, 1.06 mmol) was added. After 10 h, the reaction was filtered and purified by preparative HPLC (Column: PHENOMENEX® Luna 5u C18 21.2×100 mm, gradient elution with Method 1-MeOH/water containing 0.1% trifluoroacetic acid as defined above, 0% B to 100% B over 10 min, 20 mL/min, 220 nM) and the product peak (LCMS=445.0 [M+H]⁺) was then purified by preparative SFC (Column: 2-ethylpridine, 3×25 cm, column temperature 35° C., isocratic elution with mobile phase 25% MeOH+0.1% DEA in CO₂, 150 mL/min, 220 nM, product retention=3.25 min) to give racemic (3R*,4R*)-3-amino-7-(5-(3-phenyl-4-(trifluoromethyl)isoxazol-5-yl)-1,2,4-oxadiazol-3-yl)chroman-4-ol, TFA salt Ex 4 (10 mg): LCMS=445.0 [M+H]⁺; ¹H NMR (400 MHz, methanol-d₄) δ ppm 7.78-7.82 (2H, m), 7.71-7.75 (4H, m), 7.60-7.68 (13H, m), 4.52 (2H, d, J=5.72 Hz), 4.38 (3H, dd, J=11.11, 2.97 Hz), 4.11 (2H, dd, J=11.00, 6.38 Hz), 3.19 (2H, td); HPLC Peak RT=8.33 min (Analytical Method A).

Example 5

Racemic 3-((3R*,4R*)-4-hydroxy-7-(5-(3-phenyl-4-(trifluoromethyl)isoxazol-5-yl)-1,2,4-oxadiazol-3-yl)chroman-3-ylamino)propanoic acid, TFA salt

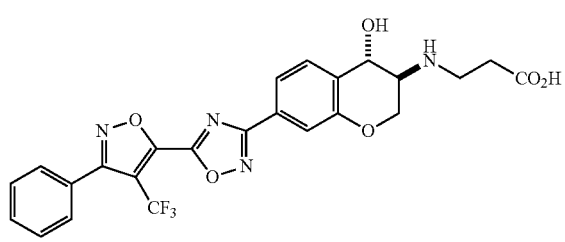

(5)

Racemic (3R*,4R*)-3-amino-7-(5-(3-phenyl-4-(trifluoromethyl)isoxazol-5-yl)-1,2,4-oxadiazol-3-yl)chroman-4-ol, TFA salt (16 mg, 0.036 mmol) was dissolved in 2-propanol (0.72 ml). To this solution was added TEA (25 µl, 0.18 mmol) and tert-butyl acrylate (21 µl, 0.14 mmol). The solution was stirred at 80° C. for 3 days. After cooling, the solvent was evaporated and the resulting residue was redissolved in CH₂Cl₂ (1 mL). To this solution was added TFA (0.5 mL). After 2 h, the solution was mixed with MeCN and purified by preparative HPLC (Column: PHENOMENEX® Luna C18, 5-µm particles (30×100 mm; Guard Column: none; Mobile Phase A: 5:95 acetonitrile:water with 0.1% TFA; Mobile Phase B: 95:5 acetonitrile:water with 0.1% TFA; Gradient: 15%-100% B over 10 minutes; Flow: 30 mL/min, uv detection 254 nM) to give racemic 3-((3R*,4R*)-4-hydroxy-7-(5-(3-phenyl-4-(trifluoromethyl)isoxazol-5-yl)-1,2,4-oxadiazol-3-yl)chroman-3-ylamino)propanoic acid, TFA salt (5 mg): LCMS [M+H]⁺=517.0; ¹H NMR (400 MHz, methanol-d₄) δ ppm 7.92 (1H, dd, J=8.03, 1.65 Hz), 7.79 (1H, d, J=1.54 Hz), 7.72 (3H, dd, J=7.26, 5.72 Hz), 7.60-7.68 (3H, m), 4.94 (1H, d, J=4.18 Hz), 4.58 (2H, d, J=3.30 Hz), 3.73 (1H, d, J=4.18 Hz), 3.55 (2H, d, J=3.96 Hz), 2.81 (2H, t); HPLC Peak RT=8.44 min (Analytical Method A).

Examples 6 and 7

Racemic (3R*,4S*)-tert-butyl-4-hydroxy-7-(5-(3-phenyl-4-(trifluoromethyl)isoxazol-5-yl)-1,2,4-oxadiazol-3-yl)chroman-3-ylcarbamate

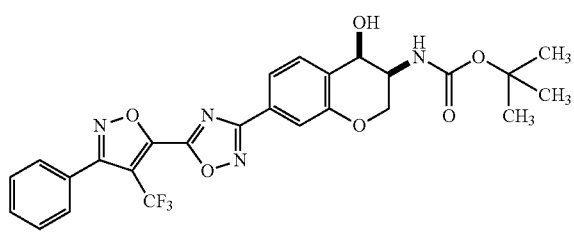

(6)

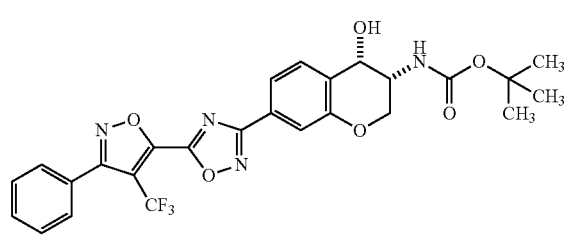

(7)

Racemic (3R*,4S*)-3-amino-7-(5-(3-phenyl-4-(trifluoromethyl)isoxazol-5-yl)-1,2,4-oxadiazol-3-yl)chroman-4-ol (1.8 g, 4.1 mmol) was dissolved in THF (13.5 mL) and water (6.8 mL). To this solution was added TEA (0.69 mL, 4.9 mmol) and Boc₂O (1.03 mL, 4.5 mmol). The reaction mixture was stirred for 2 hours. EtOAc was added and the layers were separated. The organic layer was washed with brine before it was dried (MgSO₄), filtered, and concentrated to give racemic (3R*,4S*)-tert-butyl-4-hydroxy-7-(5-(3-phenyl-4-(trifluoromethyl)isoxazol-5-yl)-1,2,4-oxadiazol-3-yl)chroman-3-ylcarbamate (2.2 g), which was separated into its individual enantiomers by chiral preparative SFC (Lux-Cellulose-2, column temperature 35° C., isocratic elution with mobile phase 20% EtOH+0.1% TEA in CO₂, 150 mL/min, 250 nM, first product peak retention=8.15 min and second product peak retention=9.93 min) to give the separate enantiomers: tert-butyl (3S,4R)-4-hydroxy-7-(5-(3-phenyl-4-(trifluoromethyl)isoxazol-5-yl)-1,2,4-oxadiazol-3-yl)chroman-3-ylcarbamate, Ex. 6 (729 mg) was eluted first at 8.15 min, [α]=−47.3° (c.=1.29, MeOH), LCMS=545.2 [M+H]⁺; and tert-butyl (3R,4S)-4-hydroxy-7-(5-(3-phenyl-4-(trifluoromethyl)isoxazol-5-yl)-1,2,4-oxadiazol-3-yl)chroman-3-ylcarbamate, Ex. 7 (966 mg) was eluted second at 9.93 min, [α]=56.7° (c.=2.61, MeOH), LCMS=545.1 [M+H]⁺.

Example 8

(3S,4R)-3-Amino-7-(5-(3-phenyl-4-(trifluoromethyl)isoxazol-5-yl)-1,2,4-oxadiazol-3-yl)chroman-4-ol, TFA salt

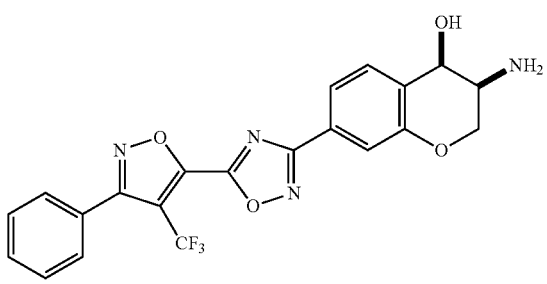

(8)

tert-Butyl (3S,4R)-4-hydroxy-7-(5-(3-phenyl-4-(trifluoromethyl)isoxazol-5-yl)-1,2,4-oxadiazol-3-yl)chroman-3-ylcarbamate Ex 6 (400 mg, 0.735 mmol) was dissolved in 30% TFA solution in DCM (2939 µl). After 2 h the reaction mixture was concentrated to give (3S,4R)-tert-butyl-4-hydroxy-7-(5-(3-phenyl-4-(trifluoromethyl)isoxazol-5-yl)-1,2,4-oxadiazol-3-yl)chroman-3-ylcarbamate, TFA salt (quant.): LCMS=445.0 [M+H]⁺; ¹H NMR and HPLC as in Ex. 1.

Example 9

(3R,4S)-3-Amino-7-(5-(3-phenyl-4-(trifluoromethyl)isoxazol-5-yl)-1,2,4-oxadiazol-3-yl)chroman-4-ol, TFA salt

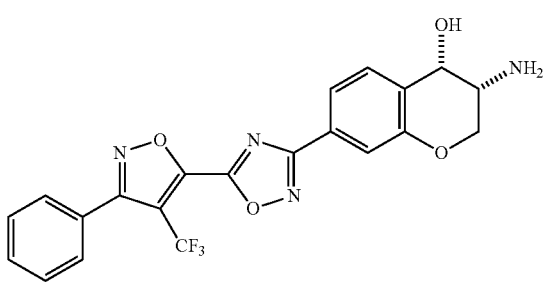

(9)

tert-Butyl (3S,4R)-4-hydroxy-7-(5-(3-phenyl-4-(trifluoromethyl)isoxazol-5-yl)-1,2,4-oxadiazol-3-yl)chroman-3-ylcarbamate (500 mg) was dissolved in 30% TFA solution in DCM (3673 µl). After 2 h the reaction mixture was concentrated to give (3R,4S)-tert-butyl-4-hydroxy-7-(5-(3-phenyl-4-(trifluoromethyl)isoxazol-5-yl)-1,2,4-oxadiazol-3-yl)

chroman-3-ylcarbamate, TFA salt (quant.): LCMS=445.0 [M+H]⁺; ¹H NMR and HPLC as in Ex. 1.

Example 10

Racemic (3R*,4S*)-3-(isopropylamino)-7-(5-(3-phenyl-4-(trifluoromethyl)isoxazol-5-yl)-1,2,4-oxadiazol-3-yl)chroman-4-ol

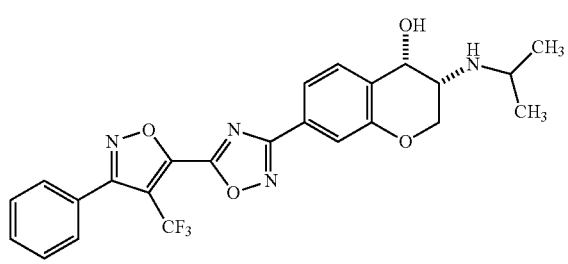

(10)

Racemic (3R*,4S*)-3-amino-7-(5-(3-phenyl-4-(trifluoromethyl)isoxazol-5-yl)-1,2,4-oxadiazol-3-yl)chroman-4-ol, TFA salt (33 mg, 0.07 mmol) was dissolved in CHCl₃ (1 mL) prior to the addition of Et₃N (0.04 mL, 0.3 mL), acetone (0.02 mL, 0.3 mmol), and NaBH(OAc)₃ (31.5 mg, 0.15 mmol). After 2 h, the solution was filtered and concentrated. The resulting residue was then purified by preparative HPLC: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give racemic (3R*,4S*)-3-(isopropylamino)-7-(5-(3-phenyl-4-(trifluoromethyl)isoxazol-5-yl)-1,2,4-oxadiazol-3-yl)chroman-4-ol (15.2 mg): LCMS=487.0 [M+H]⁺; ¹H NMR (400 MHz, 1:1 CDCl₃:CD₃OD) δ ppm ¹H NMR (400 MHz, MeOD) δ ppm 7.26-7.84 (8H, m), 4.69 (1H, d, J=3.74 Hz), 4.07-4.21 (2H, m), 3.15 (1H, dd, J=8.25, 4.29 Hz), 3.00-3.11 (1H, m), 1.02-1.17 (6H, m); HPLC Peak RT=8.4 min (Analytical Method A).

Examples 11-46

Examples 11-46 were prepared according to the general procedure described in Example 10.

TABLE 2

| Ex. | R | Name | Observed MS Ion (M + H)+ | RTᵃ [min] |
|---|---|---|---|---|
| 11 | cyclohexyl structure | Racemic cis-3-(cyclohexylamino)-7-(5-(3-phenyl-4-(trifluoromethyl)-isoxazol-5-yl)-1,2,4-oxadiazol-3-yl)chroman-4-ol, TFA salt | 527.0 | 8.8 |
| 12 | butanoic acid structure | Racemic 3-((3R*,4S*)-4-hydroxy-7-(5-(3-phenyl-4-(trifluoromethyl)-isoxazol-5-yl)-1,2,4-oxadiazol-3-yl)chroman-3-ylamino) butanoic acid, TFA salt (mixture of diastereomers at methyl center) | 531.0 | 8.9 |

TABLE 2-continued

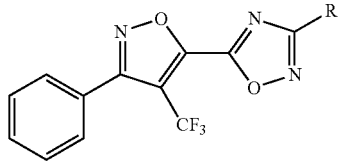

| Ex. | R | Name | Observed MS Ion (M + H)+ | RT$^a$ [min] |
|---|---|---|---|---|
| 13 | 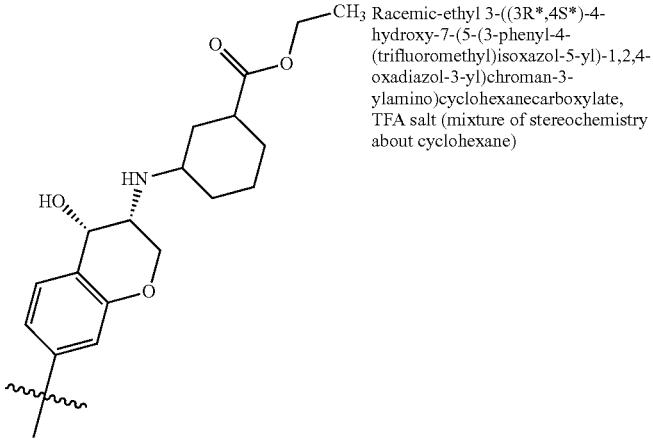 | Racemic-ethyl 3-((3R*,4S*)-4-hydroxy-7-(5-(3-phenyl-4-(trifluoromethyl)isoxazol-5-yl)-1,2,4-oxadiazol-3-yl)chroman-3-ylamino)cyclohexanecarboxylate, TFA salt (mixture of stereochemistry about cyclohexane) | 599.0 | 9.9 |
| 14 | 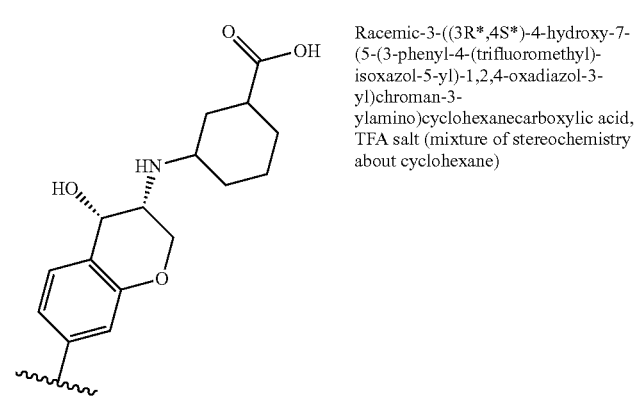 | Racemic-ethyl 4-((3R*,4S*)-4-hydroxy-7-(5-(3-phenyl-4-(trifluoromethyl)isoxazol-5-yl)-1,2,4-oxadiazol-3-yl)chroman-3-ylamino)cyclohexanecarboxylate, TFA salt (mixture of stereochemistry about cyclohexane) | 599.0 | 9.8 |
| 15 | | Racemic-3-((3R*,4S*)-4-hydroxy-7-(5-(3-phenyl-4-(trifluoromethyl)-isoxazol-5-yl)-1,2,4-oxadiazol-3-yl)chroman-3-ylamino)cyclohexanecarboxylic acid, TFA salt (mixture of stereochemistry about cyclohexane) | 571.0 | 8.9 |

TABLE 2-continued

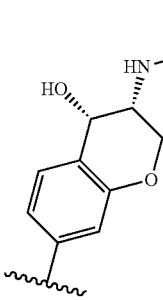

| Ex. | R | Name | Observed MS Ion (M + H)+ | RT$^a$ [min] |
|---|---|---|---|---|
| 16 | 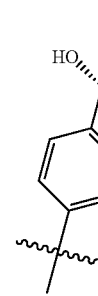 | Racemic-4-((3R*,4S*)-4-hydroxy-7-(5-(3-phenyl-4-(trifluoromethyl)-isoxazol-5-yl)-1,2,4-oxadiazol-3-yl)chroman-3-ylamino)-cyclohexanecarboxylic acid, TFA salt (mixture of stereochemistry about cyclohexane) | 571.0 | 9.0 |
| 17 | 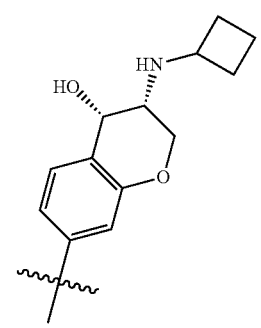 [SMILES: *c1ccc2c(c1)OC[C@@H](NC1CCC1)[C@H]2O] | Racemic-(3R*,4S*)-3-(dimethylamino)-7-(5-(3-phenyl-4-(trifluoromethyl)isoxazol-5-yl)-1,2,4-oxadiazol-3-yl)chroman-4-ol | 473.0 | 8.3 |
| 18 | 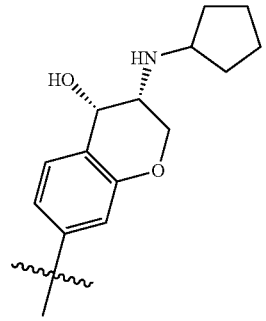 [SMILES: *c1ccc2c(c1)OC[C@@H](NC1CCCC1)[C@H]2O] | Racemic-(3R*,4S*)-3-(cyclobutylamino)-7-(5-(3-phenyl-4-(trifluoromethyl)isoxazol-5-yl)-1,2,4-oxadiazol-3-yl)chroman-4-ol, TFA salt | 499.0 | 8.6 |
| 19 | | Racemic-(3R*,4S*)-3-(cyclopentylamino)-7-(5-(3-phenyl-4-(trifluoromethyl)isoxazol-5-yl)-1,2,4-oxadiazol-3-yl)chroman-4-ol, TFA salt | 513.0 | 8.7 |

TABLE 2-continued

| Ex. | R | Name | Observed MS Ion (M + H)+ | RT$^a$ [min] |
|---|---|---|---|---|
| 20 | (structure with ethyl ester, methyl branch, HN linker to 4-hydroxychroman) | Racemic-ethyl 3-((3R*,4S*)-4-hydroxy-7-(5-(3-phenyl-4-(trifluoromethyl)isoxazol-5-yl)-1,2,4-oxadiazol-3-yl)chroman-3-ylamino)-2-methylpropanoate, TFA salt (mixture of diastereomers at methyl center) | 559.0 | 9.6 |
| 21 | (structure with cyclopentanecarboxylic acid, HN linker to 4-hydroxychroman) | Racemic-3-((3R*,4S*)-4-hydroxy-7-(5-(3-phenyl-4-(trifluoromethyl)-isoxazol-5-yl)-1,2,4-oxadiazol-3-yl)chroman-3-ylamino)-cyclopentanecarboxylic acid, TFA salt (mixture of stereochemistry about cyclopentane) | 557.0 | 8.8 |
| 22 | (structure with carboxylic acid, methyl branch, HN linker to 4-hydroxychroman) | Racemic-3-((3R*,4S*)-4-hydroxy-7-(5-(3-phenyl-4-(trifluoromethyl)-isoxazol-5-yl)-1,2,4-oxadiazol-3-yl)chroman-3-ylamino)-2-methylpropanoic acid, TFA salt (mixture of diastereomers at methyl center) | 530.9 | 8.8 |

TABLE 2-continued

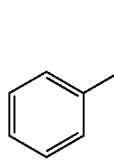

| Ex. | R | Name | Observed MS Ion (M + H)+ | RT$^a$ [min] |
|---|---|---|---|---|
| 23 | 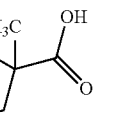 | Racemic-3-((3R*,4S*)-4-hydroxy-7-(5-(3-phenyl-4-(trifluoromethyl)-isoxazol-5-yl)-1,2,4-oxadiazol-3-yl)chroman-3-ylamino)-2,2-dimethylpropanoic acid, TFA salt | 544.9 | 9.0 |
| 24 |  | (1S,3R)-3-((3S,4R)-4-hydroxy-7-(5-(3-phenyl-4-(trifluoromethyl)-isoxazol-5-yl)-1,2,4-oxadiazol-3-yl)chroman-3-ylamino)-cyclobutanecarboxylic acid, TFA salt | 543.0 | 8.0 |
| 25 | | (1R,3S)-3-((3S,4R)-4-hydroxy-7-(5-(3-phenyl-4-(trifluoromethyl)-isoxazol-5-yl)-1,2,4-oxadiazol-3-yl)chroman-3-ylamino)-cyclobutanecarboxylic acid, TFA salt | 543.0 | 7.4 |

TABLE 2-continued

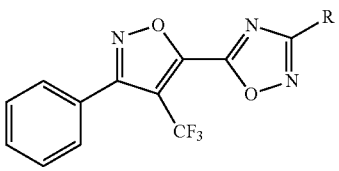

| Ex. | R | Name | Observed MS Ion (M + H)+ | RT$^a$ [min] |
|---|---|---|---|---|
| 26 | 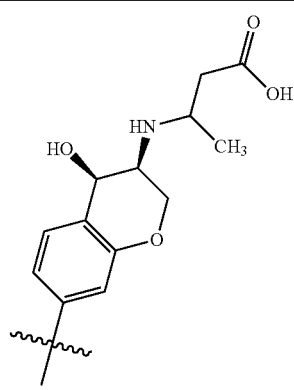 | 3-((3S,4R)-4-hydroxy-7-(5-(3-phenyl-4-(trifluoromethyl)isoxazol-5-yl)-1,2,4-oxadiazol-3-yl)chroman-3-ylamino) butanoic acid, TFA salt (first isomer off HPLC) | 531.0 | 8.2 |
| 27 | 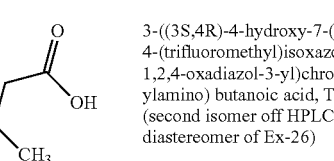 | 3-((3S,4R)-4-hydroxy-7-(5-(3-phenyl-4-(trifluoromethyl)isoxazol-5-yl)-1,2,4-oxadiazol-3-yl)chroman-3-ylamino) butanoic acid, TFA salt (second isomer off HPLC, diastereomer of Ex-26) | 531.0 | 8.3 |
| 28 | 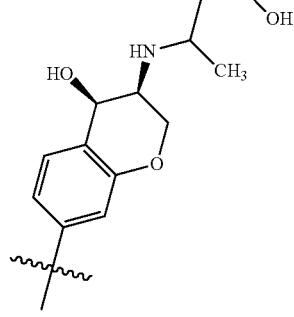 | 3-((3R,4S)-4-hydroxy-7-(5-(3-phenyl-4-(trifluoromethyl)isoxazol-5-yl)-1,2,4-oxadiazol-3-yl)chroman-3-ylamino) butanoic acid, TFA salt (first isomer off HPLC) | 531.0 | 8.2 |

TABLE 2-continued

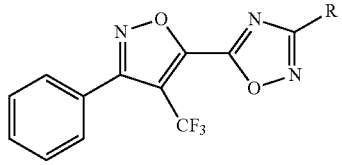

| Ex. | R | Name | Observed MS Ion (M + H)+ | RT<sup>a</sup> [min] |
|---|---|---|---|---|
| 29 | 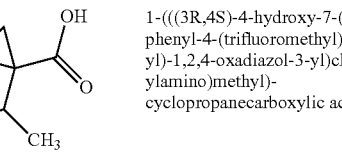 | 3-((3R,4S)-4-hydroxy-7-(5-(3-phenyl-4-(trifluoromethyl)isoxazol-5-yl)-1,2,4-oxadiazol-3-yl)chroman-3-ylamino) butanoic acid, TFA salt (second isomer off HPLC, diastereomer of Ex-28) | 531.0 | 8.3 |
| 30 | 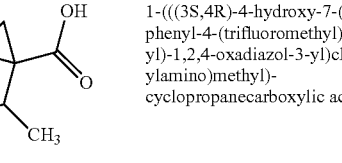 | 1-(((3R,4S)-4-hydroxy-7-(5-(3-phenyl-4-(trifluoromethyl)isoxazol-5-yl)-1,2,4-oxadiazol-3-yl)chroman-3-ylamino)methyl)-cyclopropanecarboxylic acid, TFA salt | 543.0 | 7.5 |
| 31 | 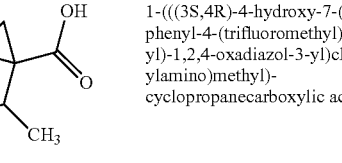 | 1-(((3S,4R)-4-hydroxy-7-(5-(3-phenyl-4-(trifluoromethyl)isoxazol-5-yl)-1,2,4-oxadiazol-3-yl)chroman-3-ylamino)methyl)-cyclopropanecarboxylic acid, TFA salt | 543.0 | 7.4 |

TABLE 2-continued

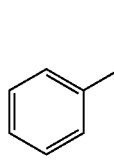

| Ex. | R | Name | Observed MS Ion (M + H)+ | RT$^a$ [min] |
|---|---|---|---|---|
| 32 | 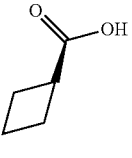 | (1S,3S)-3-((3R,4S)-4-hydroxy-7-(5-(3-phenyl-4-(trifluoromethyl)-isoxazol-5-yl)-1,2,4-oxadiazol-3-yl)chroman-3-ylamino)-cyclobutanecarboxylic acid, TFA salt | 543.0 | 7.3 |
| 33 | 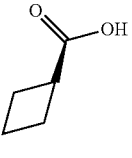 | (1S,3s)-3-((3R,4S)-4-hydroxy-7-(5-(3-phenyl-4-(trifluoromethyl) isoxazol-5-yl)-1,2,4-oxadiazol-3-yl)chroman-3-ylamino) cyclobutanecarboxylic acid, salt | 543.0 | 7.3 |
| 34 | 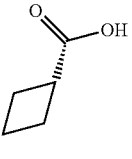 | 3-((3S,4R)-4-hydroxy-7-(5-(3-phenyl-4-(trifluoromethyl)isoxazol-5-yl)-1,2,4-oxadiazol-3-yl)chroman-3-ylamino)-2,2-dimethylpropanoic acid, TFA salt | 545.0 | 7.7 |

TABLE 2-continued

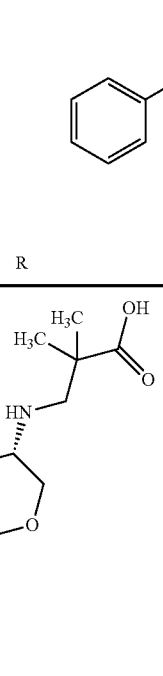

| Ex. | R | Name | Observed MS Ion (M + H)+ | RT<sup>a</sup> [min] |
|---|---|---|---|---|
| 35 | 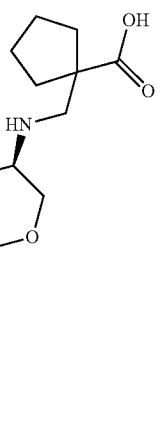 | 3-(((3R,4S)-4-hydroxy-7-(5-(3-phenyl-4-(trifluoromethyl)isoxazol-5-yl)-1,2,4-oxadiazol-3-yl)chroman-3-ylamino)-2,2-dimethylpropanoic acid, TFA salt | 545.0 | 7.7 |
| 36 | 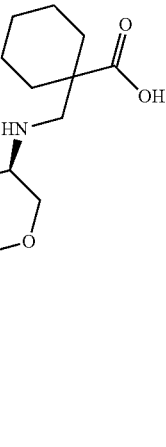 | 1-(((3S,4R)-4-hydroxy-7-(5-(3-phenyl-4-(trifluoromethyl)isoxazol-5-yl)-1,2,4-oxadiazol-3-yl)chroman-3-ylamino)methyl)cyclopentanecarboxylic acid, TFA salt | 571.1 | 8.0 |
| 37 | | 1-(((3S,4R)-4-hydroxy-7-(5-(3-phenyl-4-(trifluoromethyl)isoxazol-5-yl)-1,2,4-oxadiazol-3-yl)chroman-3-ylamino)methyl)cyclohexanecarboxylic acid, TFA salt | 585.1 | 8.2 |

TABLE 2-continued

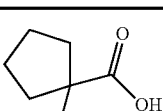

| Ex. | R | Name | Observed MS Ion (M + H)+ | RT$^a$ [min] |
|---|---|---|---|---|
| 38 | 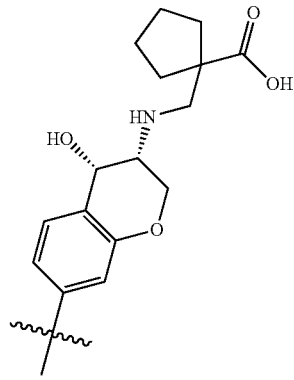 [SMILES: *c1ccc2c(c1)OC[C@@H](NCC1(C(=O)O)CCCC1)[C@H]2O] | 1-(((3R,4S)-4-hydroxy-7-(5-(3-phenyl-4-(trifluoromethyl)isoxazol-5-yl)-1,2,4-oxadiazol-3-yl)chroman-3-ylamino)methyl)cyclopentanecarboxylic acid, TFA salt | 571.1 | 8.0 |
| 39 | 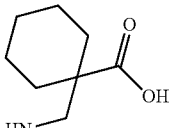 | 1-(((3R,4S)-4-hydroxy-7-(5-(3-phenyl-4-(trifluoromethyl)isoxazol-5-yl)-1,2,4-oxadiazol-3-yl)chroman-3-ylamino)methyl)cyclohexanecarboxylic acid, TFA salt | 585.1 | 8.2 |
| 40 | 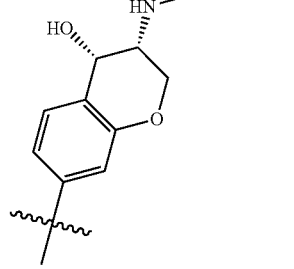 | 1-(((3S,4R)-4-hydroxy-7-(5-(3-phenyl-4-(trifluoromethyl)isoxazol-5-yl)-1,2,4-oxadiazol-3-yl)chroman-3-ylamino)methyl)cyclobutanecarboxylic acid, TFA salt | 557.0 | 7.8 |

TABLE 2-continued

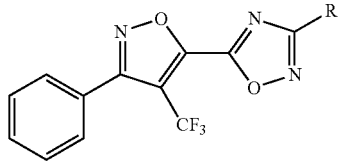

| Ex. | R | Name | Observed MS Ion (M + H)+ | RT$^a$ [min] |
|---|---|---|---|---|
| 41 | 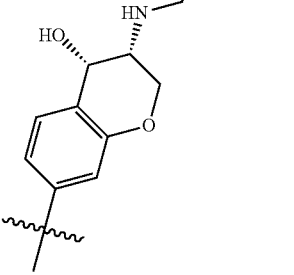 | 1-(((3R,4S)-4-hydroxy-7-(5-(3-phenyl-4-(trifluoromethyl)isoxazol-5-yl)-1,2,4-oxadiazol-3-yl)chroman-3-ylamino)methyl)cyclobutanecarboxylic acid, TFA salt | 557.0 | 7.8 |
| 42 | 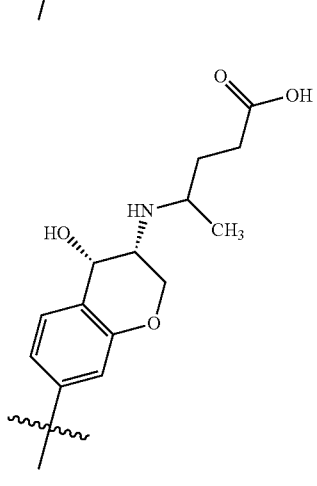 | 4,4'-((3R,4S)-4-hydroxy-7-(5-(3-phenyl-4-(trifluoromethyl)isoxazol-5-yl)-1,2,4-oxadiazol-3-yl)chroman-3-ylazanediyl)dibutanoic acid, TFA salt | 617.1 | 7.4 |
| 43 | | 4-((3R,4S)-4-hydroxy-7-(5-(3-phenyl-4-(trifluoromethyl)isoxazol-5-yl)-1,2,4-oxadiazol-3-yl)chroman-3-ylamino)pentanoic acid, TFA salt (first isomer off HPLC) | 545.1 | 7.3 |

TABLE 2-continued

| Ex. | R | Name | Observed MS Ion (M + H)+ | RT$^a$ [min] |
|---|---|---|---|---|
| 44 | (structure: pentanoic acid with CH₃ and chroman-hydroxy-amino group) | 4-((3R,4S)-4-hydroxy-7-(5-(3-phenyl-4-(trifluoromethyl)isoxazol-5-yl)-1,2,4-oxadiazol-3-yl)chroman-3-ylamino)pentanoic acid, TFA salt (second isomer off HPLC, diastereomer of Ex-43 at methyl) | 545.1 | 7.4 |
| 45 | (structure: 2-methylpropanoic acid with chroman-hydroxy-amino group) | 3-((3R,4S)-4-hydroxy-7-(5-(3-phenyl-4-(trifluoromethyl)isoxazol-5-yl)-1,2,4-oxadiazol-3-yl)chroman-3-ylamino)-2-methylpropanoic acid, TFA salt (first isomer off HPLC) | 531.0 | 7.5 |
| 46 | (structure: 2-methylpropanoic acid with chroman-hydroxy-amino group) | 3-((3R,4S)-4-hydroxy-7-(5-(3-phenyl-4-(trifluoromethyl)isoxazol-5-yl)-1,2,4-oxadiazol-3-yl)chroman-3-ylamino)-2-methylpropanoic acid, TFA salt (second isomer off HPLC, diastereomer of Ex-45, at methyl) | 531.1 | 7.4 |

$^a$Analytical HPLC using Method A

Example 47

Racemic (3R*,4S*)-7-(5-(3-phenyl-4-(trifluoromethyl)isoxazol-5-yl)-1,2,4-oxadiazol-3-yl)-3-(piperidin-1-yl)chroman-4-ol, TFA salt

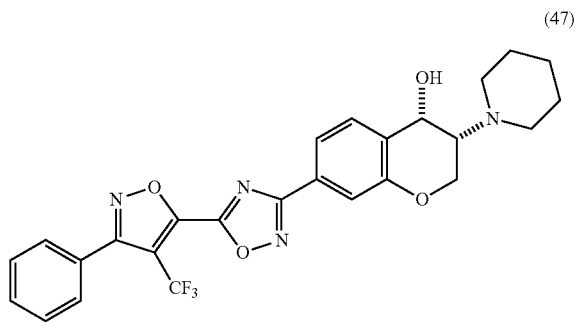 [SMILES: O[C@H]1c2ccc(-c3noc(-c4onc(-c5ccccc5)c4C(F)(F)F)n3)cc2OC[C@H]1N1CCCCC1]

(47)

Racemic (3R*,4S*)-3-amino-7-(5-(3-phenyl-4-(trifluoromethyl)isoxazol-5-yl)-1,2,4-oxadiazol-3-yl)chroman-4-ol, TFA salt (30 mg, 0.068 mmol) was dissolved in 1,2-dichloroethane (1000 µL) and tetrahydrofuran (500 µL). To this solution was added glacial acetic acid (11.58 µL, 0.203 mmol) and glutaraldehyde (12.22 µL, 0.068 mmol), which was followed by NaBH(OAc)$_3$ (28.6 mg, 0.13 mmol). The resulting solution was stirred for overnight before additional glacial acetic acid (7.7 µL) and NaBH(OAc)$_3$ (28.6 mg, 0.13 mmol) were added. This mixture was warmed to 50° C. and stirred for 6 h. After cooling, the resulting mixture was filtered and purified by preparative HPLC (PHENOMENEX® Luna 5u C18 21.2×100 mm, gradient elution with Method 1-MeOH/water containing 0.1% trifluoroacetic acid as defined above, 0% B to 100% B over 10 min, 20 mL/min, 220 nM) to give racemic (3R*,4S*)-7-(5-(3-phenyl-4-(trifluoromethyl)isoxazol-5-yl)-1,2,4-oxadiazol-3-yl)-3-(piperidin-1-yl)chroman-4-ol, TFA salt (2 mg): LCMS=513.0 [M+H]$^+$; $^1$H NMR (400 MHz, CD$_3$OD) δ ppm 7.85 (1H, dd, J=7.92, 1.54 Hz), 7.51-7.76 (7H, m), 5.22 (1H, d, J=1.10 Hz), 4.65-4.77 (1H, m), 4.44 (1H, t, J=10.78 Hz), 3.87-3.98 (1H, m), 3.69-3.85 (2H, m), 3.10-3.27 (2H, m), 1.47-2.16 (6H, m); HPLC Peak RT=9.4 min (Analytical Method A).

Examples 48-52

Examples 48-52 were prepared according to the general procedure described in Example 47.

TABLE 3

| Ex. | R | Name | Observed MS Ion (M + H)+ | RT$^a$ [min] |
|---|---|---|---|---|
| 48 | ![HO-piperidine-chroman] | Racemic-2-(1-((3R*,4S*)-4-hydroxy-7-(5-(3-phenyl-4-(trifluoromethyl)-isoxazol-5-yl)-1,2,4-oxadiazol-3-yl)chroman-3-yl)piperidin-3-yl)acetic acid, TFA salt (mixture of diastereomers at the piperidine center) | 571.0 | 9.0 |

TABLE 3-continued

[Structure: 3-phenyl-4-(trifluoromethyl)isoxazol-5-yl linked to 1,2,4-oxadiazole with R substituent at 3-position]

| Ex. | R | Name | Observed MS Ion (M + H)+ | RT$^a$ [min] |
|---|---|---|---|---|
| 49 | [Structure: chroman-piperidinyl-acetic acid with HO groups] | 2-(-1-((3R,4S)-4-hydroxy-7-(5-(3-phenyl-4-(trifluoromethyl)isoxazol-5-yl)-1,2,4-oxadiazol-3-yl)chroman-3-yl)piperidin-3-yl)acetic acid, TFA salt (first isomer off HPLC, diastereomer of Ex-50, at piperidine center) | 571.0 | 8.9 |
| 50 | [Structure: chroman-piperidinyl-acetic acid with HO groups] | 2-(-1-((3R,4S)-4-hydroxy-7-(5-(3-phenyl-4-(trifluoromethyl)isoxazol-5-yl)-1,2,4-oxadiazol-3-yl)chroman-3-yl)piperidin-3-yl)acetic acid (second isomer off HPLC, diastereomer of Ex-49, at piperidine center) | 571.0 | 9.0 |
| 51 | [Structure: chroman-piperidinyl-acetic acid with HO groups] | 2-(-1-((3S,4R)-4-hydroxy-7-(5-(3-phenyl-4-(trifluoromethyl)isoxazol-5-yl)-1,2,4-oxadiazol-3-yl)chroman-3-yl)piperidin-3-yl)acetic acid, TFA salt (first isomer off HPLC, diastereomer of Ex-52, at piperidine center) | 571.0 | 9.0 |

TABLE 3-continued

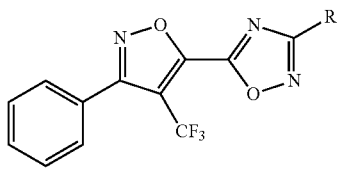

| Ex. | R | Name | Observed MS Ion (M + H)+ | RT[a] [min] |
|---|---|---|---|---|
| 52 | HO<br>O | 2-(-1-((3S,4R)-4-hydroxy-7-(5-(3-phenyl-4-(trifluoromethyl)isoxazol-5-yl)-1,2,4-oxadiazol-3-yl)chroman-3-yl)piperidin-3-yl)acetic acid, TFA salt (second isomer off HPLC, diastereomer of Ex-51, at piperidine center) | 571.0 | 9.1 |

[a] Analytical HPLC using Method A

Example 53

3-((3R,4S)-4-Hydroxy-7-(5-(3-phenyl-4-(trifluoromethyl)isoxazol-5-yl)-1,2,4-oxadiazol-3-yl)chroman-3-ylamino)propanoic acid, TFA salt (53)

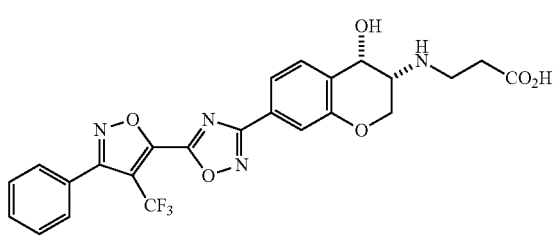

(3R,4S)-3-Amino-7-(5-(3-phenyl-4-(trifluoromethyl)isoxazol-5-yl)-1,2,4-oxadiazol-3-yl)chroman-4-ol Ex 9 (80 mg, 0.18 mmol) was dissolved in 2-propanol (1.8 ml). To this solution was added TEA (125 µl, 0.9 mmol) and tert-butyl acrylate (105 µl, 0.72 mmol). The solution was stirred at 80° C. for 3 days. After cooling, the solvent was evaporated and the resulting residue was redissolved in $CH_2Cl_2$ (1 mL). To this solution was added TFA (0.5 mL). After 2 h, the solution was mixed with MeCN and purified by preparative HPLC (Column: PHENOMENEX® Luna C18, 5-mm particles (30×100 mm; Guard Column: none; Mobile Phase A: 5:95 acetonitrile:water with 0.1% TFA; Mobile Phase B: 95:5 acetonitrile:water with 0.1% TFA; Gradient: 15%-100% B over 10 minutes; Flow: 30 mL/min, uv detection 254 nM) to give 3-((3R,4S)-4-hydroxy-7-(5-(3-phenyl-4-(trifluoromethyl)isoxazol-5-yl)-1,2,4-oxadiazol-3-yl)chroman-3-ylamino)propanoic acid, TFA salt Ex 53 (18 mg): LCMS $[M+H]^+=517.0$; $^1H$ NMR (400 MHz, $CH_3OD$) δ ppm 7.90 (1H, dd, J=8.03, 1.65 Hz), 7.60-7.76 (7H, m), 5.21 (1H, d, J=4.40 Hz), 4.46-4.57 (2H, m), 3.91 (1H, ddd, J=7.81, 4.07, 3.96 Hz), 3.50-3.65 (2H, m), 2.89 (2H, t, J=6.82 Hz); HPLC Peak RT=8.7 min (Analytical Method A).

Examples 54-56

Examples 54-56 were prepared according to the general procedure described in Example 53.

TABLE 4

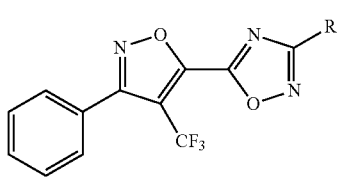

| Ex | R | Name | Observed MS Ion (M + H)+ | RTa [min] |
|---|---|---|---|---|
| 54 | 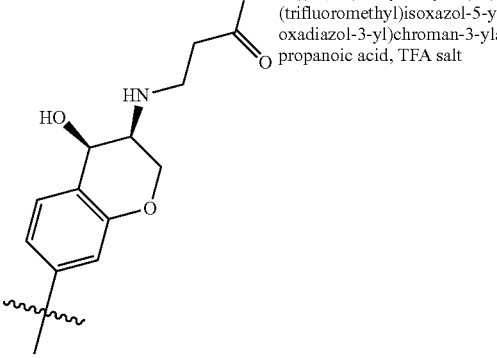 OH | 3-((3S,4R)-4-hydroxy-7-(5-(3-phenyl-4-(trifluoromethyl)isoxazol-5-yl)-1,2,4-oxadiazol-3-yl)chroman-3-ylamino)-propanoic acid, TFA salt | 517.0 | 8.7 |
| 55 | OH | Racemic-3-(1-hydroxy-5-(5-(3-phenyl-4-(trifluoromethyl)isoxazol-5-yl)-1,2,4-oxadiazol-3-yl)-2,3-dihydro-1H-inden-2-ylamino)propanoic acid, TFA salt | 501.2 | 8.6 |
| 56 | OH | Racemic-3-(1-hydroxy-6-(5-(3-phenyl-4-(trifluoromethyl)isoxazol-5-yl)-1,2,4-oxadiazol-3-yl)-1,2,3,4-tetrahydronaphthalen-2-ylamino)-propanoic acid, TFA salt | 515.2 | 8.7 |

[a] Analytical HPLC using Method A

Example 57

(1S,3 S)-3 #3R,4S)-4-Hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt (57)

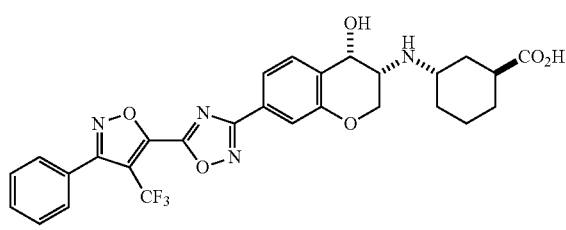

(3R,4S)-3-Amino-7-(5-(3-phenyl-4-(trifluoromethyl)isoxazol-5-yl)-1,2,4-oxadiazol-3-yl)chroman-4-ol, TFA salt Ex-9 (209 mg, 0.47 mmol) was dissolved in CHCl$_3$ (4.7 mL). To this solution was added TEA (0.25 mL, 1.9 mmol) and Int-8A (12.22 µL, 0.068 mmol), which was followed by NaBH(OAc)$_3$ (399 mg, 1.9 mmol). The resulting solution was stirred for overnight before chiral preparative SFC (Column: AS-H, 30×250 mm, isocratic elution with mobile phase 20% MeOH+0.1% DEA in CO$_2$, 85 mL/min, 250 nM) gave (4R,5S)-3-((1S,3R)-3-((3R,4S)-4-hydroxy-7-(5-(3-phenyl-4-(trifluoromethyl)isoxazol-5-yl)-1,2,4-oxadiazol-3-yl)chroman-3-ylamino)cyclohexanecarbonyl)-4-methyl-5-phenyloxazolidin-2-one (35 mg, LCMS=730.2 [M+H]$^+$) as the first peak (retention=9.1 min) and (4R,5S)-3-((1S,3S)-3-((3R,4S)-4-hydroxy-7-(5-(3-phenyl-4-(trifluoromethyl)isoxazol-5-yl)-1,2,4-oxadiazol-3-yl)chroman-3-ylamino)cyclohexanecarbonyl)-4-methyl-5-phenyloxazolidin-2-one (35 mg, LCMS=730.2 [M+H]$^+$) as the second peak (retention=11.2 min) (4R,5S)-3-((1S,3S)-3-((3R,4S)-4-hydroxy-7-(5-(3-phenyl-4-(trifluoromethyl)isoxazol-5-yl)-1,2,4-oxadiazol-3-yl)chroman-3-ylamino)cyclohexanecarbonyl)-4-methyl-5-phenyloxazolidin-2-one (100 mg, 0.14 mmol) was dissolved in THF (1.9 mL). To this solution was added H$_2$O$_2$ (56.0 µl, 0.55 mmol) and 0.5 M LiOH (548 µl, 0.274 mmol) at 0° C. The resulting solution was stirred at 0° C. for 1 h. The reaction was then quenched by addition of saturated Na$_2$SO$_3$ solution. The reaction mixture was stirred overnight at room temperature. Next, 1N HCl and saturated NaHCO$_3$ solutions were added to adjust the pH=9. The resulting solution was stirred at room temperature for 1.5 h and then was extracted with EtOAc twice. Organic layer was concentrated and preparative HPLC (Column: PHENOMENEX® Luna C18, 5-µm particles, 30×100 mm; Guard Column: none; Mobile Phase A: 5:95 acetonitrile:water with 0.1% TFA; Mobile Phase B: 95:5 acetonitrile:water with 0.1% TFA; Gradient: 15%-100% B over 10 minutes; Flow: 30 mL/min, uv detection 254 nM) gave (1S,3S)-3-((3R,4S)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt Ex 57 (3.5 mg): LCMS=571.1 [M+H]$^+$; $^1$H NMR (400 MHz, CD$_3$OD) δ ppm 7.88 (1H, dd, J=7.92, 1.32 Hz), 7.60-7.76 (7H, m), 5.12 (1H, d, J=3.08 Hz), 4.42-4.55 (2H, m), 4.01-4.10 (1H, m), 3.79 (1H, d, J=6.82 Hz), 3.04 (1H, br. s.), 2.60 (1H, d, J=11.22 Hz), 2.15-2.33 (2H, m), 1.87 (1H, br. s.), 1.46-1.79 (4H, m); HPLC Peak RT=7.63 min (Analytical Method A).

Examples 58-66

Examples 58-66 were prepared according to the general procedure described in Example 57.

TABLE 5

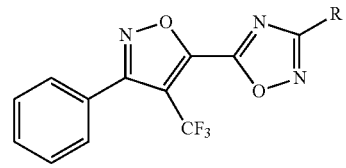

| Ex. | R | Name | Observed MS Ion (M + H)$^+$ | RT$^a$ [min] |
|---|---|---|---|---|
| 58 | 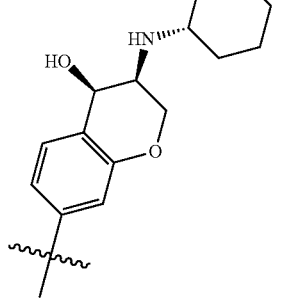 | (1R,3S)-3-((3S,4R)-4-hydroxy-7-(5-(3-phenyl-4-(trifluoromethyl)isoxazol-5-yl)-1,2,4-oxadiazol-3-yl)chroman-3-ylamino)cyclohexanecarboxylic, TFA salt | 571.0 | 8.8 |

TABLE 5-continued

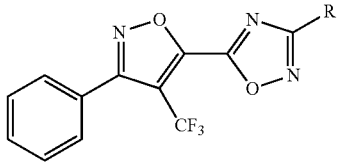

| Ex. | R | Name | Observed MS Ion (M + H)+ | RT$^a$ [min] |
|---|---|---|---|---|
| 59 | 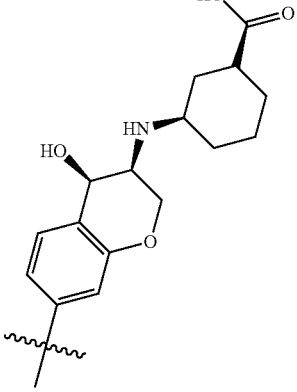 | (1R,3R)-3-((3S,4R)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt | 571.0 | 8.7 |
| 60 | 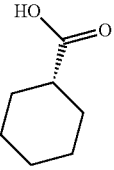 | (1R,3R)-3-((3S,4R)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid | 571.0 | 8.8 |
| 61 | 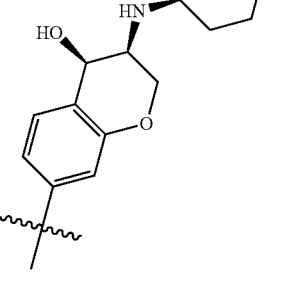 | (1S,4S)-4-((3R,4S)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt | 571.0 | 8.8 |

TABLE 5-continued

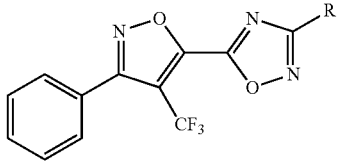

| Ex. | R | Name | Observed MS Ion (M + H)⁺ | RT^a [min] |
|---|---|---|---|---|
| 62 | 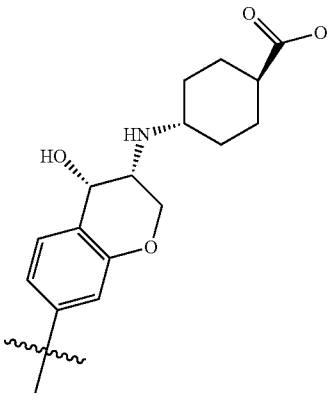 | (1R,4R)-4-((3R,4S)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt | 571.0 | 8.7 |
| 63 | 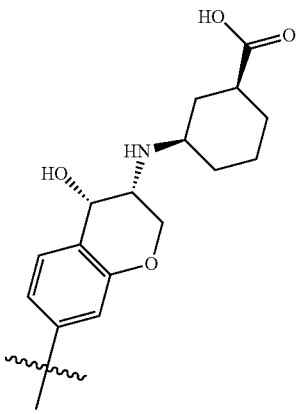 [SMILES: *c1ccc2c(c1)OC[C@@H](N[C@@H]1CCC[C@H](C(=O)O)C1)[C@H]2O] | (1R,3S)-3-((3S,4R)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt | 571.0 | 8.8 |
| 64 | 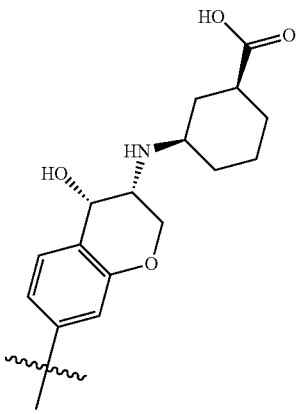 [SMILES: *c1ccc2c(c1)OC[C@@H](N[C@@H]1CCC[C@H](C(=O)O)C1)[C@H]2O] | (1S,3R)-3-((3R,4S)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt | 571.0 | 7.5 |

TABLE 5-continued

| Ex. | R | Name | Observed MS Ion (M + H)+ | RT[a] [min] |
|---|---|---|---|---|
| 65 | (structure: cyclohexanecarboxylic acid with chromanol-HN linker) | (1R,3R)-3-((3R,4S)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, salt | 571.0 | 7.5 |
| 66 | (structure: cyclohexanecarboxylic acid with chromanol-HN linker) | (1R,3S)-3-((3R,4S)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt | 571.0 | 7.4 |

[a]Analytical HPLC using Method A

Example 67

2-((3S,4R)-4-Hydroxy-7-(5-(3-phenyl-4-(trifluoromethyl)isoxazol-5-yl)-1,2,4-oxadiazol-3-yl)chroman-3-ylamino)acetic acid, TFA salt

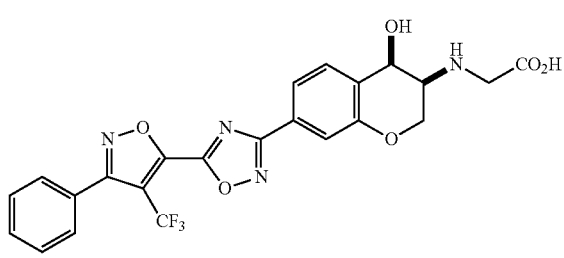

(67)

(3S,4R)-4-(tert-Butyldimethylsilyloxy)-7-(5-(3-phenyl-4-(trifluoromethyl)isoxazol-5-yl)-1,2,4-oxadiazol-3-yl)chroman-3-amine (50 mg, 0.09 mmol) was dissolved in acetonitrile (716 µl). To this solution was added $K_2CO_3$ (12.4 mg, 0.09 mmol) and tert-butyl 2-bromoacetate (15.9 µl, 0.11 mmol). The resulting solution was stirred at room temperature overnight. This was diluted with DMF and filtered to remove solid material and was purified by preparative HPLC (PHENOMENEX® Luna 5u C18 21×250 mm, gradient elution with Method 1-MeOH/water containing 0.1% trifluoroacetic acid as defined above, 0% B to 100% B over 10 min, 20 mL/min, 220 nM) to give tert-butyl 2-((3S,4R)-4-(tert-butyldimethylsilyloxy)-7-(5-(3-phenyl-4-(trifluoromethyl)isoxazol-5-yl)-1,2,4-oxadiazol-3-yl)chroman-3-ylamino)acetate (LCMS [M+H]+=673.3), which was dissolved in $CH_2Cl_2$ (4 mL) and TFA (1.5 mL). This solution was stirred for 2 h before it was concentrated. The resulting residue was dissolved in 4 N HCl in dioxane (1.0 mL) and 6 N HCl aqueous solution (0.5 mL) and stirred overnight. Next, the reaction was stirred at 50° C. for 4 h. After cooling, the solution was mixed with MeCN and purified by preparative HPLC (Column: PHENOMENEX® Luna C18, 5-μm particles (30×100 mm; Guard Column: none; Mobile Phase A: 5:95 acetonitrile:water with 0.1% TFA; Mobile Phase B: 95:5 acetonitrile:water with 0.1% TFA; Gradient: 15%-100% B over 10 minutes; Flow: 30 mL/min, uv detection 254 nM) to give 2-((3S,4R)-4-hydroxy-7-(5-(3-phenyl-4-(trifluoromethyl)isoxazol-5-yl)-1,2,4-oxadiazol-3-yl)chroman-3-ylamino)acetic acid, TFA salt Ex 67 (44.5 mg): LCMS [M+H]$^+$=503.0; $^1$H NMR (400 MHz, CD$_3$OD) δ ppm 7.89 (1H, dd, J=8.03, 1.65 Hz), 7.60-7.76 (8H, m), 5.17 (1H, d, J=4.18 Hz), 4.44-4.58 (2H, m), 4.06 (2H, d, J=2.64 Hz), 3.90-3.97 (1H, m); HPLC Peak RT=7 5 min (Analytical Method A).

Examples 68-72

Examples 68-72 were prepared according to the general procedure described in Example 67.

TABLE 6

| Ex. | R | Name | Observed MS Ion (M + H)$^+$ | RT$^a$ [min] |
|---|---|---|---|---|
| 68 | (carboxymethylamino group) | 2-((3R,4S)-4-hydroxy-7-(5-(3-phenyl-4-(trifluoromethyl)isoxazol-5-yl)-1,2,4-oxadiazol-3-yl)chroman-3-ylamino)-acetic acid, TFA salt | 503.0 | 7.5 |
| 69 | (carboxypropylamino group) | 4-((3R,4S)-4-hydroxy-7-(5-(3-phenyl-4-(trifluoromethyl)isoxazol-5-yl)-1,2,4-oxadiazol-3-yl)chroman-3-ylamino)-butanoic acid, TFA salt | 531.0 | 7.4 |

TABLE 6-continued

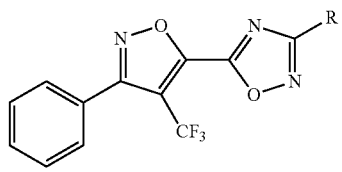

| Ex. | R | Name | Observed MS Ion (M + H)+ | RT<sup>a</sup> [min] |
|---|---|---|---|---|
| 70 | (structure: HO-chroman-HN-CH2CH2CH2-C(=O)OH) | 4-((3S,4R)-4-hydroxy-7-(5-(3-phenyl-4-(trifluoromethyl)isoxazol-5-yl)-1,2,4-oxadiazol-3-yl)chroman-3-ylamino)-butanoic acid, TFA salt | 531.0 | 7.4 |
| 71 | (structure: HO-tetrahydronaphthalen-HN-CH2-C(=O)OH) | Racemic-2-(1-hydroxy-6-(5-(3-phenyl-4-(trifluoromethyl)isoxazol-5-yl)-1,2,4-oxadiazol-3-yl)-1,2,3,4-tetrahydronaphthalen-2-ylamino)acetic acid, TFA salt | 501.1 | 8.7 |
| 72 | (structure: HO-tetrahydronaphthalen-HN-CH2CH2CH2-C(=O)OH) | Racemic-4-(1-hydroxy-6-(5-(3-phenyl-4-(trifluoromethyl)isoxazol-5-yl)-1,2,4-oxadiazol-3-yl)-1,2,3,4-tetrahydronaphthalen-2-ylamino)-butanoic acid, TFA salt | 529.1 | 8.9 |

<sup>a</sup>Analytical HPLC using Method A

Biological Assays

S1P1 Binding Assay

Membranes were prepared from CHO cells expressing human $S1P_1$. Cells were dissociated in buffer containing 20 mM HEPES, pH 7.5, 50 mM NaCl, 2 mM EDTA and Protease Inhibitor cocktail (Roche), and disrupted on ice using the Polytron homogenizer. The homogenate was centrifuged at 20,000 rpm (48,000 G) and the supernatant was discarded. The membrane pellets were resuspended in buffer containing 50 mM HEPES, pH 7.5, 100 mM NaCl, 1 mM $MgCl_2$, 2 mM EDTA and stored in aliquots at −80° C. after protein concentration determination.

Membranes (2 μg/well) and 0.03 nM final concentration of 33P-S1P ligand (1 mCi/ml, American Radiolabeled Chemicals) were added to the compound plates. Binding was performed for 45 minutes at room temperature, terminated by collecting the membranes onto GF/B filter plates, and radioactivity was measured by TOPCOUNT®. The competition data of the test compounds over a range of concentrations was plotted as percentage inhibition of radioligand specific binding. The $IC_{50}$ is defined as the concentration of competing ligand needed to reduce specific binding by 50%.

Table A below lists $S1P_1$ Binding $IC_{50}$ values from the following examples of this invention measured in the $S1P_1$ binding assay described hereinabove. The results in Table A were rounded to two digits.

TABLE A

| Ex. | $S1P_1$ Binding $IC_{50}$ (nM) |
|---|---|
| 4 | 23 |
| 5 | 12 |
| 9 | 39 |
| 13 | 630 |
| 25 | 24 |
| 30 | 13 |
| 39 | 541 |
| 41 | 20 |
| 50 | 57 |
| 53 | 14 |
| 57 | 0.7 |
| 65 | 6.6 |
| 68 | 3.8 |

Receptor [35S] GTPγS Binding Assays

Compounds were loaded in a 384 FALCON® v-bottom plate (0.5 μl/well in a 3-fold dilution). Membranes prepared from $S1P_1$/CHO cells or EDG3-Ga15-bla HEK293T cells were added to the compound plate (40 μl/well, final protein 3 μg/well) with MULTIDROP®. [$^{35}$S]GTP (1250 Ci/mmol, Perkin Elmer) was diluted in assay buffer: 20 mM HEPES, pH7.5, 10 mM $MgCl_2$, 150 mM NaCl, 1 mM EGTA, 1 mM DTT, 10 μM GDP, 0.1% fatty acid free BSA, and 10 μg/ml Saponin to 0.4 nM. 40 μl of the [$^{35}$S] GTP solution was added to the compound plate with a final concentration of 0.2 nM. The reaction was kept at room temperature for 45 min. At the end of incubation, all the mixtures in the compound plate were transferred to a 384 well FB filter plates via GPCR robot system. The filter plate was washed with water 4 times by using the modified manifold Embla plate washer and dried at 60° C. for 45 min. 30 μl of MicroScint 20 scintillation fluid was added to each well for counting at Packard TOP-COUNT®. $EC_{50}$ is defined as the agonist concentration that corresponds to 50% of the Ymax (maximal response) obtained for each individual compound tested.

TABLE B

| Ex. | GTPγS $S1P_1$ $EC_{50}$ (nM) | GTPγS $S1P_3$ $EC_{50}$ (nM) |
|---|---|---|
| 4 | 80 | 13000 |
| 5 | 8.1 | 25000 |
| 9 | 33 | 8600 |
| 13 | 160 | 31000* |
| 25 | 7.8 | 12000 |
| 30 | 6.5 | 8000 |
| 39 | 85 | 31000* |
| 41 | 16 | 8400 |
| 50 | 27 | 24000 |
| 53 | 6.0 | 22000 |
| 57 | 1.0 | 7300 |
| 65 | 1.1 | 11000 |
| 68 | 5.4 | 5200 |

*Detection limit was 31250 nM in the GTPγS $S1P_3$ assay.

A smaller value for GTPγS $S1P_1$ $EC_{50}$ value indicated greater activity for the compound in the GTPγS S1P1 binding assay. A larger value for the GTPγS S1P3 $EC_{50}$ value indicated less activity in the GTPγS S1P3 binding assay.

The compounds of the present invention, as exemplified by examples in Table B showed GTPγS S1P1 $EC_{50}$ values of less than 5 μM.

The ratios of the GTPγS $S1P_3$ $EC_{50}$ values to the GTPγS S1P1 $EC_{50}$ values, calculated from the data in Table B, are shown in Table C.

TABLE C

| Ex. | GTPγS $S1P_3$/$S1P_1$ |
|---|---|
| 4 | 160 |
| 5 | 3100 |
| 9 | 260 |
| 13 | 200* |
| 25 | 1500 |
| 30 | 1200 |
| 39 | 370* |
| 41 | 510 |
| 50 | 870 |
| 53 | 3700 |
| 57 | 7300 |
| 65 | 9600 |
| 68 | 960 |

*Note detection limit was 31250 nM for GTPγS $S1P_3$.

In Table C, a larger value for the ratio of the GTPγS $S1P_3$ $EC_{50}$ value to the GTPγS $S1P_1$ $EC_{50}$ value indicates greater selectivity of $S1P_1$ activity over $S1P_3$ activity.

The compounds of the present invention, as exemplified by examples in Table C, show the surprising advantage as agonists of $S1P_1$ and are selective over $S1P_3$.

The compounds of the present invention possess activity as agonists of $S1P_1$ and are selective over $S1P_3$, and thus may be used in treating, preventing, or curing various $S1P_1$ receptor-related conditions while reducing or minimizing the side effects due to $S1P_3$ activity. The surprising selectivity of the compounds of the present invention indicate their potential use in treating, preventing, or curing autoimmune and inflammatory diseases such as multiple sclerosis, rheumatoid arthritis, inflammatory bowel disease, or psoriasis, while reducing or minimizing possible cardiovascular side effects such as bradycardia and hypertension. Other potential uses of the compounds of the present invention include minimizing or reducing rejection of transplanted organs, while reducing or minimizing side effects due to $S1P_3$ activity.

Blood Lymphocyte Reduction Assay (BLR) in Rodents

Lewis rats were dosed orally with test article (as a solution or suspension in the vehicle) or vehicle alone (polyethylene glycol 300, "PEG300"). Blood was drawn at 4 hr by retro-orbital bleeding. Blood lymphocyte counts were determined on an ADVIA® 120 Hematology Analyzer (Siemens Healthcare Diagnostics). The results were measured as a reduction in the percentage of circulating lymphocytes as compared to the vehicle treated group at the 4 hr measurement. The results represent the average results of all animals within each treatment group (n=3-4).

The following examples were tested in the Blood Lymphocyte Reduction assay (BLR) described herein above and the results are shown in Table D for rats.

TABLE D

| Ex. | Dose (mg/kg) | % Reduction in Lymphocytes at 4 hr. |
|---|---|---|
| 25 | 3 | 93 |
| 41 | 0.5 | 11 |
| 57 | 0.5 | 69 |
| 65 | 0.5 | 55 |

What is claimed is:
1. A compound of Formula (I):

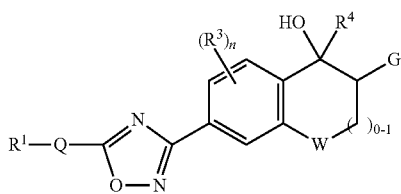

or a pharmaceutically acceptable salt thereof, wherein:
W is $CH_2$ or O;
Q is

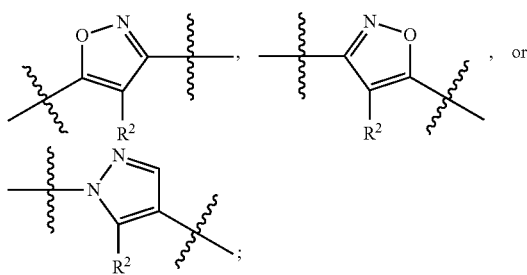

$R^1$ is:
(i) $C_{3-6}$alkyl;
(ii) $C_{3-7}$cycloalkyl substituted with zero to 3 substituents independently selected from halo, —CN, $C_{1-4}$alkyl, $C_{1-4}$alkoxy, $C_{1-3}$fluoroalkyl, $C_{1-3}$chloroalkyl, and/or $C_{1-2}$fluoroalkoxy;
(iii) phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy; or
(iv) pyridinyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy;
$R^2$ is $C_{1-6}$alkyl, $C_{1-3}$fluoroalkyl, $C_{3-7}$cycloalkyl, or phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy;

n is zero, 1, or 2;
each $R^3$ is independently $C_{1-3}$alkyl, F, Cl, $C_{1-3}$fluoroalkyl, $C_{1-3}$chloroalkyl, —CN, $C_{1-3}$alkoxy, and/or $C_{1-3}$fluoroalkoxy;
$R^4$ is H or —$CH_3$;
G is:
(i) —$NR^aR^a$;
(ii) —$NH(CR^dR^d)_{1-3}C(O)OR^a$, —$NH(CR^dR^d)_{1-4}OH$, —$NHR^e$, or $NR^eR^e$;
(iii) —$NH(CR^dR^d)_{1-3}CR^bR^cC(O)OR^a$, wherein $R^b$ and $R^c$ together with the carbon atom to which they are attached form a $C_{3-6}$spirocycloalkyl ring;
(iv) —$NR^a[(CR^aR^a)_{0-3}(C_{3-6}$cycloalkyl)], wherein said $C_{3-6}$cycloalkyl is substituted with zero to 2 substituents independently selected from —$(CR^dR^d)_{1-3}C(O)OR^a$ and/or —$(CR^dR^d)_{1-4}OH$;
(v) 5- to 6-membered heterocyclyl having at least one nitrogen heteroatom, wherein said heterocyclyl is substituted with zero to 2 substituents independently selected from —$(CR^dR^d)_{0-3}C(O)OR^a$ and/or —$(CR^dR^d)_{0-4}OH$; or
(vi) —$NR^aC(O)OR^a$;
each $R^a$ is independently H, $C_{1-4}$alkyl, and/or $C_{1-3}$hydroxyalkyl;
each $R^d$ is independently H, —OH, F, and/or —$CH_3$; and
each $R^e$ is independently —$(CR^aR^a)_{1-3}C(O)OR^a$.
2. The compound according to claim 1 of Formula (III):

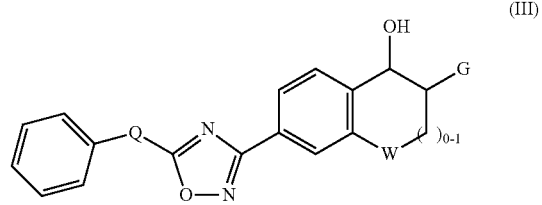

or a pharmaceutically acceptable salt thereof, wherein:
$R^2$ is —$CF_3$; and
G is:
(i) —$NR^aR^a$;
(ii) —$NH(CR^dR^d)_{1-3}C(O)OR^a$, —$NHR^e$, or $NR^eR^e$;
(iii) —$NH(CH_2)_{1-3}CR^bR^cC(O)OR^a$, wherein $R^b$ and $R^c$ together with the carbon atom to which they are attached form a $C_{3-6}$spirocycloalkyl ring;
(iv) —$NR^a[(CR^aR^a)_{0-2}(C_{4-6}$cycloalkyl)], wherein said $C_{4-6}$cycloalkyl is substituted with zero to 2 substituents independently selected from —$(CR^dR^d)_{1-3}C(O)OR^a$ and/or —$(CR^dR^d)_{1-4}OH$;
(v) piperidinyl, piperazinyl, or morpholinyl, each substituted with zero to 2 substituents independently selected from —$(CR^dR^d)_{0-3}C(O)OR^a$ and/or —$(CR^dR^d)_{0-4}OH$; or
(vi) —$NR^aC(O)OR^a$;
each $R^a$ is independently H and/or $C_{1-4}$alkyl; and
each $R^e$ is independently —$(CH_2)_{1-3}C(O)OR^a$.

3. The compound according to claim 2 having Formula (IIIa):

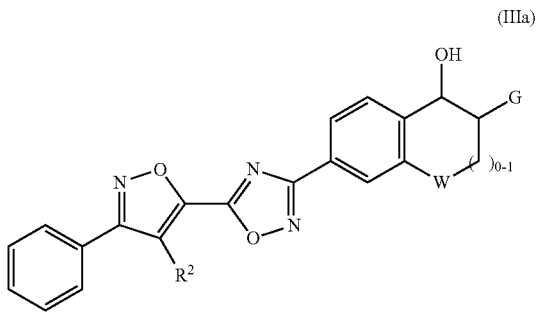

or a pharmaceutically acceptable salt thereof, wherein:
G is:
(i) —NR$^a$R$^a$;
(ii) —NH(CR$^d$R$^d$)$_{1-3}$C(O)OR$^a$, —NHR$^e$, or NR$^e$R$^e$;
(iii) —NH(CH$_2$)$_{1-3}$CR$^b$R$^e$C(O)OR$^a$, wherein R$^b$ and R$^e$ together with the carbon atom to which they are attached form a C$_{3-6}$spirocycloalkyl ring;
(iv) —NR$^a$(C$_{4-6}$cycloalkyl), wherein said C$_{4-6}$cycloalkyl is substituted with zero to 1 substituent selected from —(CH$_2$)$_{1-3}$C(O)OR$^a$;
(v) piperidinyl substituted with zero to 1 substituent selected from —(CH$_2$)$_{0-3}$C(O)OR$^a$; or
(vi) —NR$^a$C(O)OR$^a$; and
each R$^d$ is independently H and/or —CH$_3$.

4. The compound according to claim 3 having Formula (IVc):

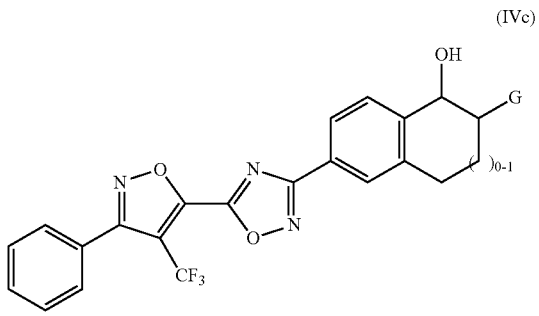

or a pharmaceutically acceptable salt thereof, wherein:
G is —NH$_2$ or —NH(CH$_2$)$_{1-2}$C(O)OH.

5. The compound according to claim 3 having Formula (Vd):

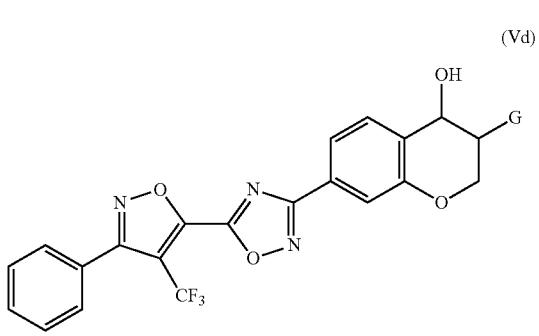

or a pharmaceutically acceptable salt thereof, wherein:

G is:
(i) —NHR$^a$ or —N(CH$_3$)$_2$;
(ii) —NH(CH$_2$)$_{1-3}$—C(O)OR$^a$, —NHCH$_2$CH(CH$_3$)C(O)OR$^a$, —NHCH$_2$C(CH$_3$)$_2$C(O)OR$^a$, —NHCH(CH$_3$)(CH$_2$)$_{1-2}$C(O)OR$^a$, or —N(CH$_2$CH$_2$CH$_2$C(O)OH)$_2$;
(iii) —NHCH$_2$CR$^b$R$^c$C(O)OR$^a$, wherein R$^b$ and R$^c$ together with the carbon atom to which they are attached form a C$_{3-6}$spirocycloalkyl ring;
(iv) —NH(C$_{4-6}$cycloalkyl), wherein said C$_{4-6}$cycloalkyl is substituted with zero to 1 substituent selected from —C(O)OR$^a$;
(v) piperidinyl substituted with zero to 1 substituent selected from —CH$_2$C(O)OR$^a$; or
(vi) —NHC(O)O(C$_{1-4}$alkyl).

6. The compound according to claim 1 or a pharmaceutically acceptable salt thereof, wherein said compound is selected from: racemic (3R*,4S*)-3-amino-7-(5-(3-phenyl-4-(trifluoromethyl)isoxazol-5-yl)-1,2,4-oxadiazol-3-yl) chroman-4-ol, TFA salt (1); racemic-2-amino-5-(5-(3-phenyl-4-(trifluoromethyl)isoxazol-5-yl)-1,2,4-oxadiazol-3-yl)-2,3-dihydro-1H-inden-1-ol, TFA salt (2); racemic-2-amino-6-(5-(3-phenyl-4-(trifluoromethyl)isoxazol-5-yl)-1,2,4-oxadiazol-3-yl)-1,2,3,4-tetrahydronaphthalen-1-ol, TFA salt (3); racemic (3R*,4R*)-3-amino-7-(5-(3-phenyl-4-(trifluoromethyl)isoxazol-5-yl)-1,2,4-oxadiazol-3-yl)chroman-4-ol, TFA salt (4); racemic 3-((3R*,4R*)-4-hydroxy-7-(5-(3-phenyl-4-(trifluoromethyl)isoxazol-5-yl)-1,2,4-oxadiazol-3-yl)chroman-3-ylamino)propanoic acid, TFA salt (5); racemic (3R*,4S*)-tert-butyl-4-hydroxy-7-(5-(3-phenyl-4-(trifluoromethyl)isoxazol-5-yl)-1,2,4-oxadiazol-3-yl)chroman-3-ylcarbamate (6 and 7); (3S,4R)-3-amino-7-(5-(3-phenyl-4-(trifluoromethyl)isoxazol-5-yl)-1,2,4-oxadiazol-3-yl) chroman-4-ol, TFA salt (8); (3R,4S)-3-amino-7-(5-(3-phenyl-4-(trifluoromethyl)isoxazol-5-yl)-1,2,4-oxadiazol-3-yl)chroman-4-ol, TFA salt (9); racemic (3R*,4S*)-3-(isopropylamino)-7-(5-(3-phenyl-4-(trifluoromethyl)isoxazol-5-yl)-1,2,4-oxadiazol-3-yl)chroman-4-ol (10); racemic cis-3-(cyclohexylamino)-7-(5-(3-phenyl-4-(trifluoromethyl)isoxazol-5-yl)-1,2,4-oxadiazol-3-yl)chroman-4-ol, TFA salt (11); racemic 3-((3R*,4S*)-4-hydroxy-7-(5-(3-phenyl-4-(trifluoromethyl)isoxazol-5-yl)-1,2,4-oxadiazol-3-yl)chroman-3-ylamino)butanoic acid, TFA salt (12); racemic-ethyl 3-((3R*,4S*)-4-hydroxy-7-(5-(3-phenyl-4-(trifluoromethyl)isoxazol-5-yl)-1,2,4-oxadiazol-3-yl)chroman-3-ylamino)cyclohexanecarboxylate, TFA salt (13); racemic-ethyl 4-((3R*,4S*)-4-hydroxy-7-(5-(3-phenyl-4-(trifluoromethyl)isoxazol-5-yl)-1,2,4-oxadiazol-3-yl)chroman-3-ylamino)cyclohexanecarboxylate, TFA salt (14); racemic-3-((3R*,4S*)-4-hydroxy-7-(5-(3-phenyl-4-(trifluoromethyl)isoxazol-5-yl)-1,2,4-oxadiazol-3-yl)chroman-3-ylamino)cyclohexanecarboxylic acid, TFA salt (15); racemic-4-((3R*,4S*)-4-hydroxy-7-(5-(3-phenyl-4-(trifluoromethyl)isoxazol-5-yl)-1,2,4-oxadiazol-3-yl) chroman-3-ylamino)cyclohexanecarboxylic acid, TFA salt (16); racemic-(3R*,4S*)-3-(dimethylamino)-7-(5-(3-phenyl-4-(trifluoromethyl)isoxazol-5-yl)-1,2,4-oxadiazol-3-yl) chroman-4-ol (17); racemic-(3R*,4S*)-3-(cyclobutylamino)-7-(5-(3-phenyl-4-(trifluoromethyl)isoxazol-5-yl)-1,2,4-oxadiazol-3-yl)chroman-4-ol, TFA salt (18); racemic-(3R*,4S*)-3-(cyclopentylamino)-7-(5-(3-phenyl-4-(trifluoromethyl)isoxazol-5-yl)-1,2,4-oxadiazol-3-yl) chroman-4-ol, TFA salt (19); racemic-ethyl 3-((3R*,4S*)-4-hydroxy-7-(5-(3-phenyl-4-(trifluoromethyl)isoxazol-5-yl)-1,2,4-oxadiazol-3-yl)chroman-3-ylamino)-2-methylpropanoate, TFA salt (20); racemic-3-((3R*,4S*)-4-hydroxy-7-(5-(3-phenyl-4-(trifluoromethyl)isoxazol-5-yl)-

1,2,4-oxadiazol-3-yl)chroman-3-ylamino) cyclopentanecarboxylic acid, TFA salt (21); racemic-3-((3R*,4S*)-4-hydroxy-7-(5-(3-phenyl-4-(trifluoromethyl) isoxazol-5-yl)-1,2,4-oxadiazol-3-yl)chroman-3-ylamino)-2-methylpropanoic acid, TFA salt (22); racemic-3-((3R*,4S*)-4-hydroxy-7-(5-(3-phenyl-4-(trifluoromethyl)isoxazol-5-yl)-1,2,4-oxadiazol-3-yl)chroman-3-ylamino)-2,2-dimethylpropanoic acid, TFA salt (23); (1S,3R)-3-((3S,4R)-4-hydroxy-7-(5-(3-phenyl-4-(trifluoromethyl)isoxazol-5-yl)-1,2,4-oxadiazol-3-yl)chroman-3-ylamino) cyclobutanecarboxylic acid, TFA salt (24); (1R,3S)-3-((3S,4R)-4-hydroxy-7-(5-(3-phenyl-4-(trifluoromethyl)isoxazol-5-yl)-1,2,4-oxadiazol-3-yl)chroman-3-ylamino) cyclobutanecarboxylic acid, TFA salt (25); 3-((3S,4R)-4-hydroxy-7-(5-(3-phenyl-4-(trifluoromethyl)isoxazol-5-yl)-1,2,4-oxadiazol-3-yl)chroman-3-ylamino)butanoic acid, TFA salt (26); 3-((3S,4R)-4-hydroxy-7-(5-(3-phenyl-4-(trifluoromethyl)isoxazol-5-yl)-1,2,4-oxadiazol-3-yl)chroman-3-ylamino)butanoic acid, TFA salt (27); 3-((3R,4S)-4-hydroxy-7-(5-(3-phenyl-4-(trifluoromethyl)isoxazol-5-yl)-1,2,4-oxadiazol-3-yl)chroman-3-ylamino)butanoic acid, TFA salt (28); 3-((3R,4S)-4-hydroxy-7-(5-(3-phenyl-4-(trifluoromethyl)isoxazol-5-yl)-1,2,4-oxadiazol-3-yl)chroman-3-ylamino)butanoic acid, TFA salt (29); 1-(((3R,4S)-4-hydroxy-7-(5-(3-phenyl-4-(trifluoromethyl)isoxazol-5-yl)-1,2,4-oxadiazol-3-yl)chroman-3-ylamino)methyl) cyclopropanecarboxylic acid, TFA salt (30); 1-(((3S,4R)-4-hydroxy-7-(5-(3-phenyl-4-(trifluoromethyl)isoxazol-5-yl)-1,2,4-oxadiazol-3-yl)chroman-3-ylamino)methyl) cyclopropanecarboxylic acid, TFA salt (31); (1S,3S)-3-((3R,4S)-4-hydroxy-7-(5-(3-phenyl-4-(trifluoromethyl)isoxazol-5-yl)-1,2,4-oxadiazol-3-yl)chroman-3-ylamino) cyclobutanecarboxylic acid, TFA salt (32); (1S,3s)-3-((3R,4S)-4-hydroxy-7-(5-(3-phenyl-4-(trifluoromethyl)isoxazol-5-yl)-1,2,4-oxadiazol-3-yl)chroman-3-ylamino) cyclobutanecarboxylic acid, TFA salt (33); 3-((3S,4R)-4-hydroxy-7-(5-(3-phenyl-4-(trifluoromethyl)isoxazol-5-yl)-1,2,4-oxadiazol-3-yl)chroman-3-ylamino)-2,2-dimethylpropanoic acid, TFA salt (34); 3-((3R,4S)-4-hydroxy-7-(5-(3-phenyl-4-(trifluoromethyl)isoxazol-5-yl)-1,2,4-oxadiazol-3-yl)chroman-3-ylamino)-2,2-dimethylpropanoic acid, TFA salt (35); 1-(((3S,4R)-4-hydroxy-7-(5-(3-phenyl-4-(trifluoromethyl)isoxazol-5-yl)-1,2,4-oxadiazol-3-yl)chroman-3-ylamino)methyl) cyclopentanecarboxylic acid, TFA salt (36); 1-(((3S,4R)-4-hydroxy-7-(5-(3-phenyl-4-(trifluoromethyl)isoxazol-5-yl)-1,2,4-oxadiazol-3-yl)chroman-3-ylamino)methyl) cyclohexanecarboxylic acid, TFA salt (37); 1-(((3R,4S)-4-hydroxy-7-(5-(3-phenyl-4-(trifluoromethyl)isoxazol-5-yl)-1,2,4-oxadiazol-3-yl)chroman-3-ylamino)methyl) cyclopentanecarboxylic acid, TFA salt (38); 1-(((3R,4S)-4-hydroxy-7-(5-(3-phenyl-4-(trifluoromethyl)isoxazol-5-yl)-1,2,4-oxadiazol-3-yl)chroman-3-ylamino)methyl) cyclohexanecarboxylic acid, TFA salt (39); 1-(((3S,4R)-4-hydroxy-7-(5-(3-phenyl-4-(trifluoromethyl)isoxazol-5-yl)-1,2,4-oxadiazol-3-yl)chroman-3-ylamino)methyl) cyclobutanecarboxylic acid, TFA salt (40); 1-(((3R,4S)-4-hydroxy-7-(5-(3-phenyl-4-(trifluoromethyl)isoxazol-5-yl)-1,2,4-oxadiazol-3-yl)chroman-3-ylamino)methyl) cyclobutanecarboxylic acid, TFA salt (41); 4,4'-((3R,4S)-4-hydroxy-7-(5-(3-phenyl-4-(trifluoromethyl)isoxazol-5-yl)-1,2,4-oxadiazol-3-ylazanediyl)dibutanoic acid, TFA salt (42); 4-((3R,4S)-4-hydroxy-7-(5-(3-phenyl-4-(trifluoromethyl)isoxazol-5-yl)-1,2,4-oxadiazol-3-yl)chroman-3-ylamino)pentanoic acid, TFA salt (43); 4-((3S,4R)-4-hydroxy-7-(5-(3-phenyl-4-(trifluoromethyl)isoxazol-5-yl)-1,2,4-oxadiazol-3-yl)chroman-3-ylamino)pentanoic acid, TFA salt (44); 3-((3R,4S)-4-hydroxy-7-(5-(3-phenyl-4-(trifluoromethyl)isoxazol-5-yl)-1,2,4-oxadiazol-3-yl)chroman-3-ylamino)-2-methylpropanoic acid, TFA salt (45); 3-((3R,4S)-4-hydroxy-7-(5-(3-phenyl-4-(trifluoromethyl)isoxazol-5-yl)-1,2,4-oxadiazol-3-yl)chroman-3-ylamino)-2-methylpropanoic acid, TFA salt (46); racemic (3R*,4S*)-7-(5-(3-phenyl-4-(trifluoromethyl)isoxazol-5-yl)-1,2,4-oxadiazol-3-yl)-3-(piperidin-1-yl)chroman-4-ol, TFA salt (47); racemic-2-(1-((3R*,4S*)-4-hydroxy-7-(5-(3-phenyl-4-(trifluoromethyl)isoxazol-5-yl)-1,2,4-oxadiazol-3-yl)chroman-3-yl)piperidin-3-yl)acetic acid, TFA salt (48); 2-(-1-((3R,4S)-4-hydroxy-7-(5-(3-phenyl-4-(trifluoromethyl)isoxazol-5-yl)-1,2,4-oxadiazol-3-yl)chroman-3-yl)piperidin-3-yl)acetic acid, TFA salt (49); 2-(-1-((3R,4S)-4-hydroxy-7-(5-(3-phenyl-4-(trifluoromethyl)isoxazol-5-yl)-1,2,4-oxadiazol-3-yl)chroman-3-yl)piperidin-3-yl)acetic acid (50); 2-(-1-((3S,4R)-4-hydroxy-7-(5-(3-phenyl-4-(trifluoromethyl)isoxazol-5-yl)-1,2,4-oxadiazol-3-yl)chroman-3-yl)piperidin-3-yl)acetic acid, TFA salt (51); 2-(-1-((3S,4R)-4-hydroxy-7-(5-(3-phenyl-4-(trifluoromethyl)isoxazol-5-yl)-1,2,4-oxadiazol-3-yl)chroman-3-yl)piperidin-3-yl) acetic acid, TFA salt (52); 3-((3R,4S)-4-Hydroxy-7-(5-(3-phenyl-4-(trifluoromethyl)isoxazol-5-yl)-1,2,4-oxadiazol-3-yl)chroman-3-ylamino)propanoic acid, TFA salt (53); 3-((3S,4R)-4-hydroxy-7-(5-(3-phenyl-4-(trifluoromethyl)isoxazol-5-yl)-1,2,4-oxadiazol-3-yl)chroman-3-ylamino)propanoic acid, TFA salt (54); racemic-3-(1-hydroxy-5-(5-(3-phenyl-4-(trifluoromethyl)isoxazol-5-yl)-1,2,4-oxadiazol-3-yl)-2,3-dihydro-1H-inden-2-ylamino)propanoic acid, TFA salt (55); racemic-3-(1-hydroxy-6-(5-(3-phenyl-4-(trifluoromethyl)isoxazol-5-yl)-1,2,4-oxadiazol-3-yl)-1,2,3,4-tetrahydronaphthalen-2-ylamino)propanoic acid, TFA salt (56); (1S,3S)-3-((3R,4S)-4-hydroxy-7-(5-(3-phenyl-4-(trifluoromethyl)isoxazol-5-yl)-1,2,4-oxadiazol-3-yl) chroman-3-ylamino)cyclohexanecarboxylic acid, TFA salt (57); (1R,3S)-3-((3S,4R)-4-hydroxy-7-(5-(3-phenyl-4-(trifluoromethyl)isoxazol-5-yl)-1,2,4-oxadiazol-3-yl)chroman-3-ylamino)cyclohexanecarboxylic, TFA salt (58); (1R,3R)-3-((3S,4R)-4-hydroxy-7-(5-(3-phenyl-4-(trifluoromethyl)isoxazol-5-yl)-1,2,4-oxadiazol-3-yl)chroman-3-ylamino) cyclohexanecarboxylic acid, TFA salt (59); (1R,3R)-3-((3S,4R)-4-hydroxy-7-(5-(3-phenyl-4-(trifluoromethyl)isoxazol-5-yl)-1,2,4-oxadiazol-3-yl)chroman-3-ylamino) cyclohexanecarboxylic acid (60); (1S,4S)-4-((3R,4S)-4-hydroxy-7-(5-(3-phenyl-4-(trifluoromethyl)isoxazol-5-yl)-1,2,4-oxadiazol-3-yl)chroman-3-ylamino) cyclohexanecarboxylic acid, TFA salt (61); (1R,4R)-4-((3R,4S)-4-hydroxy-7-(5-(3-phenyl-4-(trifluoromethyl)isoxazol-5-yl)-1,2,4-oxadiazol-3-yl)chroman-3-ylamino) cyclohexanecarboxylic acid, TFA salt (62); (1R,3S)-3-((3S,4R)-4-hydroxy-7-(5-(3-phenyl-4-(trifluoromethyl)isoxazol-5-yl)-1,2,4-oxadiazol-3-yl)chroman-3-ylamino) cyclohexanecarboxylic acid, TFA salt (63); (1S,3R)-3-((3R,4S)-4-hydroxy-7-(5-(3-phenyl-4-(trifluoromethyl)isoxazol-5-yl)-1,2,4-oxadiazol-3-yl)chroman-3-ylamino) cyclohexanecarboxylic acid, TFA salt (64); (1R,3R)-3-((3R,4S)-4-hydroxy-7-(5-(3-phenyl-4-(trifluoromethyl)isoxazol-5-yl)-1,2,4-oxadiazol-3-yl)chroman-3-ylamino) cyclohexanecarboxylic acid, TFA salt (65); (1R,3S)-3-((3R,4S)-4-hydroxy-7-(5-(3-phenyl-4-(trifluoromethyl)isoxazol-5-yl)-1,2,4-oxadiazol-3-yl)chroman-3-ylamino) cyclohexanecarboxylic acid, TFA salt (66); 2-((3S,4R)-4-hydroxy-7-(5-(3-phenyl-4-(trifluoromethyl)isoxazol-5-yl)-1,2,4-oxadiazol-3-yl)chroman-3-ylamino)acetic acid, TFA salt (67); 2-((3S,4R)-4-hydroxy-7-(5-(3-phenyl-4-(trifluoromethyl)isoxazol-5-yl)-1,2,4-oxadiazol-3-yl)chroman-3-ylamino)acetic acid, TFA salt (68); 4-((3R,4S)-4-hydroxy-7-

(5-(3-phenyl-4-(trifluoromethyl)isoxazol-5-yl)-1,2,4-oxadiazol-3-yl)chroman-3-ylamino)butanoic acid, TFA salt (69); 4-((3S,4R)-4-hydroxy-7-(5-(3-phenyl-4-(trifluoromethyl)isoxazol-5-yl)-1,2,4-oxadiazol-3-yl)chroman-3-ylamino)butanoic acid, TFA salt (70); racemic-2-(1-hydroxy-6-(5-(3-phenyl-4-(trifluoromethyl)isoxazol-5-yl)-1,2,4-oxadiazol-3-yl)-1,2,3,4-tetrahydronaphthalen-2-ylamino) acetic acid, TFA salt (71); and racemic-4-(1-hydroxy-6-(5-(3-phenyl-4-(trifluoromethyl)isoxazol-5-yl)-1,2,4-oxadiazol-3-yl)-1,2,3,4-tetrahydronaphthalen-2-ylamino) butanoic acid, TFA salt (72).

7. A pharmaceutical composition comprising a compound according to claim 1 or stereoisomers or pharmaceutically acceptable salts thereof, and a pharmaceutically acceptable carrier.

* * * * *

UNITED STATES PATENT AND TRADEMARK OFFICE
CERTIFICATE OF CORRECTION

PATENT NO. : 8,629,282 B2  
APPLICATION NO. : 13/883358  
DATED : January 14, 2014  
INVENTOR(S) : Robert Cherney et al.

Page 1 of 1

It is certified that error appears in the above-identified patent and that said Letters Patent is hereby corrected as shown below:

In the Claims:

Claim 3, col. 107, line 21, delete "$R^e$" and insert -- $R^c$ --;

Claim 5, col. 108, line 3, delete "—$NH(CH_2)_{1-3}$—$C(O)OR^8$," and insert -- —$NH(CH_2)_{1-3}C(O)OR^8$, --;

Claim 6, col. 109, line 33, delete "(1S,3s)" and insert -- (1S,3S) --;

Claim 6, col. 110, line 22, delete "Hydroxy" and insert -- hydroxy --; and

Claim 6, col. 110, line 38, delete "cyclohexanecarboxylic," and insert -- cyclohexanecarboxylic acid, --, therefor.

Signed and Sealed this
Fourteenth Day of October, 2014

Michelle K. Lee
*Deputy Director of the United States Patent and Trademark Office*